(12) United States Patent
Loring et al.

(10) Patent No.: US 10,987,110 B2
(45) Date of Patent: Apr. 27, 2021

(54) SURGICAL INSTRUMENTATION AND METHODS OF USE FOR IMPLANTING A PROSTHESIS

(71) Applicant: ENCORE MEDICAL, L.P., Austin, TX (US)

(72) Inventors: Thomas Loring, Philadelphia, PA (US); Victor Chan, Landing, NJ (US); Chulho Pak, Mahwah, NJ (US); Michael Daniels, Warsaw, IN (US); Stephen G. Gilbert, Morrisville, PA (US)

(73) Assignee: Encore Medical, LP, Austin, TX (US)

( * ) Notice: Subject to any disclaimer, the term of this patent is extended or adjusted under 35 U.S.C. 154(b) by 310 days.

(21) Appl. No.: 16/017,432

(22) Filed: Jun. 25, 2018

(65) Prior Publication Data

US 2018/0303490 A1 Oct. 25, 2018

Related U.S. Application Data

(63) Continuation of application No. 15/637,746, filed on Jun. 29, 2017, now Pat. No. 10,517,607, which is a
(Continued)

(51) Int. Cl.
*A61B 17/15* (2006.01)
*A61B 5/107* (2006.01)
(Continued)

(52) U.S. Cl.
CPC .......... *A61B 17/15* (2013.01); *A61B 17/025* (2013.01); *A61B 17/1682* (2013.01);
(Continued)

(58) Field of Classification Search
CPC .......... A61B 17/1775; A61B 2090/061; A61B 5/1072
(Continued)

(56) References Cited

U.S. PATENT DOCUMENTS

| 1,505,106 A | 8/1924 | Schröder |
| 4,289,123 A | 9/1981 | Dunn |

(Continued)

FOREIGN PATENT DOCUMENTS

| EP | 0554959 A1 | 8/1993 |
| EP | 1468652 | 10/2004 |

(Continued)

OTHER PUBLICATIONS

Extended European Search Report for Application No. EP09771054 dated Feb. 11, 2015.
(Continued)

*Primary Examiner* — Zade Coley
(74) *Attorney, Agent, or Firm* — Veros Legal Solutions, LLP

(57) ABSTRACT

A tissue resection guide for use with a datum includes a base releasably engagable with the datum. The tissue resection guide has a first frame fixed relative to the base and the first frame has at least one integral first guide path that is sized and configured to at least partially capture and guide a first tissue resection tool relative to the first frame.

18 Claims, 26 Drawing Sheets

Related U.S. Application Data continuation of application No. 15/294,307, filed on Oct. 14, 2016, now Pat. No. 10,299,800, which is a continuation of application No. 13/001,080, filed as application No. PCT/US2009/048699 on Jun. 25, 2009, now abandoned.

(60) Provisional application No. 61/178,343, filed on May 14, 2009, provisional application No. 61/133,186, filed on Jun. 25, 2008.

(51) Int. Cl.
| | |
|---|---|
| A61F 2/42 | (2006.01) |
| A61B 17/17 | (2006.01) |
| A61B 17/02 | (2006.01) |
| A61B 17/16 | (2006.01) |
| A61F 2/46 | (2006.01) |

(52) U.S. Cl.
CPC ...... *A61B 17/1739* (2013.01); *A61B 17/1775* (2016.11); *A61F 2/4202* (2013.01); *A61F 2/46* (2013.01)

(58) Field of Classification Search
USPC .................................................. 33/512, 613
See application file for complete search history.

(56) References Cited

U.S. PATENT DOCUMENTS

| | | | | |
|---|---|---|---|---|
| 4,524,766 | A * | 6/1985 | Petersen | A61B 17/154 606/184 |
| 5,020,519 | A | 6/1991 | Hayes et al. | |
| 5,122,144 | A | 6/1992 | Bert et al. | |
| 5,344,423 | A | 9/1994 | Dietz et al. | |
| 5,431,653 | A | 7/1995 | Callaway | |
| 5,486,180 | A | 1/1996 | Dietz et al. | |
| 5,514,139 | A | 5/1996 | Goldstein et al. | |
| 5,571,109 | A | 11/1996 | Bertagnoli | |
| 5,630,820 | A | 5/1997 | Todd | |
| 5,649,929 | A | 7/1997 | Callaway | |
| 5,766,259 | A | 6/1998 | Sammarco | |
| 5,810,827 | A | 9/1998 | Haines et al. | |
| 5,824,106 | A | 10/1998 | Fournol | |
| 5,885,299 | A | 3/1999 | Winslow et al. | |
| 6,013,081 | A * | 1/2000 | Burkinshaw | A61B 17/155 606/102 |
| 6,053,945 | A | 4/2000 | O'Neil et al. | |
| 6,090,114 | A | 7/2000 | Matsuno et al. | |
| 6,174,314 | B1 * | 1/2001 | Waddell | A61B 17/158 606/82 |
| 6,409,767 | B1 * | 6/2002 | Perice | A61F 2/4202 623/21.18 |
| 6,520,967 | B1 | 2/2003 | Cauthen | |
| 6,551,316 | B1 | 4/2003 | Rinner et al. | |
| 6,554,837 | B1 | 4/2003 | Hauri et al. | |
| 6,673,116 | B2 | 1/2004 | Reiley | |
| 6,755,841 | B2 | 6/2004 | Fraser et al. | |
| 6,852,130 | B2 | 2/2005 | Keller et al. | |
| 6,939,380 | B2 | 9/2005 | Guzman | |
| 7,011,687 | B2 | 3/2006 | Deffenbaugh et al. | |
| 7,025,790 | B2 * | 4/2006 | Parks | A61B 17/15 623/21.11 |
| 7,118,580 | B1 | 10/2006 | Beyersdorff et al. | |
| 7,204,851 | B2 | 4/2007 | Trieu et al. | |
| 7,419,491 | B2 | 9/2008 | Masini | |
| 7,470,273 | B2 | 12/2008 | Dougherty-Shah | |
| 7,491,205 | B1 | 2/2009 | Michelson | |
| 7,510,557 | B1 | 3/2009 | Bonutti | |
| 7,625,409 | B2 | 12/2009 | Saltzman et al. | |
| 7,632,279 | B2 | 12/2009 | Bastian | |
| 7,845,083 | B1 * | 12/2010 | Cora Rosa | B43L 7/02 33/42 |
| 8,002,841 | B2 | 8/2011 | Hasselman | |
| 2001/0029377 | A1 | 10/2001 | Aebi et al. | |
| 2001/0031969 | A1 | 10/2001 | Aebi et al. | |
| 2002/0116009 | A1 | 8/2002 | Fraser et al. | |
| 2002/0143343 | A1 | 10/2002 | Castro | |
| 2003/0212403 | A1 | 11/2003 | Swanson | |
| 2004/0102785 | A1 | 5/2004 | Hodorek et al. | |
| 2004/0117519 | A1 | 6/2004 | Trieu et al. | |
| 2004/0220582 | A1 | 11/2004 | Keller | |
| 2004/0249388 | A1 | 12/2004 | Michelson | |
| 2005/0004676 | A1 | 1/2005 | Schon et al. | |
| 2005/0027360 | A1 | 2/2005 | Webb et al. | |
| 2005/0055028 | A1 | 3/2005 | Haines | |
| 2005/0113842 | A1 | 5/2005 | Bertagnoli et al. | |
| 2005/0119665 | A1 | 6/2005 | Keller | |
| 2005/0165408 | A1 | 7/2005 | Puno et al. | |
| 2005/0245928 | A1 | 11/2005 | Colleran et al. | |
| 2006/0004377 | A1 | 1/2006 | Keller | |
| 2006/0100634 | A1 | 5/2006 | Ferguson | |
| 2006/0149278 | A1 | 7/2006 | Abdou | |
| 2006/0195116 | A1 | 8/2006 | Fox | |
| 2006/0235421 | A1 | 10/2006 | Rosa et al. | |
| 2006/0241634 | A1 | 10/2006 | Tuttle et al. | |
| 2007/0123901 | A1 | 5/2007 | Foley et al. | |
| 2007/0191857 | A1 | 8/2007 | Allard et al. | |
| 2007/0198025 | A1 | 8/2007 | Trieu et al. | |
| 2007/0233139 | A1 * | 10/2007 | Metcalfe | A61B 17/155 606/87 |
| 2007/0233140 | A1 | 10/2007 | Metzger et al. | |
| 2008/0015603 | A1 * | 1/2008 | Collazo | A61B 17/157 606/87 |
| 2008/0167655 | A1 | 7/2008 | Wang et al. | |
| 2008/0177272 | A1 | 7/2008 | Zucherman et al. | |
| 2008/0177275 | A1 | 7/2008 | Wing et al. | |
| 2008/0269756 | A1 | 10/2008 | Tomko et al. | |
| 2008/0275452 | A1 | 11/2008 | Lang et al. | |
| 2008/0306605 | A1 | 12/2008 | Hasselman | |
| 2009/0030422 | A1 | 1/2009 | Parsons et al. | |
| 2009/0048603 | A1 | 2/2009 | Hoag et al. | |
| 2009/0138021 | A1 | 5/2009 | Colquhoun et al. | |
| 2009/0182433 | A1 | 7/2009 | Reiley et al. | |
| 2009/0234362 | A1 | 9/2009 | Blain et al. | |
| 2009/0270869 | A1 | 10/2009 | Colquhoun et al. | |
| 2009/0275951 | A1 | 11/2009 | Arcenio et al. | |
| 2009/0306671 | A1 * | 12/2009 | McCormack | A61B 17/025 606/90 |
| 2010/0023066 | A1 | 1/2010 | Long et al. | |
| 2010/0069910 | A1 | 3/2010 | Hasselman | |
| 2010/0191244 | A1 | 7/2010 | White et al. | |
| 2010/0198355 | A1 | 8/2010 | Kofoed et al. | |
| 2010/0212138 | A1 | 8/2010 | Carroll | |
| 2012/0130434 | A1 | 5/2012 | Stemniski | |
| 2012/0271314 | A1 | 10/2012 | Stemniski et al. | |

FOREIGN PATENT DOCUMENTS

| | | | |
|---|---|---|---|
| FR | 2770393 | 5/1999 | |
| WO | 1997023172 A2 | 7/1997 | |
| WO | 9965403 A1 | 12/1999 | |
| WO | 2005084558 A1 | 9/2005 | |
| WO | WO-2005084558 A1 * | 9/2005 | ........... A61B 17/155 |
| WO | 2006052571 A2 | 5/2006 | |
| WO | 2007092728 A1 | 8/2007 | |
| WO | 2008076559 A1 | 6/2008 | |
| WO | 2008078082 A2 | 7/2008 | |
| WO | 2008157415 A1 | 12/2008 | |
| WO | 2009015009 A1 | 1/2009 | |
| WO | 2009158522 A1 | 12/2009 | |

OTHER PUBLICATIONS

International Search Report and Written Opinion dated Oct. 20, 2009 for PCT/US2009/048669.
International Search Report dated Oct. 20, 2000 for PCT/US2009/048699.
Link S.T.A.R. Scandinavian Total Ankle Replacement Brochure; Waldemar Link GmbH & Co.; Hamburg, Germany;1990.
Link S.T.A.R. Scandinavian Total Ankle Replacement Brochure; Waldemar Link GmbH & Co.; Hamburg, Germany;1993.

(56) References Cited

OTHER PUBLICATIONS

Small Bones Innovations, Inc., Star™ Surgical Technique, 2009-2013.
Extended European Search Report including Written Opinion for Application No. EP18202660.9 dated Jun. 18, 2019, pp. 1-7.

* cited by examiner

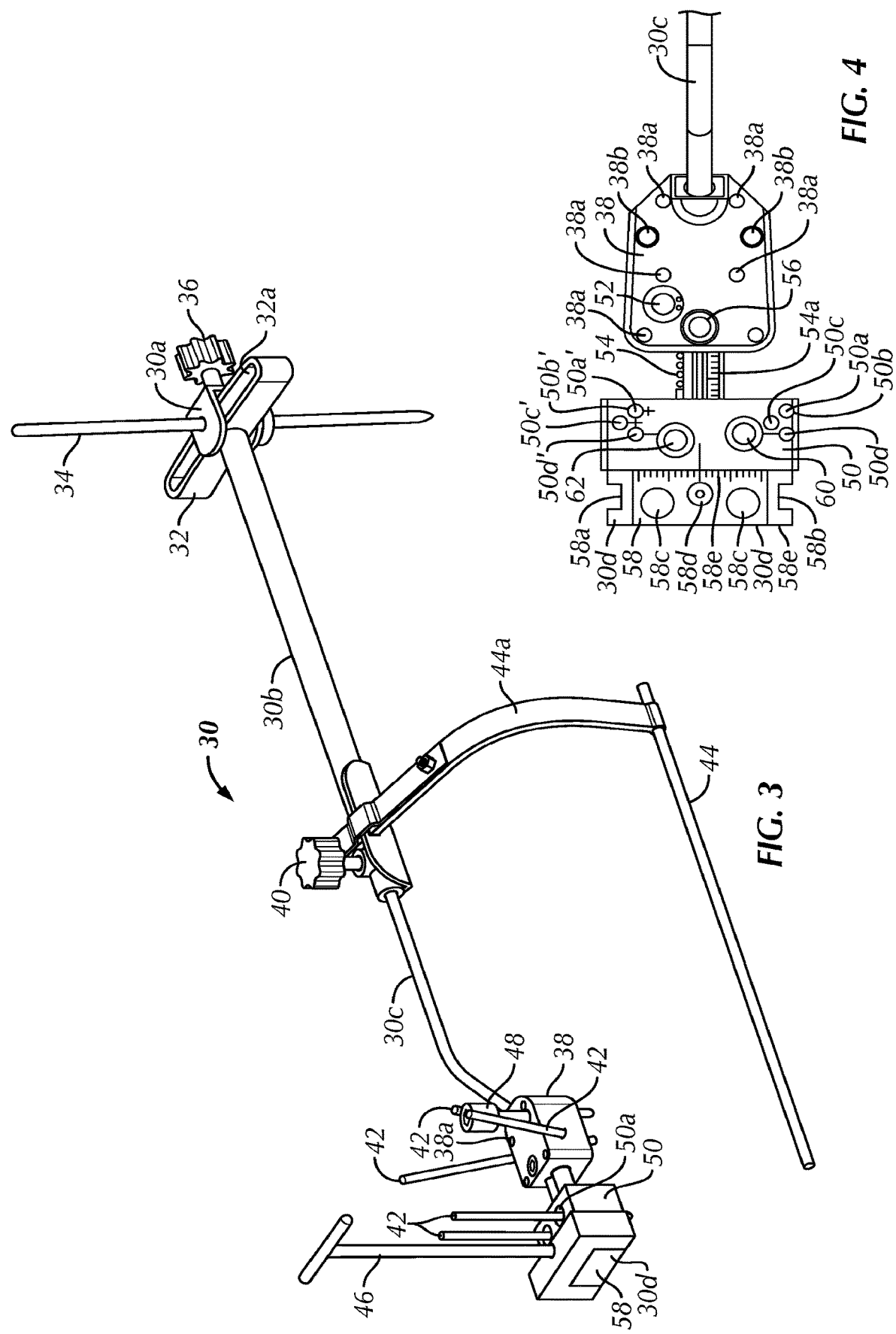

SURGICAL INSTRUMENTATION AND METHODS OF USE FOR IMPLANTING A PROSTHESIS

CROSS-REFERENCE TO RELATED APPLICATIONS

This application is a continuation of U.S. application Ser. No. 15/637,746 filed Jun. 29, 2017, which is a continuation of U.S. application Ser. No. 15/294,307 filed Oct. 14, 2016, which is a continuation of U.S. application Ser. No. 13/001,080, filed Feb. 10, 2012, which is a national phase entry under 35 U.S.C § 371 of International Application No. PCT/US2009/48699 filed Jun. 25, 2009, published in English, which claims the benefit of U.S. Provisional Patent Application No. 61/133,186 filed Jun. 25, 2008 and entitled "Instrumentation for Prosthesis" and U.S. Provisional Patent Application No. 61/178,343 filed May 14, 2009, and entitled "Surgical Instrumentation and Methods of Use for Implanting an Endoprothesis," the disclosures of which are hereby incorporated by reference herein in their entirety.

BACKGROUND OF THE INVENTION

The present invention generally relates to surgical instrumentation and methods for such procedures such as, for example, a total joint replacement within a patient.

Various endoprosthetic devices are known for repairing or replacing joints in a patient. Specifically, it is known to use an endoprosthesis to replace a damaged ankle joint. The ankle joint is a comparatively small joint relative to the weight bearing and torque the joint must withstand. These factors have made the design of total ankle joint replacements technically challenging. Total ankle replacement has been investigated since the 1970's with initially promising results, but the procedure was essentially abandoned in the 1980's due to a high long-term failure rate, both in terms of pain control and improved function. However, researchers have continued to investigate new designs, which can be broadly subdivided into constrained and unconstrained designs. Constrained designs offer the advantage of greater stability, but with decreased mobility and increased stress at the bone implant interface, potentially leading to a greater risk of early loosening and failure. Unconstrained designs provide improved range of motion in multiple planes, but at the expense of stability. Early devices investigated were implanted with cement fixation, which in recent years has given way to cementless designs. One such cementless, non-constrained mobile bearing device that has proven to be successful is a total ankle replacement. An example of the total ankle replacement, shown in FIGS. 1 and 2, is further described in U.S. Pat. No. 6,852,130 and is commercially known as the S.T.A.R.® or the Scandinavian Total Ankle Replacement System.

Total joint replacements, such as the S.T.A.R.®, have been implanted to repair damaged joints using a combination of cut guides and free hand cutting and shaping to sufficiently prepare the bone contacting the total joint replacement.

It would be desirable to reduce the amount of measuring, free hand cutting and/or re-mounting of cut guides to the remaining healthy bone structure to efficiently and accurately prepare the resected tissue surface receiving the total joint replacement with repeatable results and minimum bone removal.

BRIEF SUMMARY OF THE INVENTION

In one embodiment, there is a distractor that includes a handle that is adjustable between an insertion position and a distraction position, a datum securement that is attached to the handle and releasably engagable with a datum, and a tissue engaging portion that is attached to the handle and movable with respect to the datum securement as the handle is adjusted between the insertion position and the distraction position. In another embodiment, the handle includes a first handle portion that extends from the datum securement and a second handle portion that extends from the tissue engaging portion. In another embodiment the second handle portion is pivotable with respect to the first handle portion. In another embodiment, the first handle portion is releasably attached to the second handle portion. In a further embodiment, the first handle portion is generally planar from the distal end to the proximal end. In another embodiment, the second handle has an angular orientation between a distal end and a proximal end. In another embodiment, the second handle portion further comprises a grip portion opposite a tissue engaging portion and an inflection point between the tissue engaging portion and the grip portion wherein the second handle portion is attachable to the first handle portion proximate the inflection point. In another embodiment, the second handle portion includes a distal portion that is generally parallel the first handle portion when the distractor is in the insertion position and is not generally parallel to the first handle portion when the distractor is in the distraction position. In a further embodiment, a ratchet extends between the first handle portion and the second handle portion. In another embodiment, the ratchet is positioned at the proximal end of the distractor. In another embodiment, the ratchet is pivotally attached to the first handle portion. In another embodiment, the ratchet is detachable from the second handle portion. In another embodiment, the tissue engaging portion includes a paddle pivotally attached to the second handle portion. In another embodiment, the paddle is generally parallel with the handle in the insertion position. In another embodiment, the paddle is generally flush with the handle in the insertion position. In another embodiment, at least a portion of the paddle is sized and configured to extend over the datum and between a plurality of projections extending from the datum. In another embodiment, a proximal end of the paddle is heavier than the distal end of the paddle. In another embodiment, the datum securement includes an abutment member, the abutment member engagable with the datum and movable from a secured position to a released position. In a further embodiment, a datum lock is configured to move the datum datum securement from a secured position to a released position. In another embodiment, the datum lock includes a rotatable nut that threadably engages a shaft extending from the datum securement. In another embodiment, the handle further comprises a grip portion having a plurality of indentations separated by columns that are oriented perpendicular to a longitudinal axis of the handle.

In one embodiment, there is a tissue resection guide for use with a datum that includes a base releasably engagable with the datum and having a first frame fixed relative to the base and the first frame having at least one integral first guide path sized and configured to at least partially capture and guide a first tissue resection tool relative to the first frame. In another embodiment, the base further includes a second frame fixed relative to the base, the second frame having at least one integral second guide path sized and configured to at least partially capture and guide a second tissue resection tool relative to the first frame. In another embodiment, the second frame has an at least partially open sidewall. In another embodiment, the at least partially open sidewall includes two tapered and spaced apart side wall segments. In another embodiment, the base has a bottom surface engagable with the datum and a top surface opposite the bottom surface of the base, the at least one second guide path is at least partially closed proximate the top surface of the base and substantially open proximate the bottom surface of the base. In another embodiment, the at least one first guide path is raised upwardly further from the base in a direction generally normal to the top of the base than the at least one second guide path. In another embodiment, at least one of the first and second frames are angled inwardly toward the base. In another embodiment, the second frame has an angle of inclination relative to the base greater than an angle of inclination between the base and the first frame. In another embodiment, the at least one second guide path and a surface of the datum define a resection plane when the base is engaged with the datum. In another embodiment, the at least one guide path includes an enlarged end. In another embodiment, at least two enlarged ends are on opposite lateral sides of the first frame. In another embodiment, the at least one first guide path includes two substantially parallel longitudinal guide paths. In one embodiment, the two substantially parallel longitudinal guide paths has a longitudinal axis and an enlarged end, and wherein the longitudinal axes of adjacent longitudinal guide paths are spaced apart from one another by a distance that is less than a diameter of one of the enlarged ends. In one embodiment, the at least one first guide path and a surface of the datum define a resection plane along which the tissue resection tool is guided when the base is engaged with the datum. In one embodiment, the base has a bottom surface engagable with the datum and a top surface opposite the bottom surface of the base, the at least one first guide path is at least partially closed proximate the top surface of the base and substantially open proximate the bottom surface of the base. In one embodiment, the at least one first guide path is raised upwardly from the top surface base in a direction generally normal to the top of the base. In one embodiment, the first frame includes at least one viewing window extending through an outer surface of the first frame. In one embodiment, the first frame includes an alignment line intersecting with the at least one viewing window.

In one embodiment there is a datum engagable with at least one tissue resection guide, the datum includes a bottom surface engagable with a tissue surface, a first side surface that extends upwardly from the bottom surface to define a first acute angle with the bottom surface, a second side surface that extends upwardly from the bottom surface to define a second acute angle with the bottom surface, and a top surface that is connected to the first and second side surfaces and has a securement releasably engagable with the at least one tissue resection guide. In another embodiment, a surface extends upwardly from the bottom surface to define a third acute angle with the bottom surface. In another embodiment, a fourth side surface extends upwardly from the bottom surface to define an obtuse angle with the bottom surface. In another embodiment, a width of the bottom surface measured between the first and fourth side surfaces is smaller than the length of the bottom surface measured between the first and second side surfaces. In another embodiment, the third acute angle is smaller than the first and second acute angles. In another embodiment, a fourth angle between the first side surface and the third side surface is less than a fifth angle between the second side surface and the third side surface. In another embodiment, the third side surface is between the first and second side surfaces. In another embodiment the top surface is generally parallel to the bottom surface. In another embodiment, the securement includes a threaded aperture.

In one embodiment, there is a method of implanting a prosthesis between first and second bones, the method includes the steps of: resecting tissue from the first bone to expose a first resected tissue surface; resecting tissue from the second bone to expose a second resected tissue surface; attaching a datum to the second resected tissue surface; attaching to the datum a first tissue resection guide configured to guide the first tissue resection tool; further resecting tissue from the second bone with the first tissue resection tool while the first tissue resection tool is guided by the first tissue resection guide to expose a third resected tissue surface; and placing the prosthesis in contact with the first and second resected tissue surfaces to operatively connect the first and second bones. In a further embodiment, the method includes attaching a second tissue resection guide on the datum; and forming a fourth resected tissue surface by further resecting tissue from the second bone using the second tissue resection guide to guide a second tissue resection tool. In another embodiment, the third resected tissue surface is adjacent to a first side of the datum and the fourth resected tissue surface is adjacent to a second side of the datum. In another embodiment, the third resected tissue surface is generally aligned with the first side of the datum and the fourth resected tissue surface is generally aligned with the second side of the datum. In another embodiment, resecting the first bone further includes applying a second tissue resection tool to the first bone along a second tissue resection guide fixed relative to the first bone. In a further embodiment, the method includes determining the position of the second tissue resection guide based upon the position of a spacer guide attached to the second tissue resection guide. In a further embodiment, the method includes fixing the second bone relative to the first bone prior to resecting tissue from the second bone to expose the second resected tissue surface. In a further embodiment, the method includes aligning a feature of the first tissue resection tool with a feature of the first tissue resection guide to achieve a predetermined resection depth. In a further embodiment, the method includes positioning the datum on the second resected tissue surface with a distractor; and moving the first bone away from the second bone with the distractor. In a further embodiment, the method includes placing a window trial over the second resected tissue surface and third resected tissue surfaces to evaluate the size and shape of the second resected tissue surface and the third resected tissue surface. In a further embodiment, the method includes positioning a barrel cut guide against the first resected tissue surface; inserting a drill bit through an aperture in the barrel cut guide; and drilling a cavity into the first bone using the drill bit, the cavity receiving a portion of the prosthesis. In another embodiment, the first bone is the tibia and the second bone is the talus. In another embodiment, the first and second resected tissue surfaces are comprised of bone.

In one embodiment, there is a tissue resection kit including a datum that is engagable with a tissue surface, and a first tissue resection guide having a first base releasably engagable with the datum and having a first frame fixed relative to the first base, the first frame having at least one integral first guide path sized and configured to at least partially capture and guide a first tissue resection tool relative to the first frame. In another embodiment, the first base includes a third frame fixed relative to the first base, the third frame having at least one integral third guide path sized and configured to at least partially capture and guide a third tissue resection tool relative to the first frame. In another embodiment, the at least one first guide path and a surface of the datum define a resection plane along which the tissue resection tool is guided when the first base is engaged with the datum. In a further embodiment, the tissue resection kit includes a second tissue resection guide having a second base releasably engagable with the datum and having a second frame fixed relative to the second base, the second frame having at least one integral second guide path sized and configured to at least partially capture and guide a second tissue resection tool relative to the second frame. In a further embodiment, the tissue resection kit includes a distractor releasably engagable with the datum. In a further embodiment, the tissue resection kit includes a window trial engagable with the tissue surface, the window trial having the general shape and configuration of a prosthesis and having one or more apertures for viewing the tissue surface.

In one embodiment there is an alignment guide for attaching one or resection guides to a bone and includes an elongated member having a first end, a second end and a longitudinal axis extending between the first and second ends, a first securement proximate the first end and configured to releasably connect with the bone, an attachment block proximate the second end and having a second securement configured to releasably connect with the bone and a grip tool releasably connectable to the attachment block and generally perpendicular to the attachment block in an engaged position. In a further embodiment, the alignment guide includes an elongated alignment member attached to the elongated member and spaced laterally from and generally parallel to the longitudinal axis.

BRIEF DESCRIPTION OF THE DRAWINGS

The foregoing summary, as well as the following detailed description of embodiments of the surgical instrumentation and methods of use for implanting a total joint replacement will be better understood when read in conjunction with the appended drawings of exemplary embodiments. It should be understood, however, that the invention is not limited to the precise arrangements and instrumentalities shown.

In the drawings:

FIG. 3 is a perspective view of an alignment guide in accordance with an exemplary embodiment of the present invention;

FIG. 4 is a top view of the alignment guide shown in FIG. 3 with the positioning tool removed;

DETAILED DESCRIPTION

Figure 1:
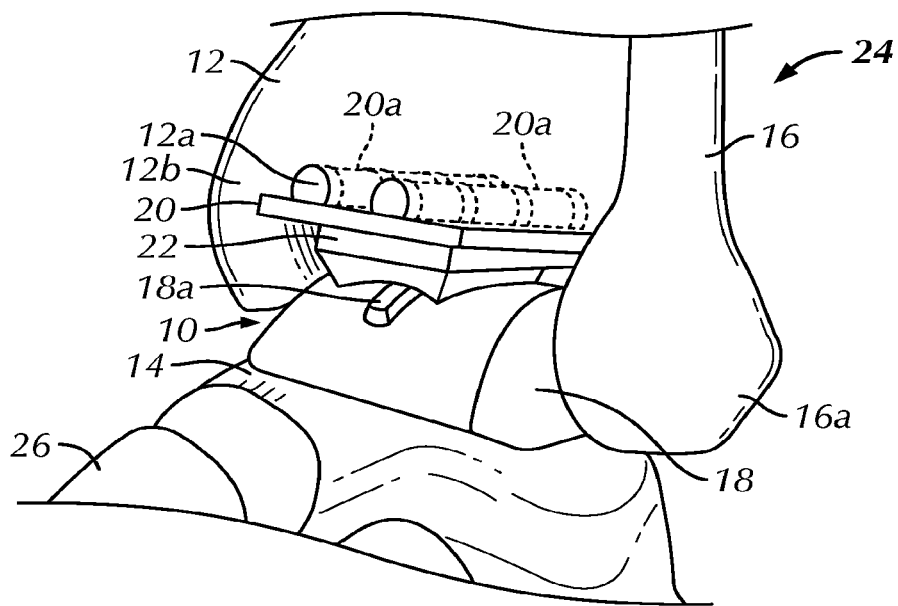
FIG. 1 is a perspective view of a total joint replacement implanted between first and second bones.

Referring to the drawings in detail, wherein like reference numerals indicate like elements throughout, there is shown in FIGS. 1-35 surgical instrumentation and methods of use for installing a prosthesis or endoprosthesis such as, for example, a total joint replacement, generally designated 10, between first and second bones 12, 14, in accordance with exemplary embodiments of the present invention.

Figure 2:
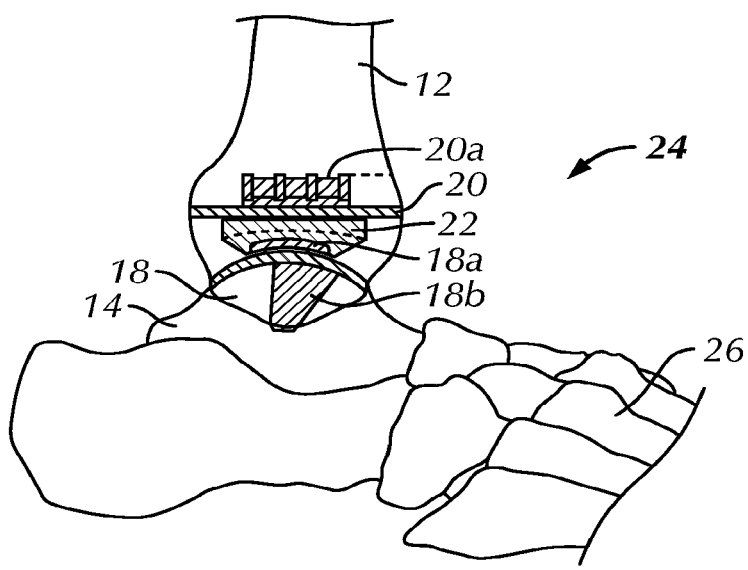
FIG. 2 is a side, partially cross-section, partially transparent side view of the implanted total joint replacement of FIG. 1.

Referring to FIGS. 1 and 2, in one embodiment, the total joint replacement 10 may be an ankle joint and the first and second bones 12, 14 may be the tibia and the talus respectively. A third bone 16, such as the fibula, may also contact the total joint replacement 10. In one embodiment, the total joint replacement 10 is a total ankle replacement such as described in U.S. Pat. No. 6,852,130 which is hereby incorporated by reference in its entirety, and is commercially known as the S.T.A.R.® or the Scandinavian Total Ankle Replacement System. However, the present invention may be used for resecting tissue surfaces in implanting any prosthetic device.

In one an embodiment, the total joint replacement 10 includes a first endoprosthetic component 18 that engages the first bone 12 and a second endoprosthetic component 20 that engages the second bone 14. In one embodiment, the second endoprosthetic component 20 includes projections 20a that are slidable into resected cavities 12a in the first bone 12. In one embodiment, the total joint replacement 10 further includes a middle endoprosthetic component 22 that is positioned between the first and second endoprosthetic components 18, 20 to provide a three piece total joint replacement 10. The first endoprosthetic component 18 may include a rib 18a for preventing lateral movement of the middle endoprosthetic component 22 relative to the first endoprosthetic component 18. The first endoprosthetic component 18 may also include a fin 18b for extending into the second bone 14 and stabilizing the total joint replacement 10 relative to the second bone 14.

In one embodiment, the first endoprosthetic component 18 has the approximate dimensions set forth in Table 1 below.

TABLE 1

First Endoprosthetic Component Dimensions (in mm)

| | XX - Small | X-Small | Small | Medium | Large |
|---|---|---|---|---|---|
| ML Dimension (Width) | 28 | 30 | 34 | 36 | 38 |
| AP Dimension (Depth) | 29 | 31 | 35 | 35 | 35 |

In one embodiment the second endoprosthetic component 20 has the approximate dimensions set forth in Table 2 below.

TABLE 2

Second Endoprosthetic Component Dimensions (in mm)

| | X-Small | Small | Medium | Large | X-Large |
|---|---|---|---|---|---|
| ML Dimension (Width) | 30 | 32 | 32.5 | 33 | 33.5 |
| AP Dimension (Depth) | 30 | 30 | 35 | 40 | 45 |

Though further description herein of the first and second bones 12, 14 may refer to the tibia 12 and talus 14 and respective anatomical directions, the instrumentation and methods disclosed herein are not limited to the tibia 12, talus 14, fibula 16 and respective anatomical directions. The first, second and third bones 12, 14, 16 as disclosed herein may be any jointed bones such as the elbow, knee, shoulder or knuckle or a portion thereof that are prepared for the installation or implantation of the total joint replacement 10 or an endoprosthetic component from any direction. The various instrumentation and methods described below may be used in different orientations depending on the application and reference to anatomical orientation as used herein is for exemplary purposes. Additionally, though a left ankle 24 and foot 26 are shown and described, the various instrumentation and methods described below may be used in conjunction with and/or oriented for use with the right ankle (not shown or illustrated) or another applicable joint.

Alignment Guide

Referring to the embodiment of FIG. 3, an alignment guide 30 may be used to assist in implanting the total joint replacement 10. The alignment guide 30 may be used to orient one or more instruments, such as first and second tissue resection guides 66, 90 relative to the first bone 12 as described further below. The alignment guide 30 includes a first end 30a and a second end 30d. The alignment guide 30 may include a first body 30b proximate the first end 30a and a second body 30c proximate the second end 30d. In one embodiment, the first and second bodies 30b, 30c are each comprised of one or more generally cylindrical elongated rods. However, the first and second bodies 30b, 30c may have any suitable configuration and shape such as a tube that encloses a leg 84 (see FIG. 17). The alignment guide 30 may include a pin receiver 32. The pin receiver 32 may be proximate the first end 30a. The pin receiver 32 may include a slot 32a and/or a plurality of apertures (not shown) for receiving one or more pins 34 at a plurality of lateral positions. The pin receiver 32 may also move up and down the pin 34 as described further below. In one embodiment, the pin receiver 32 includes a first securement 36 such as a manually adjustable screw that secures the pin receiver 32 to the pin 34 and prevents the alignment guide 30 from moving relative to the pin 32. In one embodiment, the pin 32 is a self drilling pin and is approximately 3.2 mm in diameter. However, the pin 32 may have any suitable configuration and size.

An attachment block 38 may be connected to the second body 30*c* of the alignment guide 30. The attachment block 38 may be configured to secure the second end 30*d* of the alignment guide 30 to the first bone 12. The attachment block 38 may serve as a datum for one or more resections as described further below. In one embodiment, the second body 30*c* of the alignment guide 30 is telescopically connected to the first body 30*b* of the alignment guide 30. In one an embodiment, the second body 30*c* of the alignment guide 30 may be fixed with respect to the first body 30*a* of the alignment guide 30 through use of a second securement 40. The second securement 40 may be a manually adjustable screw. Alternatively, the length of the alignment guide 30 may be fixed and the attachment block 38 may adjust relative to the alignment guide 30. The attachment block 38 may include one or more apertures 38*a* each for receiving a pin 42. In one embodiment, the pins 42 may be inserted through the attachment block 38 at an angle such as an oblique angle as shown in FIG. 3. The pins 42 may be comprised of Kirschner or K-wire. In one embodiment the pins are approximately 2.4 mm in diameter. However, the pins 42 may have any suitable configuration and diameter. Though the same reference number is used for the additional pins 42 described below, the additional pins 42 described below may be generally identical or different than the pins 42 used to secure the attachment block 38 relative to the first bone 12.

The attachment block 38 may include one or more space adjustments 48 that may be threadably received in a respective aperture 38*b*. One or more space adjustments 48, such as a manually adjustable screw, may be provided to stabilize the attachment block 38 relative to the first bone 12. The space adjustment 48 may alternatively or in addition help to position the attachment block 38 a distance normal to the first bone 12 by extending below the attachment block 38 an adjustable distance.

An alignment rod 44 is optionally spaced laterally from the alignment guide 30 and is configured to be positionable alongside the first bone 12. In one embodiment, the alignment rod 44 is generally parallel with the first body 30*b* of the alignment guide 30. An X-ray image intensifier, such as a C-arm or other imaging device (not shown), may be used to align the alignment rod 44 generally parallel with a feature 12*f* of the first bone 12. In one embodiment the alignment rod 44 is aligned to be generally parallel to the longitudinal axis of the first bone 12. The alignment rod 44 may be attached to the first body 30*b* of the alignment guide 30 by an arm 44*a*. A grip member or positioning tool 46 such as a T-grip may releaseably connect or attach to the attachment block 38 to assist in orienting the attachment block 38 relative to the first bone 12. In one embodiment, the grip member 46 is generally perpendicular to a longitudinal axis of the alignment guide 30 in an engaged position.

Referring to the embodiment of FIG. 4, the attachment block 38 may include a first positioning block 50. In one embodiment, the attachment block 38 is fixed relative to the first bone 12 and the first positioning block 50 is movable relative to the attachment block 38. In one embodiment, the first positioning block 50 is adjustable relative to the attachment block 38 in first and second directions, e.g. superior and inferior anatomical directions, that are generally parallel to the length of the alignment guide 30. The attachment block 38 may include a first key adjustment 52 that may be configured to set the distance between the attachment block 38 and the first positioning block 50. In one embodiment, the first key adjustment 52 engages a first rack 54 that extends from the first positioning block 50 and into the attachment block 38. Alternatively, the first rack 54 may extend from the attachment block 38 and extend into the first positioning block 50. The first key adjustment 52 may be turned using a tool such as a gear key or screw driver (not shown). Alternatively, the key adjustment 52 may be a manually adjustable screw. The attachment block 38 optionally includes a first position lock 56 that releasably fixes the distance between the attachment block 38 and the first positioning block 50. In one embodiment, the first position lock 56 is a set screw. However, the first position lock 56 may be any locking device such as projection extending into the first key adjustment 52.

The first positioning block 50 may include one or more pin apertures 50*a* each for receiving a pin 42 that extends into the first bone 12. In one embodiment, the first positioning block 50 includes a first plurality of pin apertures 50*a*. The first plurality of apertures 50*a* may be provided to move the first positioning block 50 a predetermined distance with respect to the one or more pins 42 for measuring additional resection of the first bone 12 if necessary as described further below. The first plurality of pin apertures 50*a* may include a first pin aperture 50*b* spaced a predetermined distance from a second pin aperture 50*c* in a direction generally parallel to the length of the alignment guide 30, e.g. in an inferior anatomical direction. In one embodiment, a third pin aperture 50*d* is spaced a predetermined distance from the second pin aperture 50*c* in a direction generally parallel to the length of the alignment guide 30, e.g. in an inferior anatomical direction. The first plurality of pin apertures 50*a* may include additional apertures 50*a*.

In one embodiment, the first and second pin apertures 50*b*, 50*c* are spaced from each other a distance equal to the space between the second and third pin apertures 50*c*, 50*d*. In one embodiment, the first positioning block 50 includes a second plurality of pin apertures 50*a'*. The second plurality of pin apertures 50*a'* may include first, second and third pin apertures 50*b'*, 50*c'*, 50*d'* that each correspond in placement along the first positioning block to respective first, second and third pin apertures 50*b*, 50*c*, 50*d* of the first plurality of pin apertures 50*a*. In one embodiment, the predetermined intervals between adjacent pin apertures 50*a*, 50*a'* are each generally 0.5 mm to generally 5 mm such that the positioning block may be moved relative to the pins 42 the predetermined distance and 0.5 mm to 5 mm of additional tissue can be resected from the end of the first bone 12 in one or more additional resections. In one embodiment, the predetermined intervals between adjacent pin apertures 50*a* are approximately 2 mm. Alternatively, the first positioning block 50 is movable relative to the pins 42 such as having expanding and contracting ends (not shown) or the positioning block 50 may include a slot (not shown) that releasably engages one or more pins 42 to adjust the position of the first positioning block 50 relative to the first bone 12.

The attachment block 38 may include a second positioning block 58 that is movable relative to the portion of the attachment block 38 fixed relative to the first bone 12. In one embodiment, the second positioning block 58 is movable relative to the first positioning block 50. Alternatively, the first and second positioning blocks 50, 58 are integral. The second positioning block 58 may be adjustable relative to the attachment block 38 in third and fourth directions, e.g. lateral and medial anatomical directions, that may be generally perpendicular to the length of the alignment guide 30. The first positioning block 50 may include a second key adjustment 60 that is used to adjust the position of the second positioning block 58 relative to the attachment block 38.

In one embodiment, the second key adjustment 60 engages a second rack (not visible) that extends along the second positioning block 58. The second key adjustment 60 may be turned using a tool such as a gear key or screw driver (not shown) to move the second positioning block 58 relative to the first positioning block 50. Alternatively, the second key adjustment 60 may be a manually adjustable screw. The second rack may be alternatively attached to the first positioning block 50. The first positioning block 50 optionally includes a second position lock 62 that releasably fixes the lateral alignment between the second positioning block 58 and the first positioning block 50 to prevent unintentional movement between the first and second positioning blocks 50, 58. In one embodiment, the second position lock 62 is a set screw. However, the second position lock 62 may be any locking device such as projection extending into the second key adjustment 60.

In one embodiment, the second positioning block 58 includes first and second grooves 58a, 58b on opposing lateral sides of the second positioning block 58. The first and second grooves 58a, 58b may be receive and mate with the positioning tool 46 and additional instrumentation as described below to prevent movement between the second positioning block 58 and the positioning tool 46 or additional instrumentation. The positioning tool 46 may be used to assist in positioning the attachment block 38 relative to the first bone 12. The second positioning block 58 may include a threaded aperture 58d for securing to additional instrumentation as described below. The second positioning block 58 may include one or more apertures 58c each for viewing the first bone 12 during positioning of the attachment block 38 using a C-arm or other imaging device. In one embodiment, the apertures 58c show up on the imaging device as circular if the attachment block 38 is correctly positioned with respect to the first bone 12 and oval shaped if the attachment block 38 is misaligned with respect to the first bone 12. The apertures 58c may generally align with where the cavities 12a (FIG. 1) are to be drilled.

First Tissue Resection Guide

Figure 5:
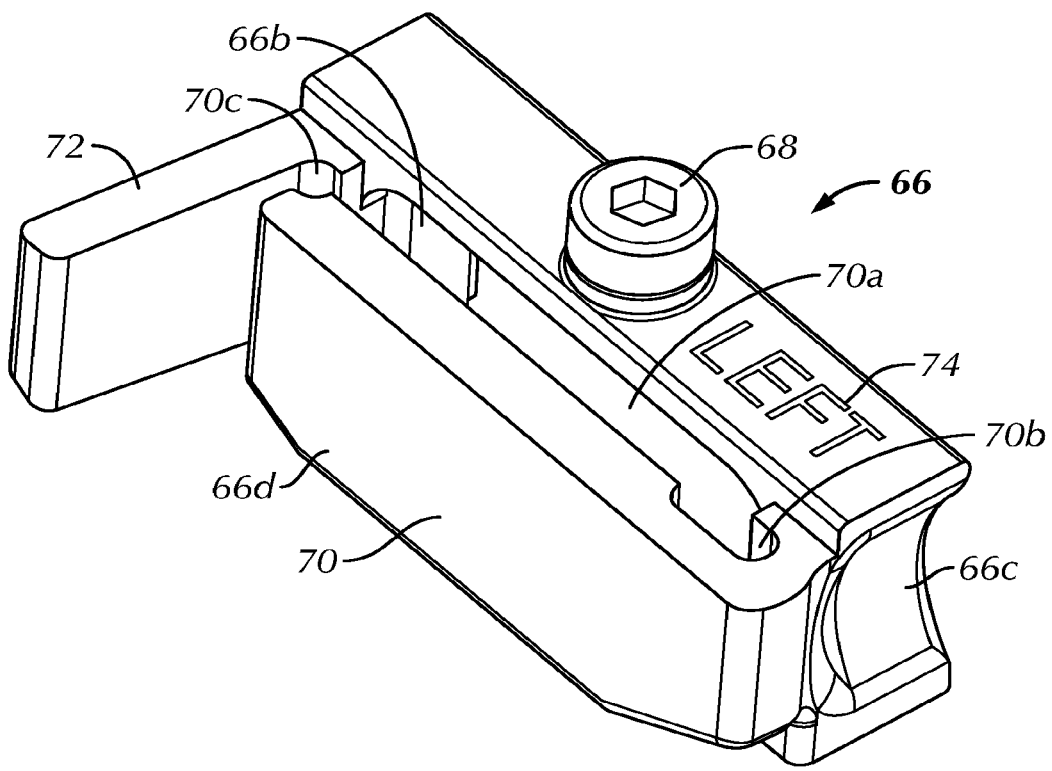
FIG. 5 is a perspective view of a first tissue resection guide in accordance with an exemplary embodiment of the present invention.

Referring to the embodiment of FIG. 5, a first tissue resection guide 66 may be provided for resecting the first bone 12 and exposing a first resected tissue surface 100 as described below. In one embodiment, the first resected tissue surface 100 is bone tissue. In alternative embodiments, the first resected tissue surface 100 is another tissue such as cartilage and/or a combination of different tissue. The first tissue resection guide 66 may removably attach to the second positioning block 58. The first tissue resection guide 66 may include a fastener 68 that releasably attaches the first tissue resection guide 66 to the aperture 58d (see FIG. 4) in the second positioning block 58. In one embodiment, the fastener 68 is an Allen screw. However, the fastener 68 may be any attachment device such as a snap or magnet. The first tissue resection guide 66 may include first and second projections 66a, 66b (see FIGS. 7 and 8 for the second projection 66b) that may be received in the first and second grooves 58a, 58b, respectively of the second positioning block 58. The first and second projections 66a, 66b may help to prevent the first tissue resection guide 66 from moving or rotating with respect to the second positioning block 58.

In one embodiment, the first tissue resection guide 66 includes a first guide path 70 for resecting the first bone 12. The first guide path 70 may be a slot 70a such that the guide path captures a tissue resection tool such as a blade (not shown). The slot 70a may be generally rectangular and oriented such the blade is captured and guided in a direction generally perpendicular to the length of the first bone 12, e.g. the medial and lateral anatomical directions. The blade may be guided at a slight angle relative the longitudinal axis of the first bone 12 as described further below. An end surface 58e of the second positioning block 58 (see FIG. 4) and the first guide path 70 may define a resection plane. In an alternative embodiment, the first guide path 70 is open toward one lateral side (not shown) such that the first tissue resection tool is guided on only one side. The slot 70a may include pin apertures 70b, 70c at the ends of the slot 70a for inserting pins 42 (not shown). The pins 42 may be used to protect features of the first and third bones 12, 16 such as medial and lateral malleolus 12e, 16a. The first bone 12 may be cut until the first tissue resection tool contacts the pins 42. The pins 42 may prevent over or notched cuts in the first bone 12.

In one embodiment, the first tissue resection guide 66 includes a second guide path 72. The second guide path 72 is optionally provided to guide the tissue resection tool for a second resection. The second guide path 72 may be generally perpendicular to the blade guard 70. In one embodiment, the second guide path 72 is open toward one lateral side and defines only one side of a resection plane. In an alternative embodiment, the second guide path 72 is closed similar to the first guide path 70 to capture the blade on two opposing sides (not shown).

The first tissue resection guide 66 may include indicia 74 indicating which foot (i.e. left or right) 26 the first tissue resection guide 66 is to be used on. The indicia 74 may also, or in the alternative, indicate a size of the first tissue resection guide 66. The first tissue resection guide 66 may include an indent 66c on each lateral side of the first tissue resection guide 66 to aide in gripping the first tissue resection guide 66 during insertion and removal from the second positing block 58.

Spacer Guide

Figure 6:
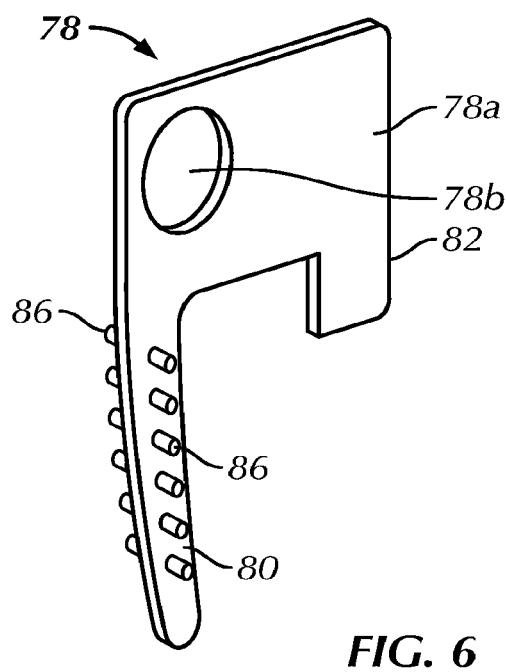
FIG. 6 is a perspective view of a spacer guide in accordance with an exemplary embodiment of the present invention.

Referring to the embodiment of FIG. 6, a spacer guide 78 may be provided for positioning the first and second positioning blocks 50, 58 relative to the attachment block 38 and a feature 12c of the first bone 12 (FIGS. 17-20). Because the attachment block 38 may be attached to the first bone 12 proximate the feature 12c, the spacer guide 78 may be used to adjust the first and second positioning blocks 50, 58 and position the end surface 58e of the second positioning block 58 in the appropriate position. The spacer guide 78 may be used in conjunction with a C-arm or other imaging device to position the end surface 58e of the second positioning block 58 a predetermined distance from the feature 12c of the first bone 12. In one embodiment, the feature 12c is a superior aspect of the tibial plafond of the tibia (see FIG. 20).

The spacer guide 78 may include an extension arm 80 extending downwardly from a body 78a of the spacer guide 78. In one embodiment, the extension arm 80 is curved inwardly toward the body 78a during use of the spacer guide 78 such that the extension arm 80 curves around the outside of the patient's anatomy, e.g. leg 84. However, the extension arm 80 may be straight or outwardly curved and have any shape.

The spacer guide 78 may include a projection or mount 82 extending downwardly from the body 78a and spaced laterally from the extension arm 80. The mount 82 may be configured to snugly fit within the slot 70a of the first guide path 70. The body 78a optionally includes a grip 78b such as an aperture extending through the body 78a to aid in grasping the spacer guide 78 between two fingers. The extension arm 80, the body 78a and the mount 82 may be generally planar and parallel to one another.

The extension arm 78 may include one or more projections 86 extending from the extension arm 80 and spaced a predetermined distance from the mount 82 in order to measure the distance from the slot 70a of the first guide path 70. In one embodiment, the projections 86 are pins. The projections 86 may extend through the extension arm 80 such that the projections 86 extend from either side of the extension arm 78 allowing the spacer guide 78 to be used on either lateral side of the ankle 24. In one embodiment, the predetermined distance, i.e. the length of each projection from each side of the extension arm 80 is approximately 1 mm to approximately 10 mm. In one embodiment, the projections 86 extend approximately 5 mm from the extension arm 80. In one embodiment, there are 6-8 projections 86. However, their may be any number of projections 86 having any configuration. The projections 86 may each include a plurality of distance markings such as ribs or include projections 86 having different lengths so that multiple predetermined distances can be ascertained using a single spacer guide 78. Alternatively, the extension arm 80 and/or body 78a may be curved or spaced from the mount 82 in the normal direction from the body 78a such that the extension arm 80 is spaced from the mount 82 the predetermined distance in the normal direction from the body 78a without the need for projections 86. The extension arm 80 may alternatively be adjustable relative to the mount 82 such that the predetermined distance may be altered by adjusting a feature or adjusting the orientation of the extension arm 80 relative to the body 78a. The extension arm 80 may alternatively have a thickness equal to the predetermined distance from the mount 82 for measuring the predetermined distance.

Second Tissue Resection Guide

Figure 7:
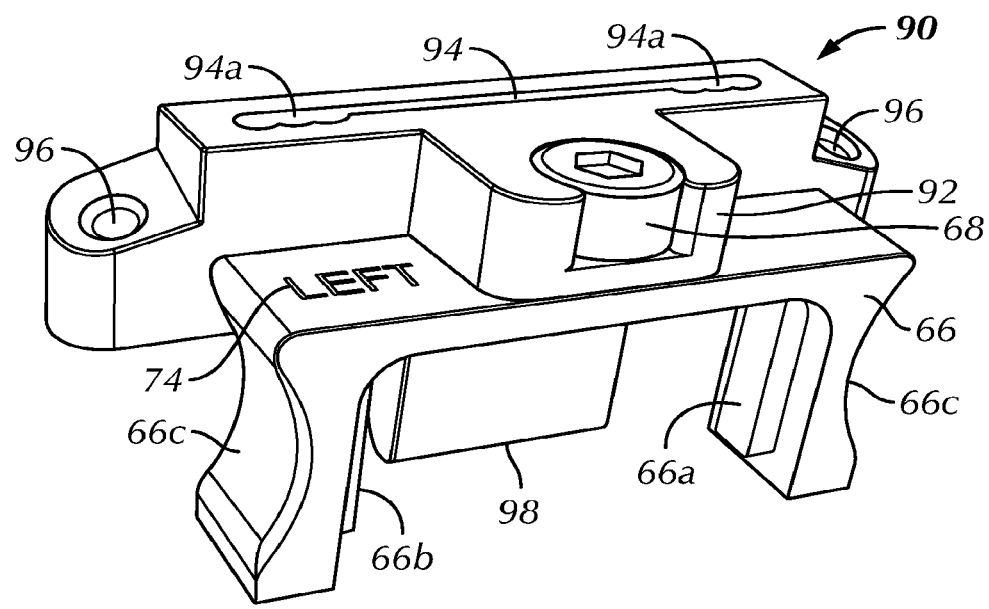
FIG. 7 is a perspective view of a second tissue resection guide in accordance with an exemplary embodiment of the present invention.
Figure 21:
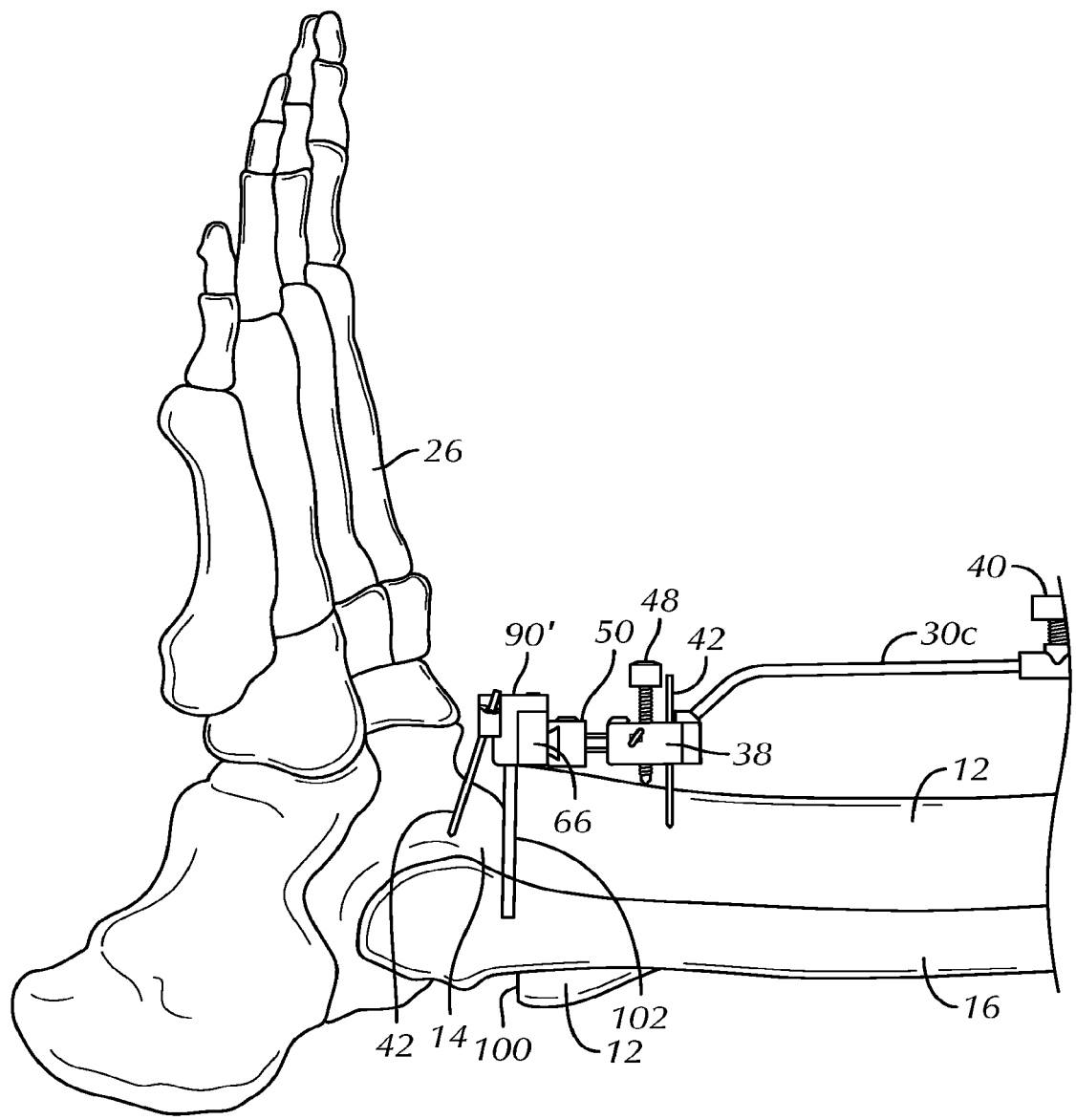
FIG. 21 is a side view of the alignment guide shown if FIG. 4 with the second tissue resection guide of FIG. 8 attached to the alignment guide and the second bone.

Referring to the embodiment of FIG. 7, a second tissue resection guide 90 may be provided to resect tissue from the second bone 14 using, for example, the first tissue resection tool (not shown). The second tissue resection guide 90 may be mounted to the second bone 14 relative to the placement of the attachment block 38. In one embodiment, the second tissue resection guide 90 is configured to mount over the first tissue resection guide 66 such that the second bone 14 is resected relative to the first resected tissue surface 100 (FIG. 21). The second tissue resection guide 90 may include a mount 92 for securing the second tissue resection guide 90 to first tissue resection guide 66. The mount 92 may be configured to receive the fastener 68 used to secure the first tissue resection guide 66 to the second positioning block 58.

In one embodiment, a tab 98 extends downwardly from the second tissue resection guide 90 to contact the first bone 12. The tab 98 may contact the first resected tissue surface 100 of the first bone 12 to help stabilize the second tissue resection guide 90 relative to the first bone 12. In an alternative embodiment of the second tissue resection guide 90, the second tissue resection guide 90 includes an integral component that is shaped and configured similar to the first tissue resection guide 66 such that after using the first tissue resection guide 90, the first tissue resection guide 66 is removed from the second positioning block 58 and the second tissue resection guide 90 with the integral first tissue resection guide 66 is mountable directly to the second positioning block 58.

The second tissue resection guide 90 may include a guide path 94 for guiding and capturing a tissue resection tool such as the first tissue resection tool, e.g. a blade (not shown). The second tissue resection guide 90 may be configured to guide a tissue resection tool that is different or the same from the tissue resection tool used with the first tissue resection guide 66. The first tissue resection tool may be used with the second tissue resection guide 90 to expose a resected or second surface 104 (see FIG. 22) of the second bone 14. In one embodiment, the second resected tissue surface 104 is bone. In alternative embodiments, the second resected tissue surface 104 is another tissue such as cartilage and/or a combination of different tissue.

In one embodiment, the second tissue resection guide 90 may be configured such that one side of the guide path 94 is generally flush or parallel with an outer end 66d (FIG. 5) of the first tissue resection guide 66 such that the guide path 94 and the outer end 66d of the first tissue resection guide 66 define a resection plane. In one embodiment, the first and second tissue resection guides 66, 90 are configured so that when engaged with each other, the guide path 94 is spaced from the slot 70a of the first guide path 70 a predetermined distance. In one embodiment, the predetermined distance between the guide path 94 and the slot 70a of the first guide path 70 is approximately 1 mm to approximately 8 mm. In one embodiment, the predetermined distance between the guide path 94 and the slot 70a of the first guide path 70 is approximately 4 mm. The predetermined distance between the guide path 94 and the slot 70a of the first guide path 70 may be generally equal to the thickness of the first guide path 70. The guide path 94 may include one or more recesses 94a each for receiving pins (not shown) to adjust the length of the guide path 94 and limit the amount that the second bone 14 is resected.

The second tissue resection guide 90 may include one or more pin mounts 96. The pin mounts 96 may be used to support pins 42 that secure the second tissue resection guide 90 to the second bone 14 (see FIG. 20). In such an embodiment, the second bone 14 is held relative to the attachment block 38. In an alternative embodiment, the guide path 94 may include a generally open side such that the first tissue resection tool is only supported or guided on one side.

Figure 8:
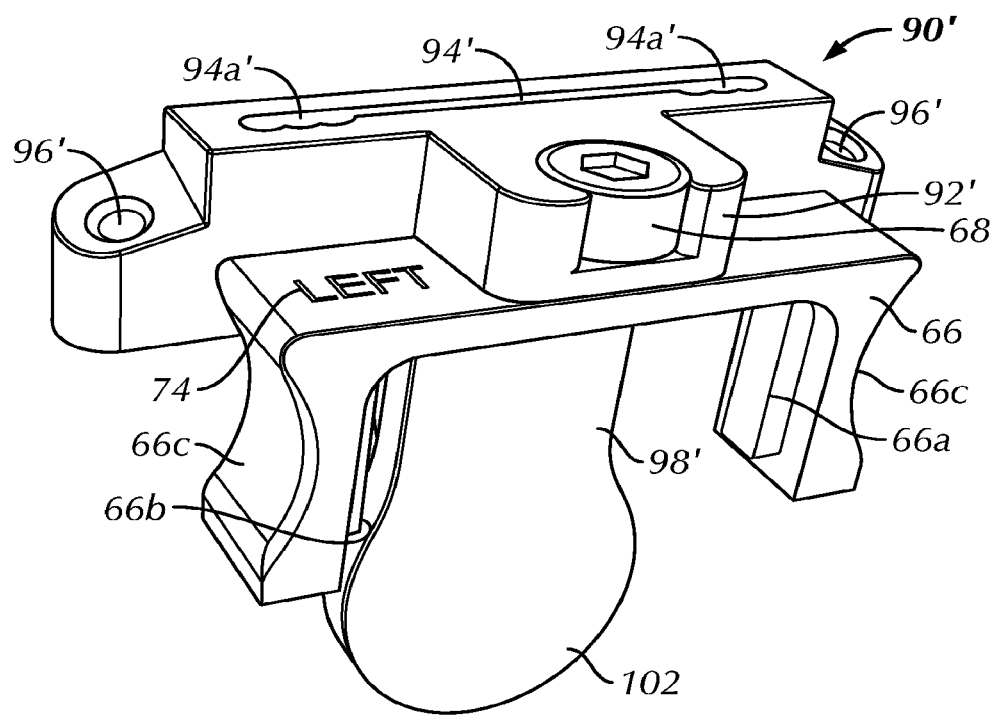
FIG. 8 is a perspective view of the second tissue resection guide shown in FIG. 7 having a tab extension.

Referring to the embodiment of FIG. 8, a second tissue resection guide 90' may include a tab extension 102 that extends further downwardly from the tab 98' such that the tab extension 102 is sandwiched between and contacts both the first resected tissue surface 100 and the not yet resected second bone 14 when initially in place on the first tissue resection guide 66 (see FIG. 21). In one embodiment, the second tissue resection guide 90 is used for normal to tight joints and the second tissue resection guide 90' with the tab extension 102 is used for lax joints. In one embodiment, the tab extensions 102 are approximately 1 mm to approximately 10 mm thick depending on how lax the joint is. In one embodiment, the second tissue resection guides 94' are provided with tab extensions 102 in approximately 2 mm, 4 mm or 6 mm thicknesses. In one embodiment, the tab extension 102 is generally flat and bulbous shaped such that the tab extension 102 sufficiently contacts the first resected tissue surface 100. However, the tab extension 102 may be any shape such as rectangular, triangular or square.

Datum

Figure 9A:
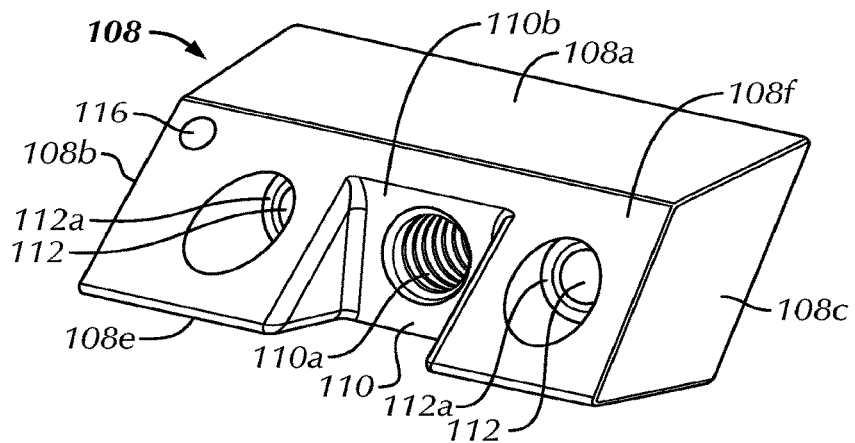
FIG. 9A is a perspective view of a datum in accordance with an exemplary embodiment of the present invention.
Figure 9B:
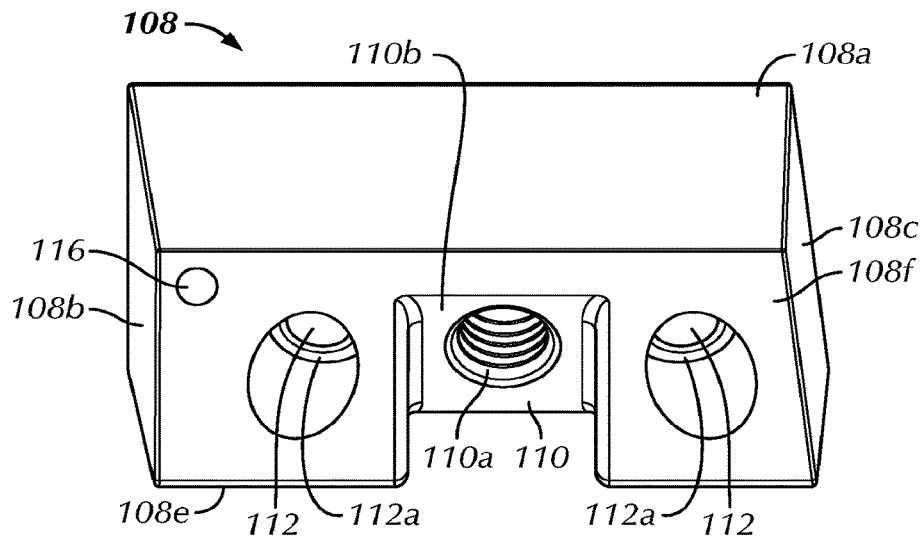
FIG. 9B is a top plan view of the datum shown in FIG. 9A.
Figure 9C:
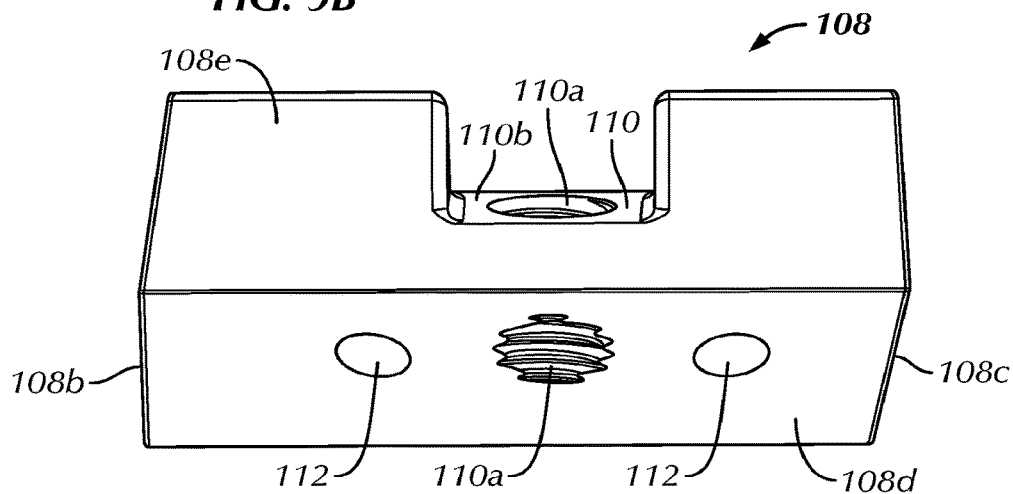
FIG. 9C is a bottom perspective front view of the datum shown in FIG. 9A.

Referring to the embodiment of FIG. 9A-9C, a datum 108 may be provided for releasably engaging at least one tissue resection guide as described further below. The datum 108 may provide a fixed reference point on the second bone 14 to make one or more resections to the second bone 14 relative or in reference to the datum 108. The datum 108 may also include one or more surfaces and/or one or more edges that are aligned with a feature of the tissue resection guide (e.g. a guide path) to form a resection plane an example of which is described in more detail below. The datum 108 may assist in directly guiding and supporting the various resection tools. In one embodiment, the datum 108 allows for multiple resections adjacent to the datum using two or more resections guides while only attaching one device to the second bone 14, e.g, the datum 108.

In one embodiment, the datum 108 is a parallelepiped. However, the datum 108 may be generally shaped and sized such that resections guided at least partially by the datum 108 conform to an upper interior (not shown) of the first endoprosthetic component 18. Though the datum 108 may have planar sides, the datum 108 may alternatively have one or more curved or stepped sides. The shape of the datum 108 may generally correspond to the shape required to fully resect an end of the second bone 14 using a predetermined number of generally planar resection planes. In one embodiment, the datum 108 includes four generally planar resection planes. The use of the datum 108 may help to minimize the amount of tissue that is resected from the second bone 14 by reducing recutting, reshaping and over resection caused by free-hand cutting, miss-measurements, measuring off of other cuts and/or misplacement of resection guides.

In one embodiment, the datum 108 includes first, second, third and forth sides 108a, 108b, 108c, 108e. In one embodiment, a bottom 108d of the datum 108 is sized and configured to contact a tissue surface (e.g., the second resected tissue surface 104). In one embodiment, the datum 108 has at least one side (e.g., one of sides 108a, 108b, 108c, 108e) that is generally in-line or parallel to a resected tissue surface such as a tissue surface (e.g. one of surfaces 104a, 104b, 104c, 104d) such as in a manner described below after the resections to the second bone 14 are made. The first second and third sides 108a, 108b, 108c of the datum 108 may each be angled inwardly such that they each extend at an acute angle from the base or bottom 108d (FIG. 9C). In one embodiment, the top of the fourth side 108e may extend outwardly such that the fourth side 108e extends at an obtuse angle from the bottom 108d. The second and third sides 108b, 108c may be angled inwardly toward each other proximate the first side 108a about an axis perpendicular to the bottom 108d such that the second and third sides 108b, 108c each extend from the fourth side 108e at an acute angle measured on a plane parallel to the bottom 108d. In one embodiment, the first side 108a is generally ninety degrees from the fourth side 108e as measured on a plane parallel to the bottom 108d. In one embodiment, the third side 108c is angled inwardly proximate the first side 108a about an axis perpendicular to the bottom 108d. An angle of inclination defined by the intersection of the third side 108c and a plane normal to the bottom 108d may be greater than an angle of inclination defined by the intersection of the second side 108b and a plane normal to the bottom 108d as illustrated in FIG. 9B. At least one side 108a, 108b, 108c, 108e of the datum 108 may be sized and configured to at least partially contact and guide a tissue resection tool as described further below. In one embodiment, the first, second, third and fourth sides 108a, 108b, 108c, 108e of the datum 108 are posterior, medial, lateral and anterior sides respectively.

The datum 108 optionally includes a datum mount 110. The datum mount 110 may include a threaded aperture 110a. The datum mount 110 may include a recessed section 110b for further engaging at least one tissue resection guide and for receiving a datum securement 122 of a distractor 120 (see, e.g., FIG. 10D). The recessed section 110b may have a generally cube-like shape. However, the recessed section 110b may have any shape such as pyramid, spherical-like or approximations thereof.

Figure 25:
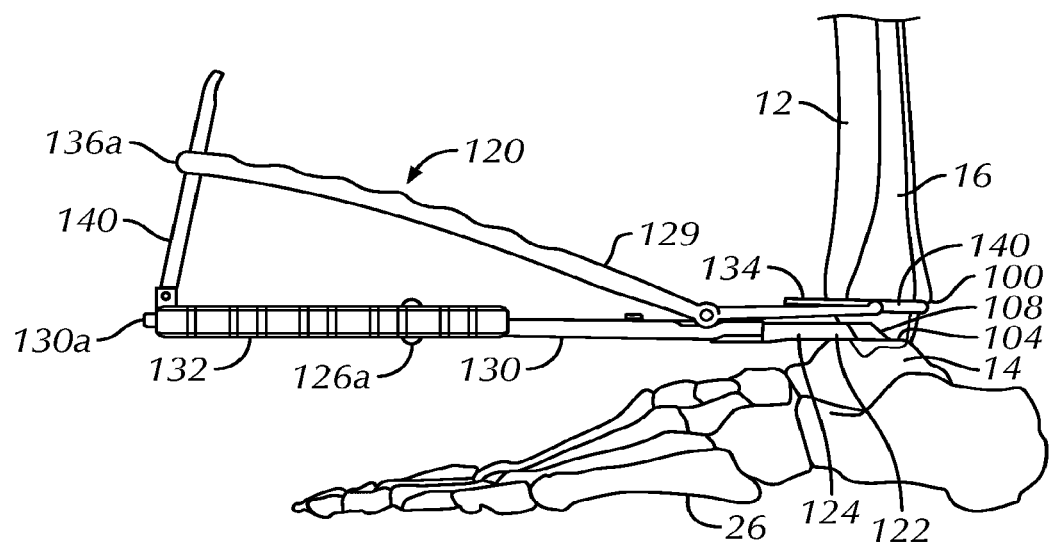
FIG. 25 is a perspective view of the distractor shown in FIG. 10A in the distracted position.

The datum 108 may include at least one pin aperture 112 for receiving a pin 42 or a shoulder pin 114. The pin aperture 112 may include a shoulder 112a to limit depth of the shoulder pins 114 (FIG. 25). The pins 114 may be received at an angle relative to the bottom 108d such that the pins 114 extend upwardly from the datum 108 toward the fourth side 108e of the datum 108. In one embodiment, the datum 114 includes a pair of pin apertures 120 spaced on medial/lateral sides of the datum mount 110 such that when pinned to the second resected tissue surface 104, the datum 108 does not rotate relative to the second resected tissue surface 104.

The datum 108 may include indicia 116 such as a colored polymeric plug that indicates the size and/or shape of the datum 108. In one embodiment, the indicia 116 is positioned on a non-tissue contacting surface. In one embodiment, the indicia 116 is located on a surface opposite a surface that is a tissue contacting surface such as, for example, the bottom 108 in the embodiment illustrated in FIG. 9C.

Distractor

Figure 10B:
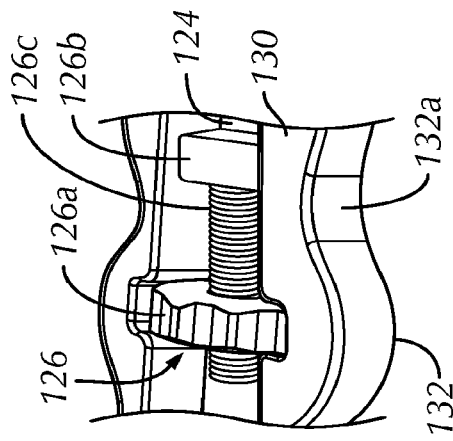
FIG. 10B is an enlarged view of a datum lock of the distractor shown in FIG. 10A.
Figure 10A:
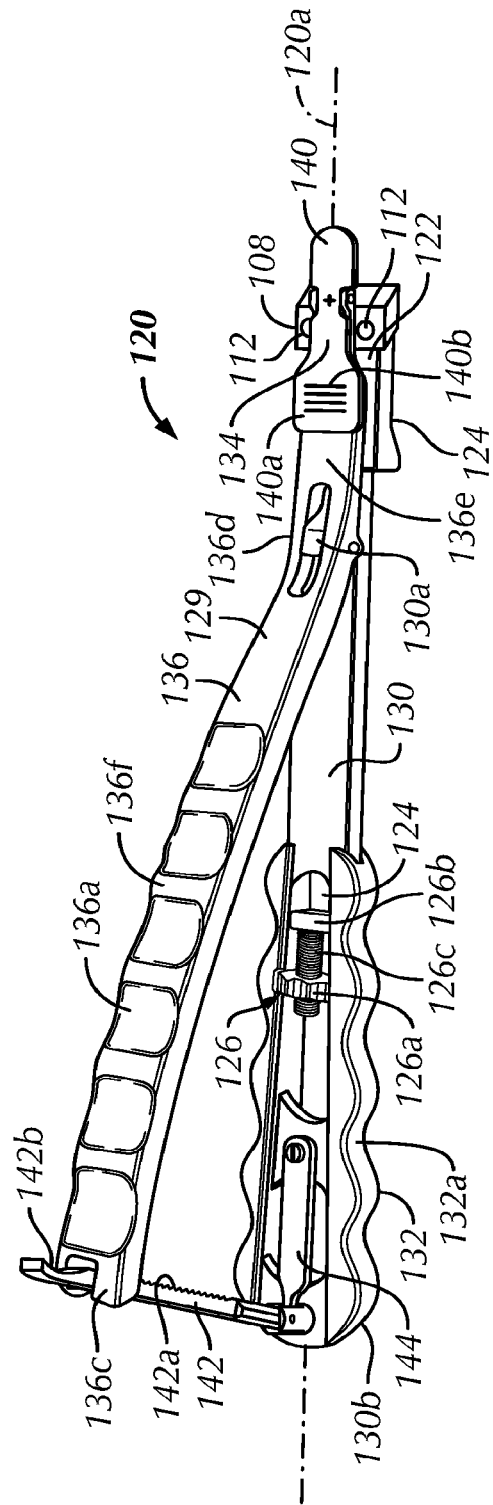
FIG. 10A is a perspective view of a distractor in accordance with an exemplary embodiment of the present invention shown in an insertion position and securing the datum of FIG. 9A.
Figure 10C:
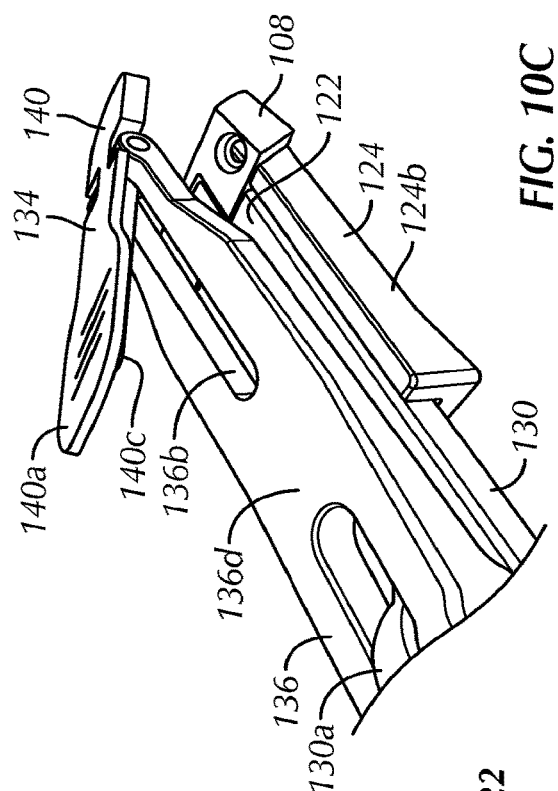
FIG. 10C an enlarged top view of a paddle of the distractor shown in FIG. 10A being pivoted for demonstrative purposes.

FIGS. 10A-10C illustrates one embodiment of a distractor 120. The distractor 120 may be sized and configured to place, orient and/or insert the datum 108 onto a tissue surface, e.g. the second resected tissue surface 104. The distractor 120 may additionally be used to distract or separate the first resected tissue surface 100 from the second resected tissue surface 104 and provide sufficient space to place the datum 108 and attach resection guides thereto. The distractor 120 may include a handle 129 and a datum securement 122 and a tissue engaging portion 134 attached to the handle 129. At least a portion of the handle 129 may extend along a handle axis 120a. In one embodiment, the handle 129 includes a first or lower handle 130 and a second or upper handle 136.

Figure 24:
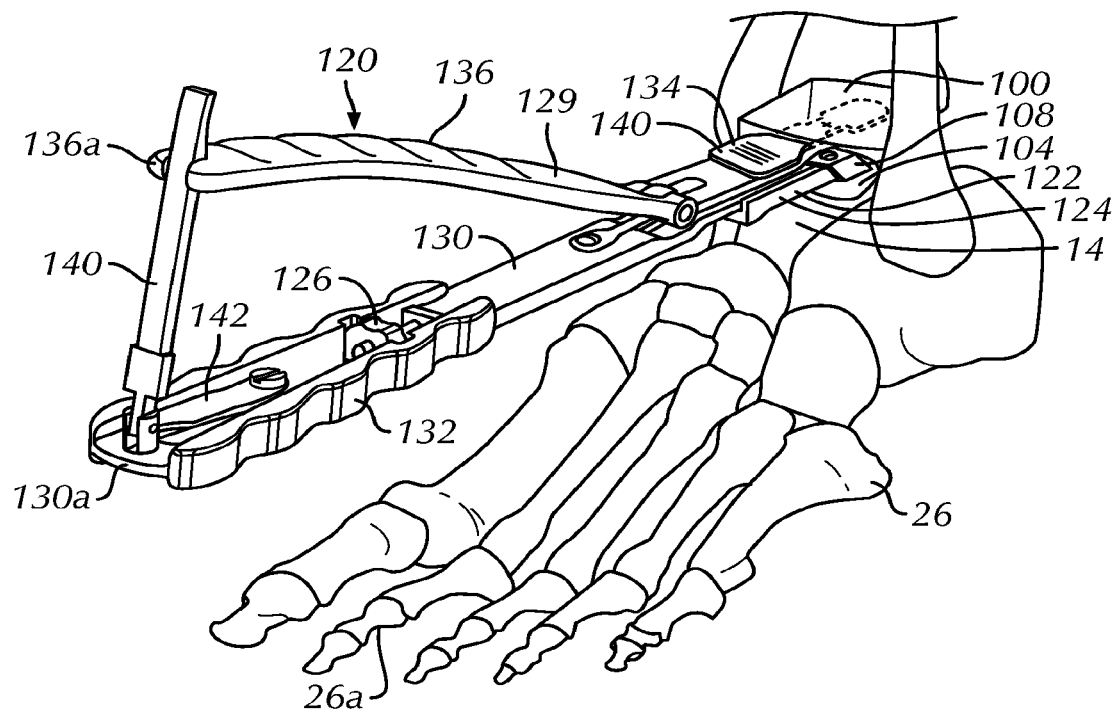
FIG. 24 is a perspective view of the distractor shown in FIG. 10A in the insertion position.

The datum securement 122 may be configured to releasably engage the datum 108. The datum securement 122 may releasably engage the datum 108 in an insertion position (FIG. 10A) and or during positioning of the datum 108 on the second resected tissue surface 104 (FIGS. 24 and 25). In one embodiment, the datum securement 122 includes at least one projection 122a. The projection 122a may be oriented to project from the datum securement 122 at an angle relative to the axis 120a. Projections 122a may be sized, configured and oriented to extend into the datum mount 110 of the datum 108. However, the datum securement 122 may include any suitable device for releasably engaging or securing the datum 108 such as a threaded attachment or a magnet.

In one embodiment, the distractor 120 includes an abutment member 124 proximate the datum securement 122. The abutment member 124 may be fork shaped such that the datum 108 is engaged by ends 124a on either sides of the projection 122a to provide at least three points of contact with the datum 108 such that the datum 108 is securely held and does not move relative to the distractor 120. However, the abutment member 124 may have any suitable shape including one or more surface or point of contact end 124a. The ends 124a of the abutment member 124 may be slanted or otherwise shaped and configured to be generally parallel to the fourth side 108e of the datum 108. The abutment member 124 may be slidable relative to a lower handle 130 extending from the datum securement 122. The abutment member 124 may be slid toward the datum projection 122a to pinch the datum 108 between the datum projection 122a and the abutment member 124. Alternatively, the datum projection 122a may be moved relative to the abutment member 124. The abutment member 124 may have a recessed or stepped distal bottom surface 124b (FIG. 10D) such that the abutment member 124 is generally flush or parallel with the bottom surface 108d of the datum 108. The remainder of the abutment member 124 may be thicker than the distal bottom surface 124b to strengthen the abutment member 124.

In one embodiment, the abutment member 124 includes a datum lock 126 configured to move the datum datum securement 124 from a secured position to a released position. The datum lock 126 may include a rotatable nut 126a that threadably engages a shaft 124c. In one embodiment, the shaft 126c is integral with the abutment member 124. In an alternative embodiment, the shaft 124c is integral with the nut 126a and the threaded shaft 124c extends into the abutment member 124. The datum securement 122 may include a stop 128 (FIG. 10E) that engages with the abutment member 124 when the datum 108 has been secured with the distractor 120 to prevent over extending the abutment member 124 and exerting a pinching force on the datum 108 that may damage the datum projection 122a and/or the datum 108.

In one embodiment, the lower handle 130 extends from the datum securement 122. The lower handle may be generally aligned with the handle axis 120a. The lower handle 130 may include a grip 132. In one embodiment, the grip 132 is integral with the lower handle 128 and may include a plurality of indentations 132a. Alternatively, the grip 132 may be a separate component and/or have a textured surface.

The distractor 122 may include a tissue engaging portion 134. In one embodiment, the upper handle 136 extends from the tissue engaging portion 134. The upper handle 136 may include a distal portion 136e attached to the tissue engaging portion 134 and a grip portion 136f attached to the distal portion 136e. The grip portion 136f of the upper handle 136 may include a plurality of grips 136a. In one embodiment, the grips 136a include a plurality indentations 136a separated by columns that are oriented perpendicular to a longitudinal axis 120a of the handle 130. The grips 136a may have any suitable shape such as scalloped or cylindrical.

The distal portion 136e and the grip portion 136f may be joined at an inflection or pivot point 136d. In one embodiment, the grip portion 136f of the upper handle 136 extends from the inflection point 136f at an angle relative to the lower handle 130 as shown in FIG. 10A. The distal portion 136e may be generally parallel with the axis 120a in an insertion position. The upper handle 136 may extend from the inflection point between a range of angles that allows a user to grip the upper and lower handles 136, 130 with one hand while allowing sufficient movement of the tissue engaging portion 134 relative to the datum 108. In one embodiment, the upper handle 136 may extend from the inflection point at approximately 30 degrees as shown in FIG. 10A. The upper handle 136 may be convexly shaped away from the lower handle 130 so as to make the upper handle 136 closer to being parallel with the lower handle 130 to make gripping of the distractor 120 easier. In one embodiment, the upper handle 136 is pivotable with respect to the lower handle 130 such that squeezing the upper and lower handles 130, 136 together spaces the tissue engaging portion 134 from the datum securement 122. In one embodiment, the lower handle 130 is releasably attached to the upper handle 136. The lower handle 130 may include a socket 130a that rotatably supports an axle (not visible) on the upper handle 136. In one embodiment, the socket 130a is partially open, e.g. C-shaped, such that the upper handle 136 is removable proximally from the lower handle 130. The axle of the upper handle 136 may be spring biased within the socket 130a by a first biasing member 138. The first biasing member 138 may be a cantilever spring. In an alternative embodiment, the lower and upper handles 130, 136 have a scissor orientation such that the lower handle 130 extends from the tissue engaging portion 134 and the upper handle 136 extends from the datum securement 122.

In one embodiment, the tissue engaging portion 134 includes a paddle 140 configured to engage the first resected tissue surface 100. The paddle 140 may be pivotably attached to the upper handle 136 such that the paddle 140 remains at a generally constant angle during separation of the first and second bones 12, 14 to maintain contact with the first resected tissue surface 100 during distraction of the first and second bones 12, 14. In one embodiment, the paddle 140 may remain generally parallel to the second resected tissue surface 100 as the tissue engaging portion 134 is pivoted from the datum securement 122. The paddle 140 and upper handle 136 may be pivotable about axes that are generally parallel to one another.

In one embodiment, a portion of the paddle 140 may be at least partially narrower than the space between the pin apertures 112 of the datum 108 such that the paddle 140 can be slid out between the shoulder pins 114 after securing the datum 108 to the second resected tissue surface 104. In one embodiment, the paddle 140 includes an enlarged end 140a. In one embodiment, the enlarged end 140a is wider than the space between the pin apertures 112 of the datum 108 to provide, for example, increased surface area for contacting the first resected tissue surface 100 and keeping surrounding tissue clear from the second resected tissue surface 104. The paddle 140 may also be enlarged toward the enlarged end 140a to provide more weight proximal to the axis of rotation such that paddle 140 tends to lay parallel with the extending upper handle 136 when released. The paddle 140 may be partially recessed within the extending upper handle 136 such that the paddle 140 is nearly flush and/or parallel with the upper handle 136 in the insertion position. In one embodiment, the paddle 140 may include one or more ribs 140c (FIG. 10C) that extends downwardly from the paddle 140 into a recess 136b of the upper handle in the insertion position. In one embodiment, the ribs 140c may be provided to generally stiffen and minimize bending of the enlarged end 140a while allowing the paddle 140 to be generally flush or parallel with the upper handle 136.

The proximal ends 136c, 130b of the upper and lower handles 136, 130 may be connected by a ratchet 142 such that distractor 120 can be held in a distracted position (FIG. 25) without a user having to continually squeeze the handles 130, 136. The ratchet 142 may include a plurality of teeth 142a that engage a projection (not shown) of the upper handle 136 and prevent the upper handle 136 from returning to the insertion position. The ratchet 140 may be spring biased via a second biasing member 144. In one embodiment, the second biasing member 144 is a cantilever spring secured to the lower handle 130.

Figure 10D:
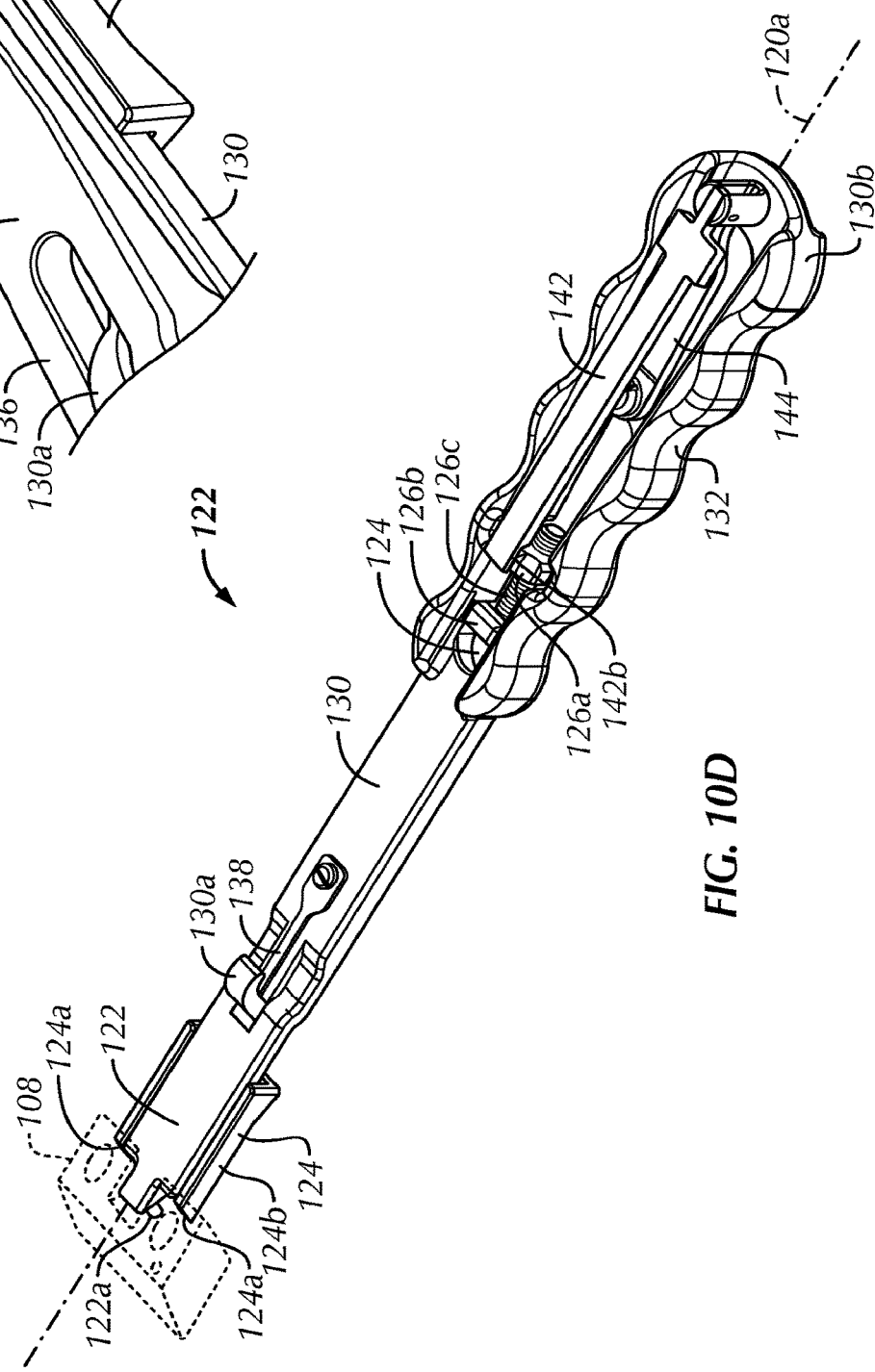
FIG. 10D a perspective view of the distractor shown in FIG. 10A with the upper handle removed, the ratchet pivoted downwardly and the datum shown in phantom.
Figure 10E:
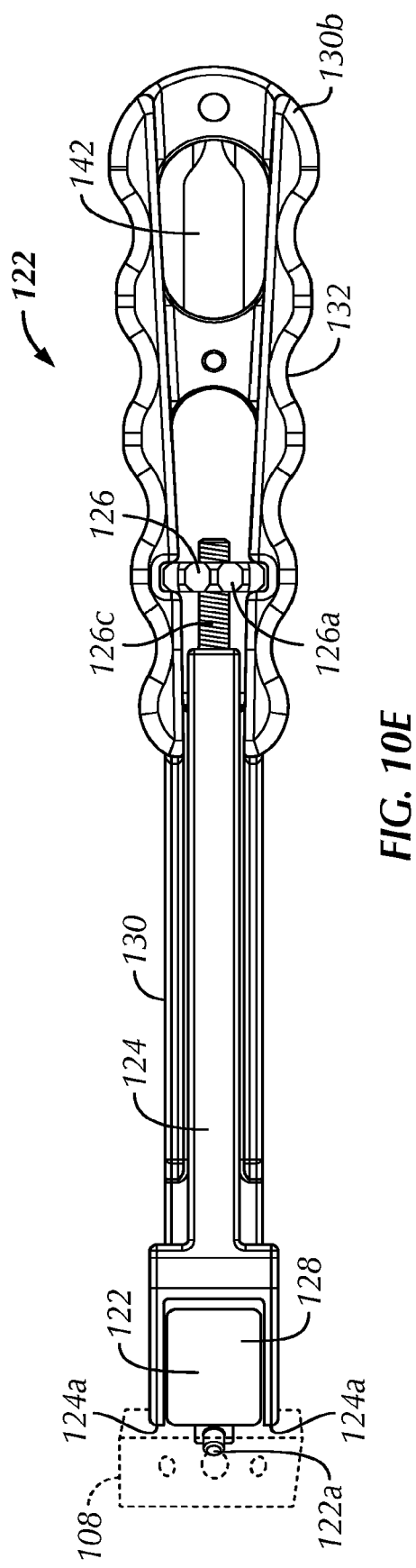
FIG. 10E is a bottom plan view of the distractor shown in FIG. 10D.

In one embodiment, the upper handle 136 may be removed from the lower handle 130 if distraction of the first and second resected tissue surfaces 100, 104 is not necessary (e.g. for a lax joint) and/or to disengage and the ratchet 142 such that the upper handle 136 is freely pivotable relative to the lower handle 130. The ratchet 142 may be disengaged from the upper handle 136 by pulling back on the ratchet, removing the upper handle 136 from the lower handle 130 and pivoting the ratchet 142 downwardly so that it lies on the lower handle 130 (FIG. 10D). Once the ratchet 142 has been disengaged from the upper handle 136, the upper handle 136 re-attached to the lower handle 130 such that the distractor 120 functions without the ratchet 142. The ratchet 142 optionally includes a grip 142b that extends upwardly past or through the upper handle 136 such that the ratchet 142 may be gripped and pulled rearwardly or proximally to disengage the ratchet 140 from the upper handle 136. In one embodiment, the grip 142b is an indent. The grip 142b of the ratchet 142 may receive a portion of the datum lock 126 in the folded position (FIG. 10D) such that the ratchet 142b may lie flat against the lower handle 130. Alternatively, the ratchet 142 may have a shorter length than shown such that the datum lock 126 may be used while the ratchet 142 lies against the lower handle portion 130.

Third Tissue Resection Guide

Figure 11A:
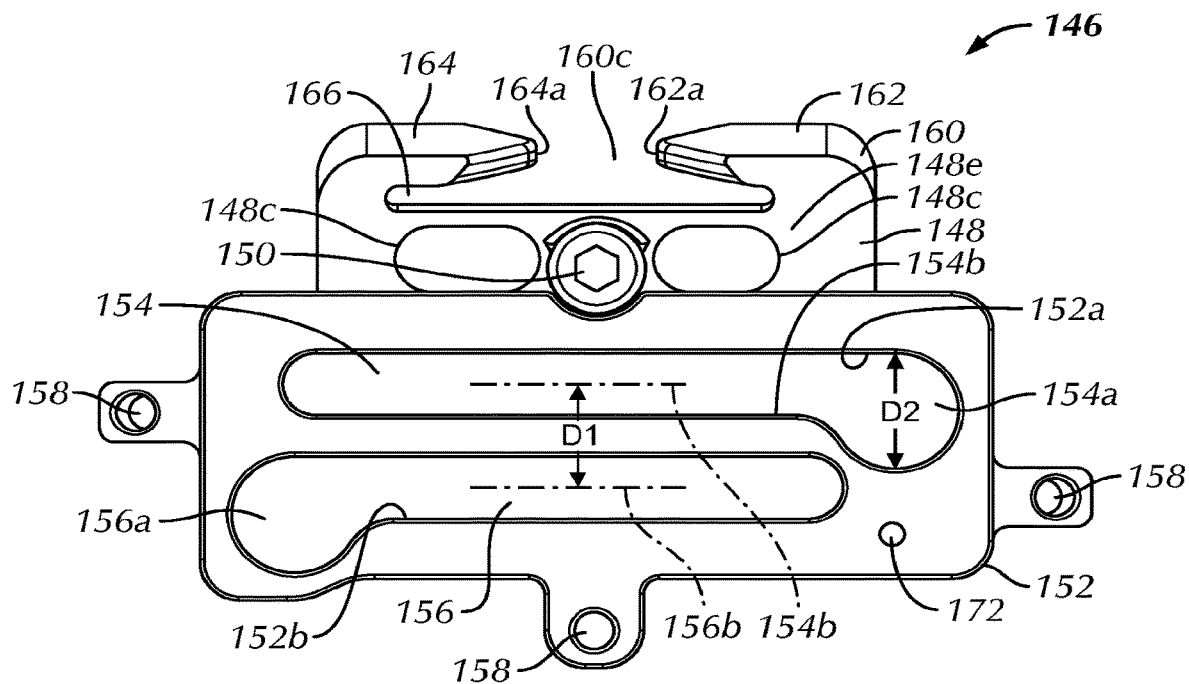
FIG. 11A is a top plan view of a third tissue resection guide in accordance with an exemplary embodiment of the present invention.
Figure 11B:
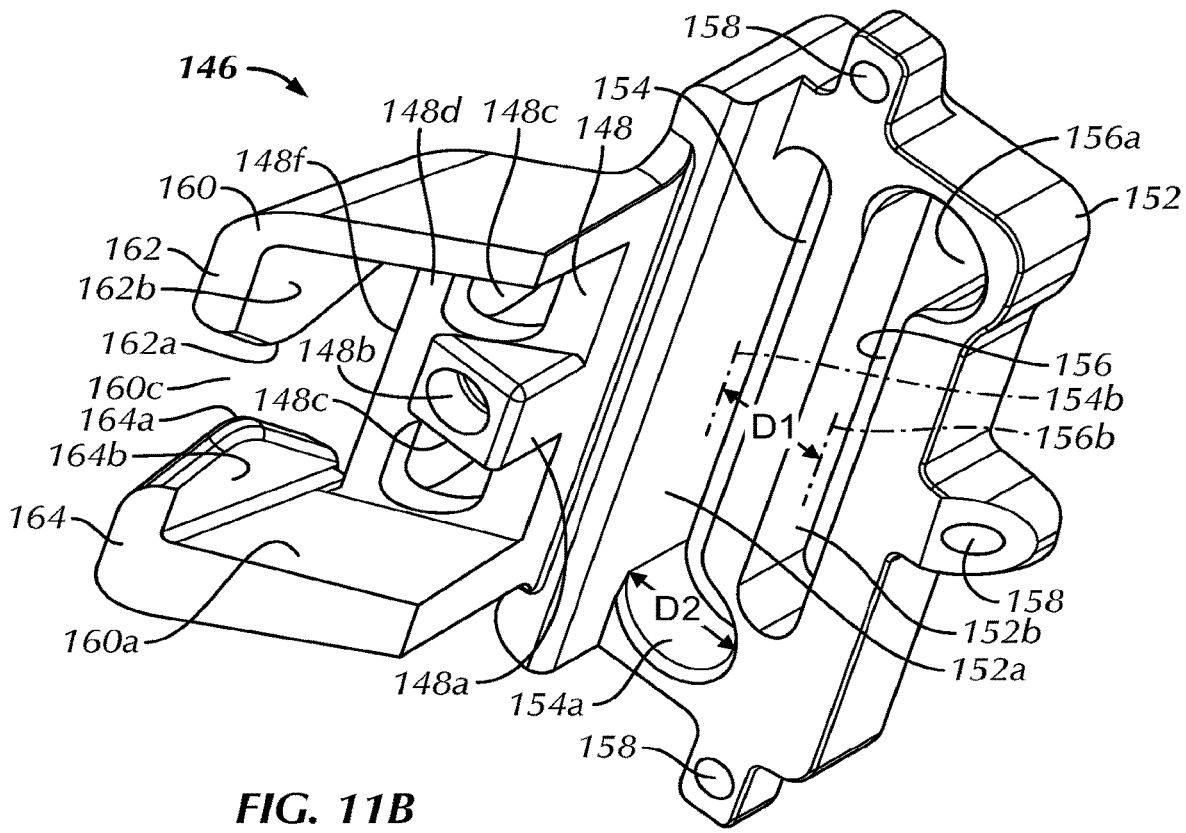
FIG. 11B is a bottom perspective view of the third tissue resection guide shown in FIG. 11A.

Referring to the embodiment of FIGS. 11A-11B, a third tissue resection guide 146 may be provided for resecting, for example, the second bone 14. The third tissue resection guide 146 may be sized and configured to releasably attach to the top side 108f of the datum 108 and guide one or more tissue resection tools. In one embodiment, the third tissue resection guide 146 is an anterior/posterior tissue resection guide for resecting the second bone 14 anterior and posterior to the datum 108. The third tissue resection guide 146 may be used to resect the second bone 14 in any direction relative to the datum 108. The third tissue resection guide 146 includes a base 148 that releasably engages the datum 108. The base 148 may include a datum projection 148a that extends from the base 148 and fits within the recessed section 108d of the datum 108 to prevent the third tissue resection guide 146 from rotating with respect to the datum 108. The datum projection 148a may include an aperture 148b for receiving a fastener 150 configured to secure the third tissue resection guide 146 to the datum 108. In one embodiment, the fastener 150 is an Allen screw. However, the fastener 150 may be any securement device such as a snap. The base 148 may include pin apertures 148c for fitting over the shoulder pins 114 extending from the datum 108. The pin apertures 148c may be angled away from the base 148 such that the pins 42 remain out of the way and provide a more stable support from the second bone 14.

The third tissue resection guide 146 may include a first frame 152 attached to the base 148. In one embodiment, the first frame 152 is integral with the base 148. In one embodiment, the first frame 152 is adjacent to the fourth side 108e of the datum 108 when the third tissue resection guide 146 is engaged with the datum 108 (e.g., FIG. 28).

The first frame 152 may include or define one or more guide paths (e.g., first and second guide paths 154, 156). In one embodiment, guide paths 154, 156 are apertures within a frame (e.g., the first frame 152). In one embodiment, the guide paths 154, 156 are elongate apertures. For example, in one embodiment, the guide paths 154, 156 are defined by an inner wall 152a of a frame (e.g., the first frame 152). In the embodiment of FIG. 11A, for example, the guide paths 154, 156 are defined by a continuous inner wall 152a. In one embodiment, guide paths such as guide path 166 is defined a discontinuous inner wall 160a. Also as illustrated in FIG. 11A, guide paths, such as guide paths 154, 156 may extend through a frame (e.g., first frame 152) such that there is no restriction to a correctly sized tool passing though such a guide path from one side of a frame to another. As will be illustrated in more detail below, a guide path (such as guide path 180c of FIG. 12B may include a closed upper surface 180a to restrict the movement of a resection tool when the resection tool is being guided in the guide path 180c.

Figure 28:
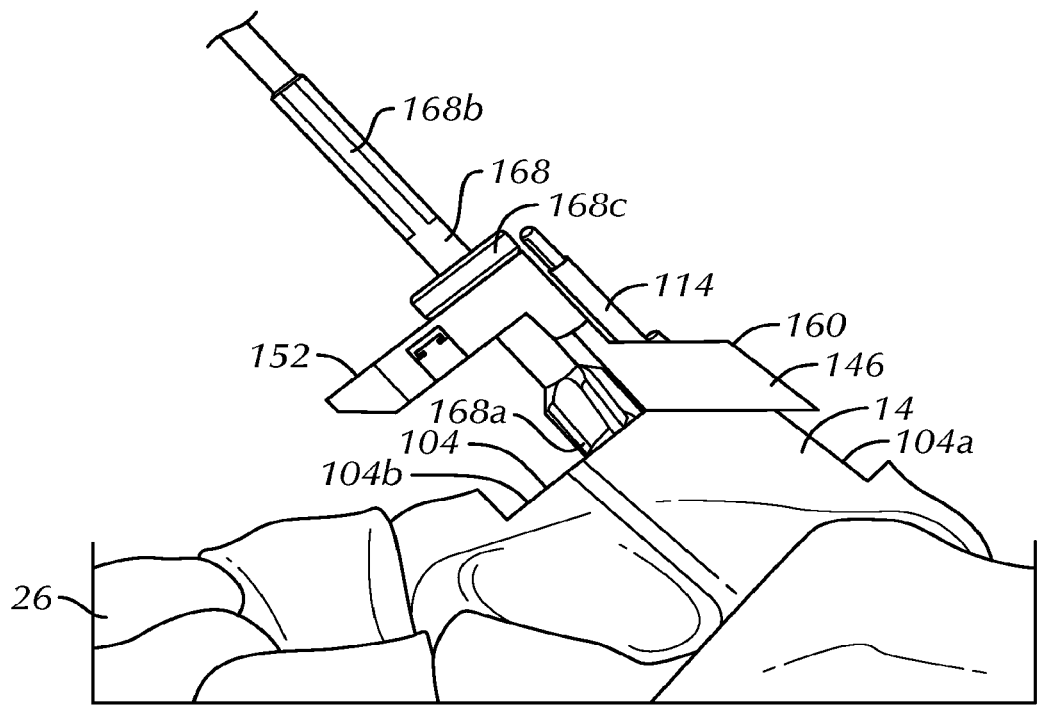
FIG. 28 is a side elevational view of a third tissue resection tool being guided by the third tissue resection guide shown in FIG. 11A.
Figure 29:
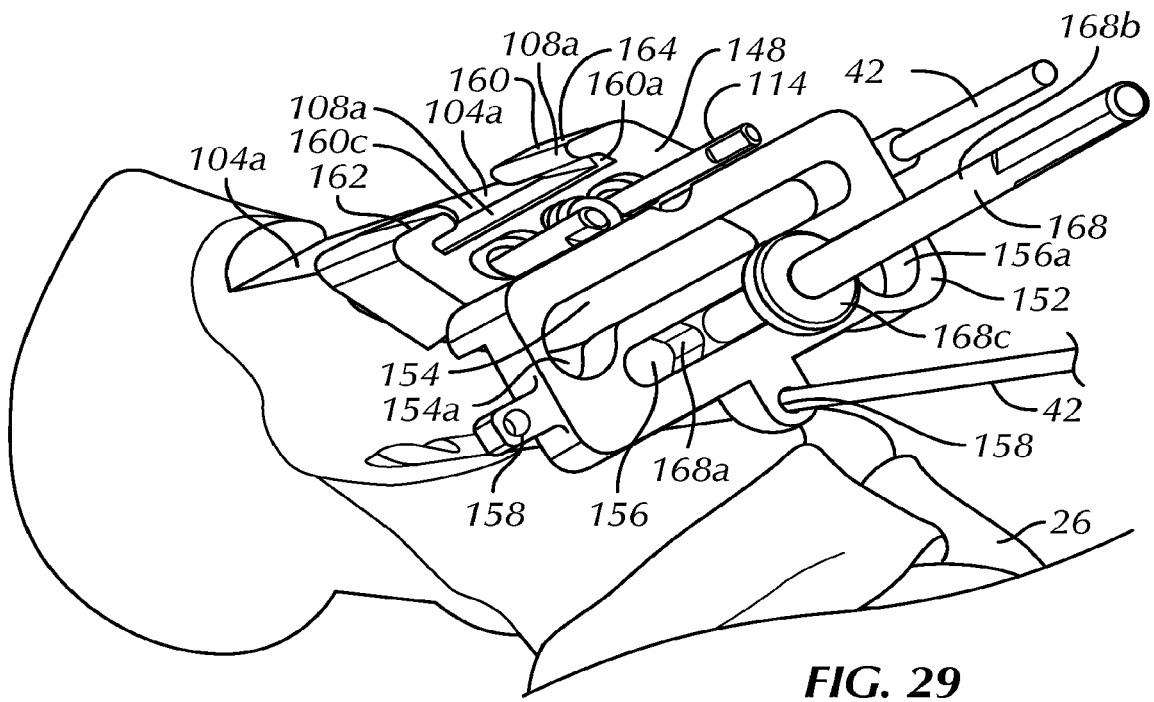
FIG. 29 is a front perspective view of the second tissue resection tool being guided by the third tissue resection guide shown in FIG. 11A.

In one embodiment, the first and second guide paths 154, 156 each include an enlarged end 154a, 156a. The enlarged ends 154a, 156a (e.g., of adjacent guide paths) are optionally on opposite lateral sides of the first frame 152. In one embodiment, the enlarged end 154a of first guide path 154 is proximate the lateral side of the ankle 24 and the enlarged end 156 of the second guide path 156 is proximate the medial side of the ankle 24 during use as shown in the embodiment of FIGS. 28 and 29 such that a resection tool (e.g. a milling bit) 168 spinning clockwise tends to pull away from the base 148 caused by the contact between the resection tool and the second bone 14. In one embodiment, the orientation of the enlarged ends 145a, 156a may be reversed (not shown) for a resection tool 168 spinning in a counterclockwise direction. The first and second guide paths 154, 156 may be generally parallel to each other. The first and second guide paths 154, 156 may be generally parallel to the fourth side 114e of the datum. In one embodiment, the centers 154b, 156b of the first and second guide paths 154, 156 are spaced a distance $D_1$ that is less than a diameter $D_2$ of the enlarged end 154a of the first guide path 154. In one embodiment, the spacing of the guide paths 154, 156 allows for an overlapping resection path as discussed further below. The center 154b of the first guide path 154 may be spaced from the fourth side 108e of the datum 108 a distance approximately equal to half of the diameter $D_2$ of the enlarged end 154a of the first guide path 154 such that the resection path nearly abuts the fourth side 108e of the datum 108. The first frame 152 may include one or more pin supports 158 each configured to receive a pin 42 (see FIG. 27) for further stabilizing the third tissue resection guide 146 relative to the second bone 14.

In one embodiment, each of the first and second guide paths 154, 156 are configured to receive and guide a tissue resection tool such as a second tissue resection tool 168. (See FIG. 27). The second tissue resection tool 168 may be a milling bit though the second tissue resection tool 168 may be any tissue resection tool such as a blade. The second tissue resection tool 168 may include an enlarged cutting head 168a. In one embodiment, the cutting head 168a fits through the enlarged ends 154a, 156a of the first and second guide paths 154, 156 respectively but does not fit through the remainder of the first and second guide paths 154, 156. The remainder of the first and second guide paths 154, 156 may be narrowed from the enlarged ends 154a, 156a to more closely fit another feature of a resection tool such as the diameter of a shaft 168b of the second tissue resection tool 168.

In one embodiment, the second tissue resection tool 168 includes a stop 168c that abuts a top surface of the first frame 152 to limit the distance the second tissue resection tool 168 extends through the first frame 152 as shown in FIG. 28. In one embodiment, the stop 168c is rotatable with respect to the shaft 168b thereby significantly reducing the amount that the stop 168c rotates against and wears the top surface of the first frame 152.

The third tissue resection guide 146 is sized and configured to guide the second tissue resection tool 168 proximate the fourth side 108e of the datum 108. In one embodiment, third tissue resection guide 146 is sized and configured to guide the second tissue resection tool 168 to resect the second bone 14 and to further expose the second resected tissue surface 104 in a direction away from the fourth side 108e of the datum 108. In one embodiment, the further exposed second resected tissue surface 104 is a second resected tissue surface expansion 104b (best illustrated in FIGS. 30 and 33). In one embodiment, the second resected tissue surface 104 is expanded in the anterior direction. The fourth resected tissue surface 104b may be generally normal to the fourth side 108e of the datum 108. In one embodiment, each guide path 154, 156 is used to expose the fourth resected tissue surface 104b. (See FIGS. 28 and 29). The first and second guide paths 154, 156 may be configured to allow for overlapping resections by the second tissue resection tool 168 such that the first and second guide paths 154, 156 create a planar fourth resected tissue surface 104b (See FIGS. 28 and 30). Alternatively, the first frame 152 includes a single guide path 154 or more than two guide paths 154, 156.

With continued reference to the embodiment shown in FIGS. 11A and 11B, the third tissue resection guide 146 optionally includes a second frame 160 adjacent to the first side 108a of the datum 108. The third tissue resection guide 146 may be sized and configured to receive and guide a third tissue resection tool 170. The third tissue resection tool 170 may further expose or expand the second resected tissue surface 104 in a direction away from the datum 108. (See FIG. 26). In one embodiment, the further exposed second resected tissue surface 104 is a third resected tissue surface 104a (best illustrated in FIGS. 30 and 33). Referring to the embodiment of FIG. 27, the third tissue resection tool 170 may be a blade with a cutting end 170a. The third tissue resection tool 170 is configured to slide back and forth within the guide path 166 such that the cutting end 170a resects tissue and expands the second resected tissue surface 104 to further expose the third resected tissue surface 104a.

The second frame 160 may include a guide path 166. In one embodiment, the guide path 166 includes a partially open sidewall 160c defined by sidewall segments 162, 164. In one embodiment, each sidewall 162, 164 extends from the base 148 and wraps around toward each other to define the guide path 166. Sidewall 162, 164 may taper to a center point 162a, 164a. In one embodiment, a benefit of an at least partially open sidewall 160c includes permitting a user to view a tissue resection tool within the guide path 166. In one embodiment, the partially open sidewall 160c permits viewing of the third tissue resection tool 170 and/or the third resected tissue surface 104a (FIG. 27) while the third tissue resection tool 170 is resecting tissue.

In one embodiment, a guide path 166 is defined by inner walls 162b, 164b. In one embodiment, a first side 108a of the datum 108 and a feature (e.g. an edge 148f) of the base 148 are aligned with at least one inner wall of the frame 160 when the third tissue resection guide 146 is engaged with the datum 108.

In one embodiment, the guide path 166 may be generally aligned in a plane with the first side 108a of the datum 108 when the third tissue resection guide 146 is engaged with the datum. For example, in FIGS. 27 and 29, the third tissue resection guide 146 and datum 108 may define a template or resection plane that is aligned with the third resected tissue surface 104a and in which the third tissue resection tool 170 is moved along. In one embodiment, the resection plane corresponds to a desired cut surface of a bone to match a feature of the total joint replacement 10. In one embodiment, the resection plane may be defined by a feature (e.g., inner wall 162b) of the second frame 160 or by a combination of one or more features of the second frame 160 and a feature of the base 148. In one embodiment, sidewalls 162, 164 define a slot with inner edge 148f that is slightly larger than a preselected thickness of the third resection tool 170 and wider than a preselected thickness of the third resection tool 170 to allow the third resection tool 170 to slide from side to side within the guide path 166 but small enough to constrain undesirable movement away from the base 178.

In one embodiment, there are no sidewalls 162, 164 on the second frame 160 such that the guide path 166 is entirely open toward one side. In such an embodiment, care should be taken not to contact the medial and lateral malleolus 12e, 16a rather than rely on the sidewalls 162, 164 to stop the second tissue resection tool 170. In one embodiment, the second frame 160 of the third tissue resection guide 146 has an entirely closed perimeter wall (not shown). In one embodiment, the third resection guide 146 does not include a second frame 160 and the third resected tissue surface 104a is exposed by sliding the third tissue resection tool 170 against the first side 108a of the datum 108. The third tissue resection guide 146 may include indicia 172 such as a colored polymeric plug that indicates the size and/or right or left foot 26.

Fourth Tissue Resection Guide

Figure 12A:
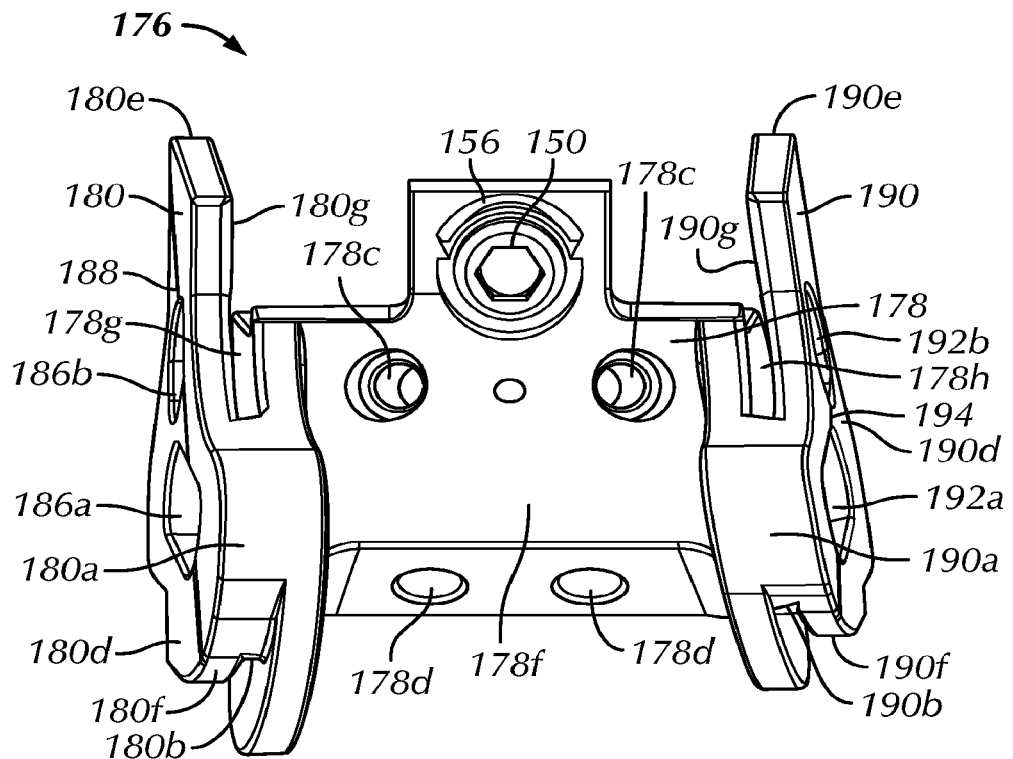
FIG. 12A is a top plan view of a fourth tissue resection guide in accordance with an exemplary embodiment of the present invention.
Figure 12B:
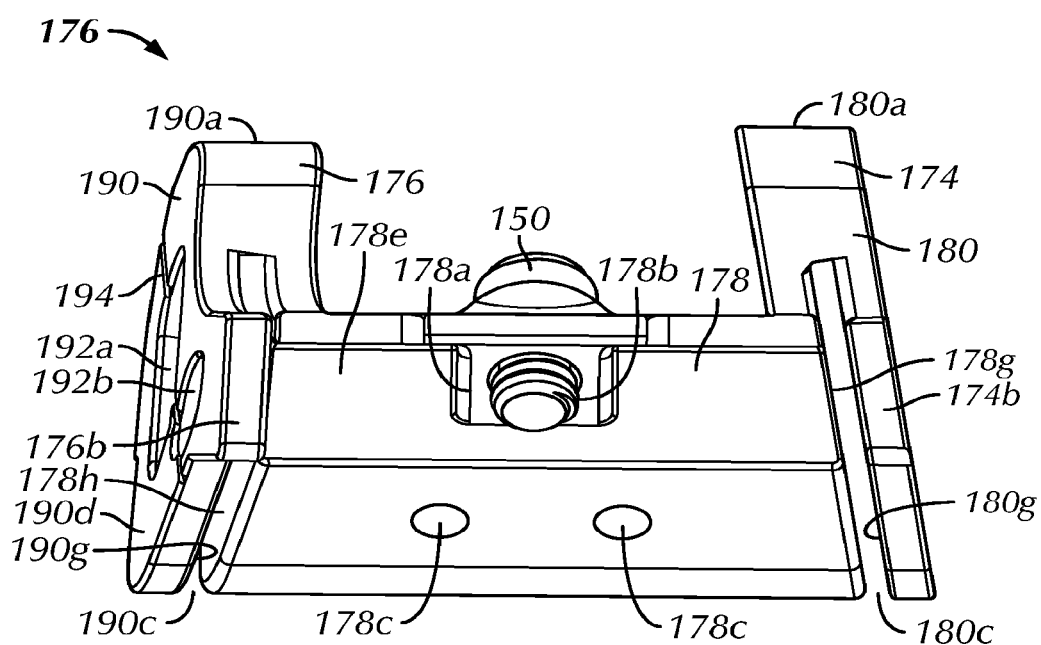
FIG. 12B is a front elevational view of the fourth tissue resection guide shown in FIG. 12A.
Figure 12C:
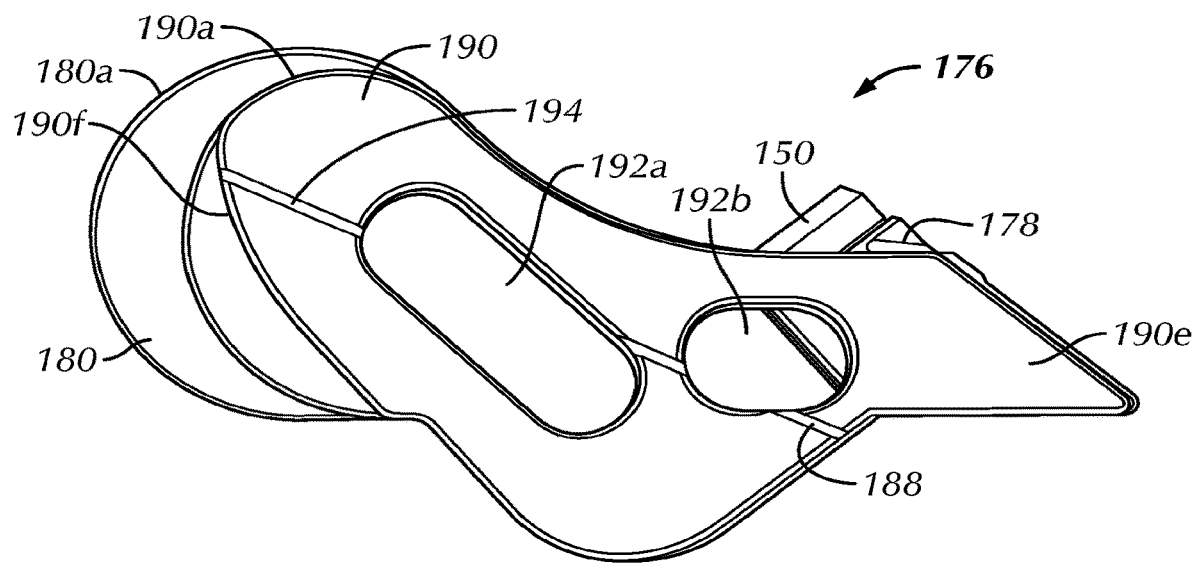
FIG. 12C is a side elevational view of the fourth tissue resection guide shown in FIG. 12A.

Referring to the embodiment of FIGS. 12A-12C, a fourth tissue resection guide 176 may be provided for resecting the second bone 14. The fourth tissue resection guide 176 is sized and configured to releasably attach to the top side 108f of the datum 108 (see FIGS. 31 and 32). The fourth tissue resection guide 176 is also configured to receive and guide one or more resection tools to resect tissue at predetermined orientation and location. In one embodiment, a resection using the fourth tissue resection guide 176 is made while fourth tissue resection guide 176 is attached to the datum 108 and while the datum 108 is attached to tissue (e.g., the second resected tissue surface 104). In one embodiment, the fourth tissue resection guide 176 is configured to guide one or more tissue resection tools adjacent to the datum 108. In one embodiment, the fourth resection tool 182 is guided adjacent to one or more sides of the datum 108. In one embodiment, the fourth resection tool 182 is guided adjacent to different sides of the datum 108 than the sides of the datum 108 that are adjacent to the resections made when the third tissue resection guide 146 is used as described above. In one embodiment, the fourth tissue resection guide 176 is a medial/lateral tissue resection guide for resecting the second bone 14 medial and lateral to the datum 108. However, the fourth tissue resection guide 176 may be used to resect the second bone 14 in any direction relative to the datum 108.

The fourth tissue resection guide 176 includes a base 178 that releasably engages the datum 108. The base 178 may include a datum projection 178a that extends from the base 178 and fits within the recessed section 108d of the datum 108 to prevent the fourth tissue resection guide 176 from rotating with respect to the datum 108. The datum projection 178a may include an aperture 178b for receiving a fastener 150 configured to secure the fourth tissue resection guide 176 to the datum 108. In one embodiment, the fastener 150 is an Allen screw. However, the fastener 150 may by any securement device such as a snap or magnet. The fastener 150 may be the same fastener 150 used to secure the third tissue resection guide 146 to the datum 108. In one embodiment, each of the third and fourth tissue resection guides 146, 176 may include its own fastener 150. The base 178 may include pin apertures 178c for fitting over the shoulder pins 114 extending from the datum 108. In one embodiment, the fourth tissue resection guide 176 is integral with the third tissue resection guide 146. The base 178 may include one or more grips 178d (see FIG. 12A) that are configured to engage an insertion tool (not shown) such as forceps. In one embodiment, the grips 178d may be apertures as shown.

The fourth tissue resection guide 176 may include a first frame 180 attached to the base 178 (e.g., such that the first frame 180 is integral with the base 178 or a separate component that is combined with the base 178). In one embodiment, the first frame 180 is adjacent to the second side 108b of the datum 108 when the fourth tissue resection guide 176 is engaged with the datum 108 and is configured to receive and guide a tissue resection tool such as the fourth tissue resection tool 182. (See FIG. 31).

The first frame 180 may include a guide path 180c for capturing and guiding the fourth tissue resection tool 182. In one embodiment, the guide path 180c is a generally planar elongated slot. In one embodiment, the guide path 180c is defined at least in part by an inner surface 180g of the first frame 180 and an outer surface 178g of the base 178. When the fourth tissue resection guide 176 is engaged with the datum 108 the guide path 180c may be further defined, at least in part, by the second side 108b of the datum 108.

In one embodiment, the guide path 180c of the first frame 180 is at least partially closed proximate a top 178f of the base 178 via a closed top 180a. In one embodiment, the guide path 180c is substantially open proximate the bottom 178e of the base 178. In one embodiment, the closed top 180a and open bottom of the guide path 180c permit the resection tool to move freely in a direction toward the second bone 12 but restricts the resection tool in a direction normal to the base 178 such that the resection tool may be slid downwardly out of the fourth resection guide 176 but not upwardly out of the fourth resection guide 176. The closed top 180a may be provided so that the fourth tissue resection tool 182 can be pivoted up against the closed top 180a during use. The closed top 180a may include a rounded inner edge 180b to contact the fourth tissue resection tool 182 and prevent a pointed contact between the first frame 180 and the fourth tissue resection tool 182. The first frame 180 may be open toward the bottom 178e of the base 178 such that the fourth tissue resection tool 182 may extend downwardly past the base 178 and resect the second bone 14 to further expose a fifth resected tissue surface 104c. The guide path 180c may be generally parallel to the second side 108b of the datum 108 when the fourth tissue resection guide 176 is engaged with the datum 108. Alternatively, the guide path 180c may be defined solely by the first frame 180 or solely between the first frame 180 and the base 178. In one embodiment, the guide path 180c of the first frame 180 is a generally rectangular slot.

In one embodiment, the fourth tissue resection tool 182 is a saw blade. However, the fourth tissue resection tool 182 may be any suitable resection device such as any one of the first, second and third tissue resection tools 168, 170 described above (the first tissue resection tool is not shown).

The first frame 180 of the fourth tissue resection guide 176 may include at least one viewing window 186 extending through an outer side 180d of the first frame 180. In one embodiment, the first cut guide 180 includes two viewing windows 186a, 186b. The outer side 180d of the first frame 180 may include an alignment feature such as an alignment line 188 (best shown in FIG. 31) that extends across or intersects the at least one viewing window 186 such that during use the depth of the fourth tissue resection tool 182 can be determined by aligning a feature 182a of the fourth tissue resection tool 182 such as the top edge of the fourth tissue resection tool 182 with the alignment line 188. (See FIG. 31). In one embodiment, the alignment line 188 is cut or etched into the outer side 180d of the first frame 180. Alternatively, the alignment line 188 may be printed or otherwise affixed to the outer side 180d of the first cut guide 180. The first frame 180 may be used to resect or expose the fifth resected tissue surface 104c. (See FIGS. 31 and 32).

Figure 31:
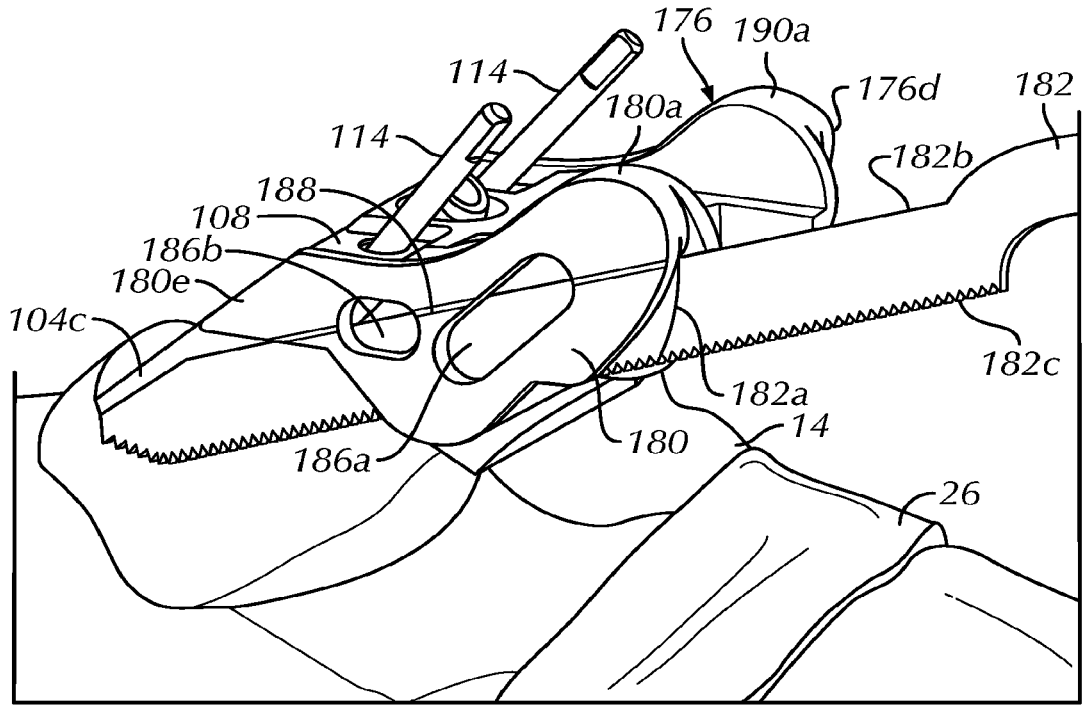
FIG. 31 is a perspective view of a fourth tissue resection tool being guided by the fourth tissue resection guide shown in FIG. 12A.
Figure 32:
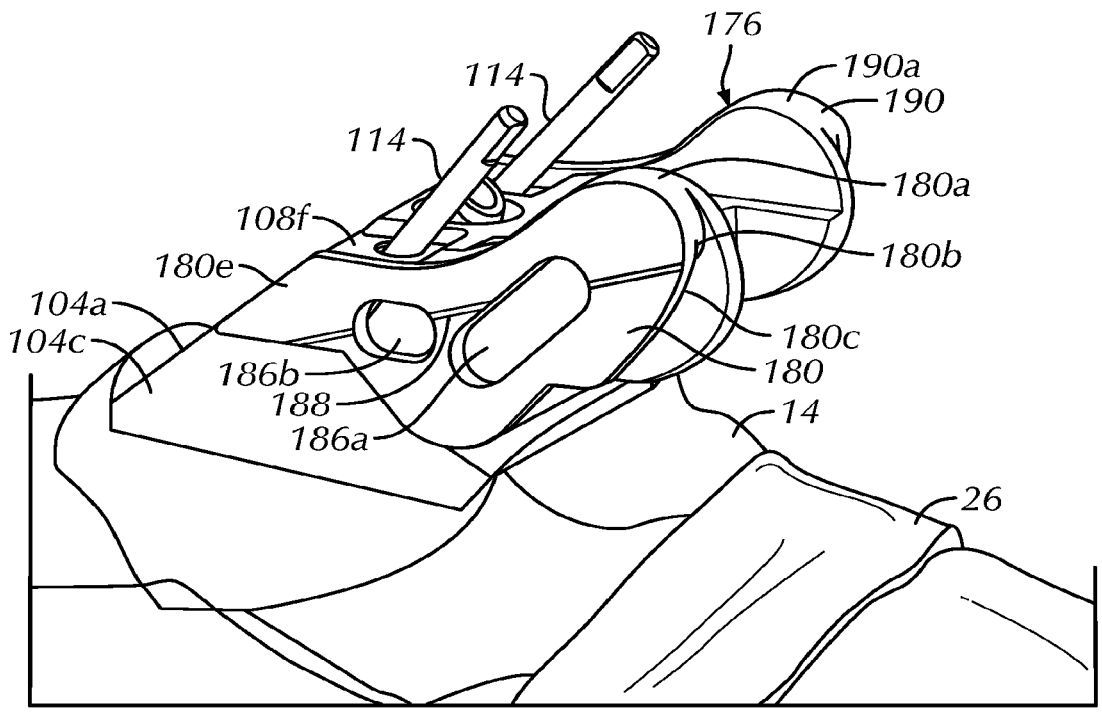
FIG. 32 is a perspective view of the fourth tissue resection guide shown in FIG. 31 showing the resected surface created by the fourth tissue resection tool.

Referring to FIGS. 31 and 32, in one embodiment, the fifth resected tissue surface 104c extends medially from the second resected tissue surface 104. In one embodiment, the fifth resected tissue surface 104c is generally parallel with the second side 108b of the datum 108. In one embodiment, approximately 0.5 mm to approximately 6 mm of tissue may be removed from second bone 14 to expose the fifth resected tissue surface 104c. In one embodiment, approximately 2 mm to approximately 3 mm of tissue is removed from second bone 14 proximal the second side 108b of the datum 108. The inferior extending length of the fifth resected tissue surface 104c may be approximately 5 mm to approximately 15 mm. In one embodiment, the inferior extending length of the medial extension 106c is approximately 10 mm.

The fourth tissue resection guide 176 may include a second frame 190 attached to the base 178. In one embodiment, the second frame 190 is a general mirror image of the first frame 180. In one embodiment, the second frame 190 and the first frame 180 are attached to the base 178 in a general symmetrical configuration (see, e.g., FIGS. 12A and 12B). In one embodiment, the second frame 190 and the first frame 180 are oriented to provide guides that facilitate serial medial and lateral resections while the fourth tissue resection guide 176 is attached to the datum 108 and the datum 108 is attached to the second bone 14 (e.g., without the need to detach and attach a cut guide to the second bone 14 between medial and lateral resections).

In one embodiment, the second frame 190 is adjacent to the third side 108c of the datum 108 when the fourth tissue resection guide 176 is engaged with the datum 108 and is configured to receive and guide a tissue resection tool such as the fourth tissue resection tool 182 (similar to the first frame 180 shown in FIG. 31). In one embodiment, the second frame 190 is integral with the base 178 or a separate component that is combined with the base 178. The second frame 190 may include a guide path 190c for capturing and/or guiding the fourth tissue resection tool 182. In one embodiment, the guide path 190c is defined at least in part by an inner surface 190g of the first frame 190 and an outer surface 178h of the base 178. When the fourth tissue resection guide 176 is engaged with the datum 108. The guide path 180c may be further defined, at least in part, by a third side 108c of the datum 108.

In one embodiment, the guide path 190c of the second frame 190 is at least partially covered or closed proximate a top 178f of the base 178 via a closed top 190a. In one embodiment, the guide path 190c is substantially open proximate the bottom 178e of the base 178. In one embodiment, the closed top 190a and open bottom permit the resection tool to move freely in a direction toward the second bone 12 but restricts the resection tool in a direction normal to the base 178 such that the resection tool may be slid downwardly out of the fourth resection guide 176 but not upwardly. The closed top 190a may be provided so that the fourth tissue resection tool 182 can be pivoted up against the closed top 190a during use. The closed top 190a of the second frame 190 may include a rounded inner edge 190b to contact the fourth tissue resection tool 182 and prevent a pointed contact between the first frame 190 and the fourth tissue resection tool 182. The second frame 190 may be open toward the bottom 178e of the base 178 such that the fourth tissue resection tool 182 may extend downwardly past the base 178 and resect the second bone 14 to further expose a sixth resected tissue surface 104d. The guide path 190c may be generally parallel to the third side 108c of the datum 108 when the fourth tissue resection guide 176 is engaged with the datum 108. Alternatively, the guide path 190c may be defined solely by the second frame 190 or solely between the second frame 190 and the base 178. In one embodiment, the guide path 190c of the second frame 190 is a generally rectangular slot.

The second frame 190 of the fourth tissue resection guide 176 may include at least one viewing window 192 extending through an outer side 190d of the second frame 190. In one embodiment, the second frame 190 includes two viewing windows 192*a*, 192*b*. The outer side 190*d* of the second frame 190 may include an alignment line 194 (best shown in FIG. 12A) that extends across the at least one viewing window 192 such that during use the depth of the fourth tissue resection tool 182 can be determined by aligning a feature 182*a* of the fourth tissue resection tool 182 such as the top edge of the fourth tissue resection tool 182 with the alignment line 194. In one embodiment, the alignment line 194 is cut or etched into the outer side 180*d* of the second frame 190. Alternatively, the alignment line 194 may be printed or otherwise affixed to the outer side 190*d* of the second frame 190. The second frame 190 may be used to resect or expose a sixth resected tissue surface 104*d*. (See FIG. 32).

Referring to FIG. 32, in one embodiment, the sixth resected tissue surface 104*d* extends laterally from the second resected tissue surface 104. In one embodiment, the sixth resected tissue surface 104*d* is generally parallel with the second side 108*b* of the datum 108. Approximately 0.5 mm to approximately 6 mm of tissue may be removed from second bone 14 to expose the sixth resected tissue surface 104*d*. In one embodiment, approximately 2 mm to approximately 3 mm of tissue is removed from second bone 14 proximal the third side 108*c* of the datum 108. The inferior extending length of the sixth resected tissue surface 104*d* is approximately 10 mm to approximately 25 mm. In one embodiment, the inferior extending length of the sixth resected tissue surface 104*d* is approximately 17 mm.

In one embodiment, (e.g., as illustrated in FIG. 12A) the second frame 190 is angled about an axis that is generally perpendicular to the top 178*f* of the base 178 such that the front edge 190*e* is angled inwardly toward the base 178. In one embodiment, the first frame 180 is angled about an axis that is generally perpendicular to the top 178*f* of the base 178 such that the front edge 180*e* is angled inwardly toward the base 178 (not illustrated). In one embodiment (e.g., as illustrated in FIG. 12B), the first frame 180 and/or second frame 190 are angled toward each other such that the closed tops 180*a*, 190*a* extend inwardly. In one embodiment, the angle of inclination of the first frame 180 and the second frame 190 are different. In one embodiment, the angles of inclination of the first and second frames 180, 190 are approximately equal to the angles of inclination of the respective second and third sides 108*b*, 108*c* of the datum 108.

In one embodiment, the ends 180*e*, 190*e* extend outwardly from the body 178 and generally taper to a point to protect surrounding tissue from the fourth tissue resection tool 182. However, the ends 180*e*, 190*e* of the first and second frames 180, 190 may have any shape and may or may not extend outwardly further from the body 178. In one embodiment, the top 180*a* of the first cut guide 180 extends further from the base 178 than the top 190*a* of the second cut guide 190 to allow for a deeper resection proximate the third side 108*c* of the datum 108 than the resection proximate the second side 108*b* of the datum 108. However, the first and second cut guides 180, 190 may be configured to make a similar depth cut or be oriented to make any desired resections proximate and relative to the datum 108. In one embodiment, the fourth tissue resection tool 182 includes vertically extending teeth 182*c* such that the teeth 182*c* do not contact the first or second cut guides 180, 190 during use.

Window Trial

Figure 13:
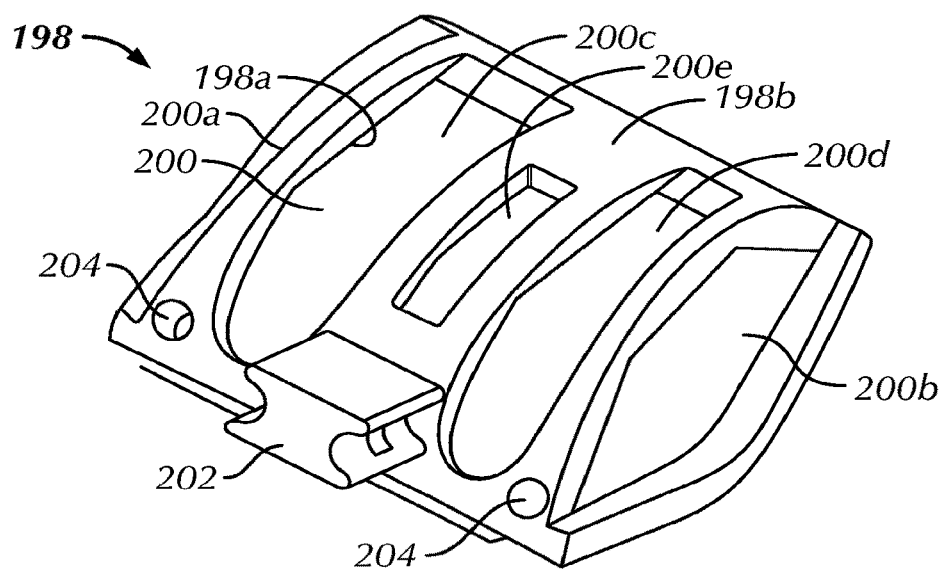
FIG. 13 is a perspective view of a window trial in accordance with an exemplary embodiment of the present invention.
Figure 14:
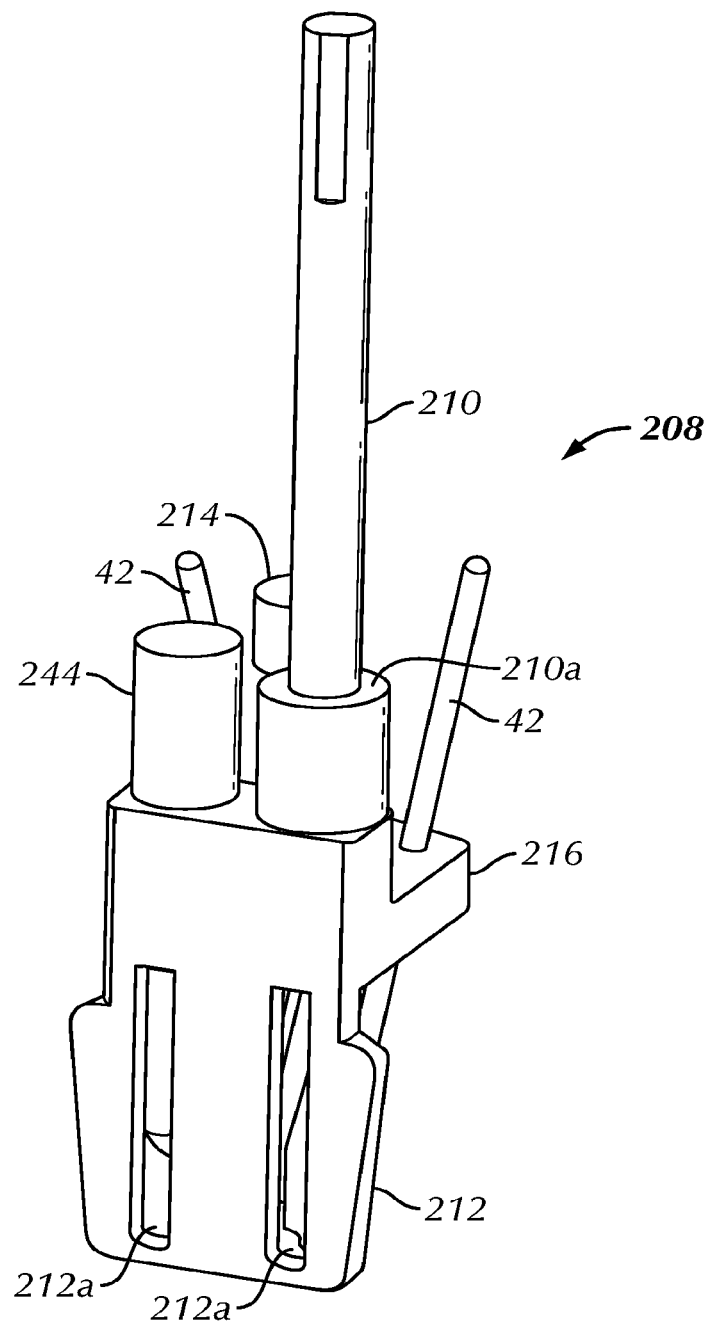
FIG. 14 is a perspective view of a barrel cut guide in accordance with an exemplary embodiment of the present invention.

Referring to the embodiment of FIG. 13, there is shown a window trial 198. The window trial 198 may include one or openings 200 to evaluate the resected second bone 14. The window trial 198 may be used to evaluate the second, third, fourth, fifth and sixth resected tissue surface tissues 104, 104*a*, 104*b*, 104*c*, 104*d*. (See FIGS. 33 and 34). The window trial 198 may have an inner surface 198*a* that generally has the shape of an inner surface of the second endoprosthetic component 18 of the total joint replacement 10. The window trial 198 may have an outer surface 198*b* that generally has the shape of an outer surface of the first endoprosthetic component 18 of the total joint replacement 10. In one embodiment, the window trial 198 has the same shape and configuration as the first endoprosthetic component 18 of the total joint replacement 10.

In one embodiment, the window trial 198 includes the one or more openings 200 for viewing and evaluating the shape of one or more of the second, third, fourth, fifth and sixth resected tissue surfaces 104, 104*a*, 104*b*, 104*c*, 104*d*, 104*e*. The window trial 198 may include side openings 200*a*, 200*b* proximate the fifth and sixth resected tissue surface 104*c*, 104*d* respectively. In one embodiment, the side openings 200*a*, 200*b* are generally aligned or parallel with the fifth and sixth resected tissue surface 104*c*, 104*d* respectively such that the fifth and sixth resected tissue surfaces 104*c*, 104*d* are not visible if the resections are proper when viewing the fifth and sixth resected tissue surfaces 104*c*, 104*d* at a viewing angle that is parallel and in-line with the fifth and sixth resected tissue surfaces 104*c*, 104*d* respectively. In one embodiment, first and second top openings 200*c*, 200*d* expose the second and fourth resected tissue surfaces 104, 104*b* respectively. The first and second top openings 200*c*, 200*d* may each expose the second resected tissue surface 104 proximate the third resected tissue surface 104*a* such that the inner surface 198*a* of the window trial 198 proximate the third resected tissue surface 104*a* is visible.

The window trial 198 may include a fin aperture 200*e*. In one embodiment, a keel mill or wire driver (not shown) is used to cut a keel slot (not shown) into the second 14 using the fin aperture 200*e* as a guide. The keel slot may be made for receiving the fin 18*b* of the first endoprosthetic component 18. The window trial 198 may include one or more pin apertures 204 for securing the window trial 198 to the second bone 14 using one or more pins 42. The window trial 198 optionally includes a handle 202 to assist in installing and removing the window trial 198 from the second bone 14 using a tool such as forceps (not shown). The window trial 198 may include indicia (not shown) such as a colored polymeric plug or printed graphic that indicates the size and/or right or left foot 26.

Barrel Cut Guide

Figure 17:
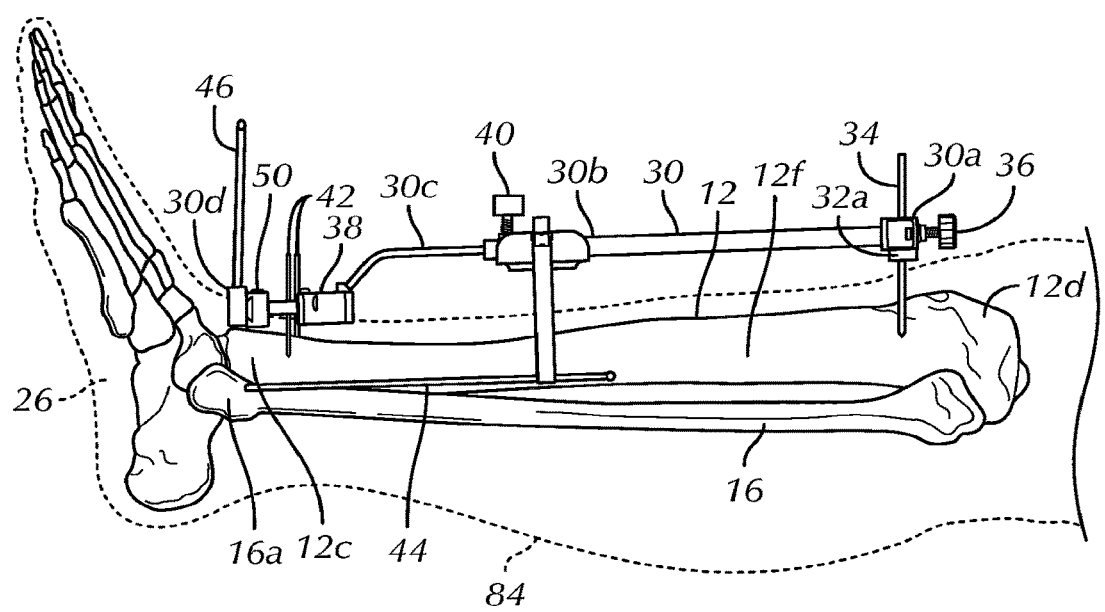
FIG. 17 a side elevational view of a lower leg of a patient with the alignment guide shown in FIG. 3 attached to the first bone.

Referring to the embodiment of FIG. 17, a barrel cut guide 208 may be provided. The barrel cut guide 208 may be configured to guide a fifth tissue resection tool 210 used to form the resected cavities 12*a* that receive the projections 20*a* of the second endoprosthetic component 20. (See FIGS. 1 and 2). In one embodiment, the fifth tissue resection tool 210 is a drill bit. In one embodiment, the barrel cut guide 208 includes a support plate 212. The support plate 212 may contact the first resected tissue surface 100 during use. The support plate 212 may also be used to measure the first resected tissue surface 100 for the appropriately sized second endoprosthetic component 20. In one embodiment, various support plates 212 are provided that correspond to the size of the second endoprosthetic component 20. In an alternative embodiment, the support plate 212 is partially transparent and includes various size markings for determining the size of the second endoprosthetic component 20.

The barrel cut guide 208 may be fixed to the first bone 12 by one or more pins 42. The barrel cut guide 208 may include a height adjuster 214 that may be used to space the barrel cut guide 208 an appropriate distance from the first bone 12. The space between the barrel cut guide 208 may be adjusted using the height adjuster 214 after the pins 42 are set if the pins 42 are inserted generally parallel with the height adjuster 214 or the length of height adjuster 214 extending from the barrel cut guide 208 may be set prior to inserting the pins 42 if the pins are inserted at an angle as shown. In one embodiment, the height adjuster 214 is a manually adjustable screw. However, the height adjuster 214 may be any device suitable to space the barrel cut guide 208 from the first bone 12.

The barrel cut guide 208 may include a body 216 that extends generally perpendicular from the support plate 212 such that the body 216 extends at least partially over the top of the first bone 12. The body 216 may include two apertures 216a (only one shown in FIG. 35) that are generally sized and shaped similar to the projections 20a of the second endoprosthetic component 20 and guide the fifth tissue resection tool 210. The fifth tissue resection tool 210 may include a shoulder 210a that contacts the body 216 and a maximum drilling depth to limit the depth of the resected cavities 12a a predetermined distance.

Figure 15:
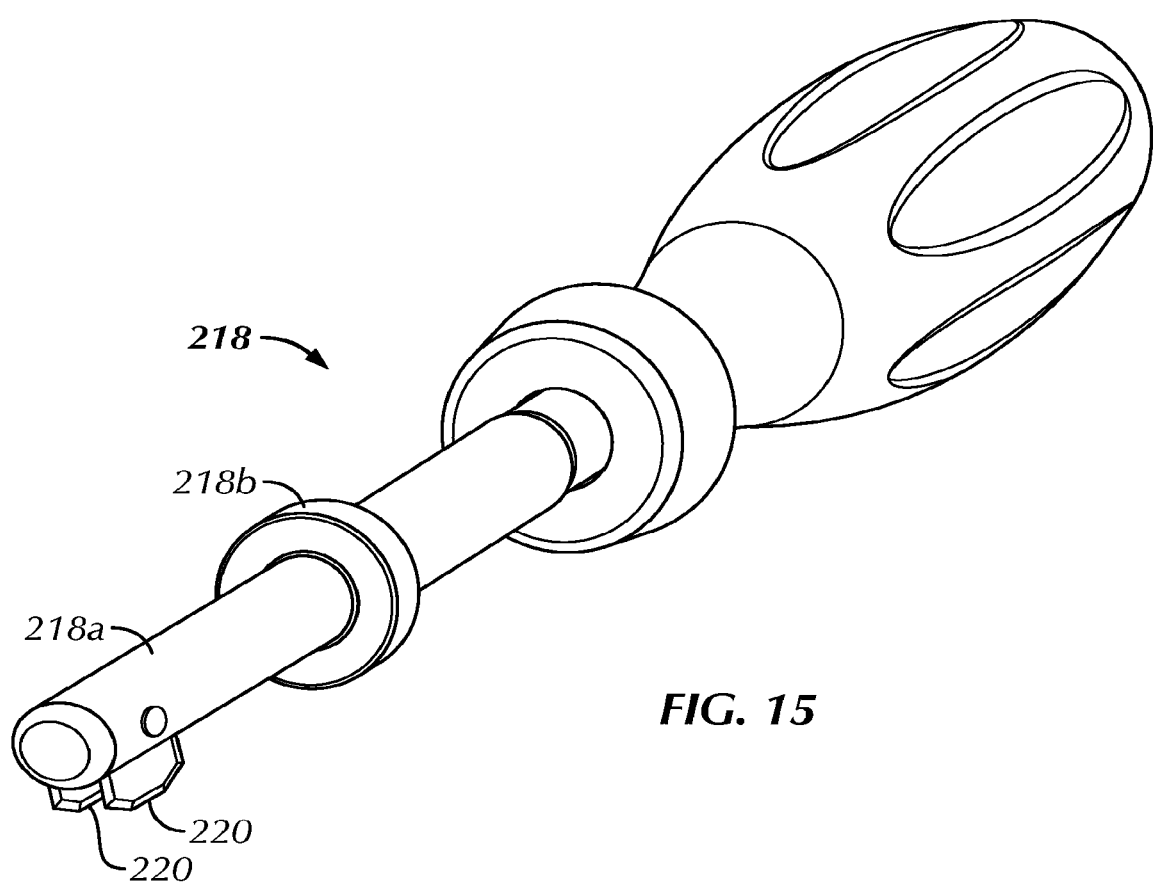
FIG. 15 is a perspective view of a fin cutter in accordance with an exemplary embodiment of the present invention.

Referring to the embodiment of FIG. 15, the resected cavities 12a may be opened or exposed through the first resected tissue surface 100 using a fin cutter 218 that is inserted through the apertures 216a, 216b of the barrel cut guide 208. In one embodiment, the fin cutter 218 includes a pair of fins 220 that are generally parallel and spaced apart from one another. The fins 220 may be configured to cut perpendicularly through the first resected tissue surface 100 through the resected cavities 12a. The support plate 212 may include slots 212a, 212b for receiving the fins 220 and the bone that is cut out by the fins 220. The fin cutter 218 may include a shaft 218a that is generally equal in size to the resected cavities 12a and a limit stop 218b that contacts the body 216 once the fins 220 have reached the end of the resected cavities 12a.

Method of Use

Figure 16:
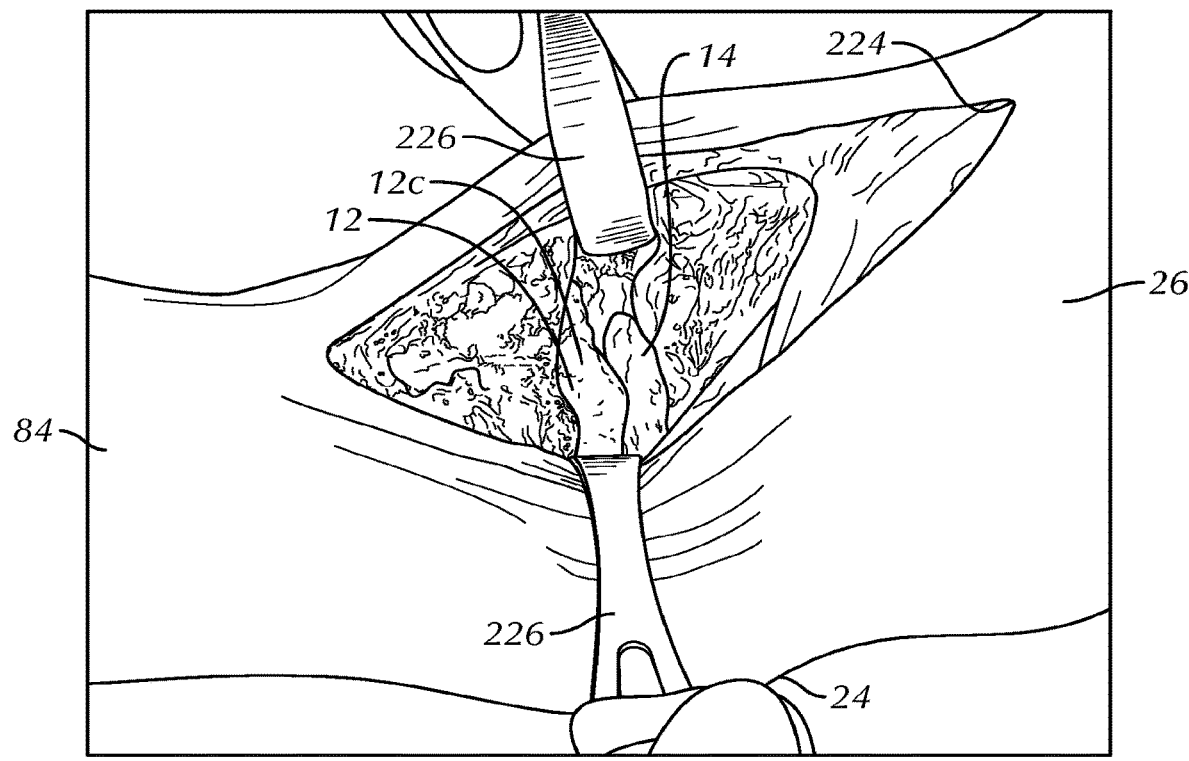
FIG. 16 is a perspective view of an incision in an ankle exposing the ankle joint.

Referring to FIGS. 16-35, there are shown exemplary embodiments of using the various instrumentation disclosed above for implanting the total joint replacement 10. Referring to FIG. 16, after the foot 26 and ankle 24 have been correctly positioned, the foot 26 and ankle 24 are preferably elevated. The foot 26 and ankle 24 are elevated for approximately two minutes. A high thigh tourniquet (not shown) may be inflated or tightened with an appropriate amount of pressure for the size of the leg 84 and foot 26. An incision 224 may be made along the anterior side of the ankle 24 parallel to the leg 84 to expose the joint between the tibia 12 and the talus 14. The incision 224 may be approximately 5 cm to approximately 30 cm in length. In one embodiment, the incision 224 is approximately 20 cm in length. The incision 224 may be centered over the ankle 24 immediately lateral to an anterior tibial tendon (not shown). The incision 224 may be deepened into the ankle 224 while moving the extensor hallucis longus (not shown) and the neurovascular bundle laterally. The incision 224 may expose the superficial dorsal peroneal nerve (not shown) and should be retracted carefully to the lateral side. In one embodiment, it may be necessary to sacrifice one branch of the superficial dorsal peroneal nerve that goes to the first metatarsal. The incision 224 may open the tendon sheath of the extensor hallucis longus (not shown) inline with the incision 224. In one embodiment, every effort is made not to open the anterior tibial tendon sheath (not shown) as such action might cause bolstering of the tendon during closing of the incision 224.

After the extensor hallucis longus tendon sheath is opened, the deep peroneal nerve and artery (not shown) which are just beneath the tendon sheath, may be retracted laterally in a gentle manner. The capsular tissues (not shown) in the ankle 24 may be incised in line with the incision 224 and then elevated and mobilized to expose the medial malleolus 12b (see FIG. 1) and the entire ankle joint. Care should be taken not to release the anterior talofibular ligament (not shown) as this will produce ankle instability.

The ankle joint may be distracted slightly using any suitable tool and excess synovium (not shown) and any loose bodies or bone spurs are removed using any suitable technique. In one embodiment, the anterior osteophytes (not shown) are excised so the tibial plafond 12c can be visualized. Retractors 226 are optionally used to hold the incision 224 open. In one embodiment, manually positioned retractors 226 are used over self retaining retractors. The retractors 226 may be frequently repositioned to minimize the risk of tissue trauma.

Referring to FIG. 17, the alignment guide 30 may be secured to the first bone 12 by inserting the pin 34 into a first end 12d of the first bone 12. In one embodiment, the first end 12d is the anterior tibial tubercle of the tibia. The pin 34 may be oriented approximately perpendicular to first bone 12. In one embodiment, the alignment guide 30 is positioned relative to the pin 34, both anteriorly and laterally, and secured to the pin 34 using the first securement 36.

In one embodiment, the attachment block 38 is positioned proximate a second end 12c of the first bone 12. In one embodiment, the second end 12c is the tibial plafond of the tibia. The positioning tool 46 may be secured to the second positioning block 54 to assist in positioning the attachment block 38 relative to the first bone 12. The attachment block 38 may be secured to the first bone 12 using one or more pins 42. The second securement 40 may be tightened to fix the length between the attachment block 38 and the first end 30a of the alignment guide 30.

In one embodiment, an osteotome (not shown), placed within the medial gutter, is used for additional visualization and setting proper orientation of the attachment block 38. The space adjustments 48 may be used to stabilize the attachment block 38 with respect to the first bone 12. In one embodiment, the distance between the attachment block 38 and the first bone 12 is as small as possible. In one embodiment, the attachment block 38 is positioned the approximate distance from the feature 12c of the first bone 12 such as the tibial plafond. A C-arm or other imaging device may be used to align the alignment rod 44 generally parallel with the longitudinal axis of the first bone 12. In one embodiment, the alignment rod 44 is generally aligned with a bone feature 12f in the anterior/posterior and lateral views (lateral view shown). In one embodiment, the bone feature 12f is the tibial crest of the tibia.

Figure 18:
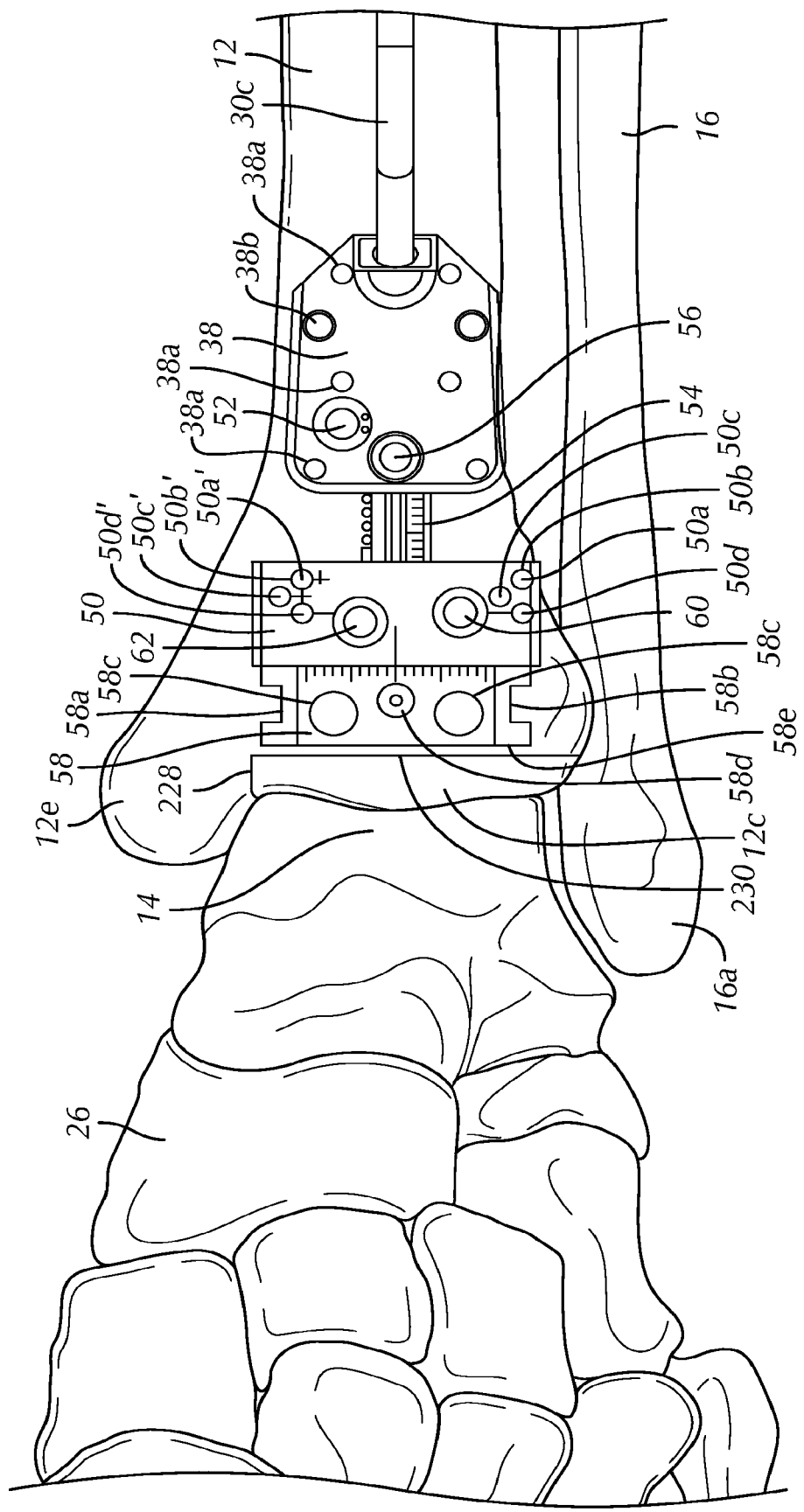
FIG. 18 is a top plan view of the alignment guide shown in FIG. 4 attached to the first bone and outlining two resection paths.

Referring to FIG. 18, once the attachment block 38 has been secured to the first bone 12, the first tissue resection guide 66 is attached to the second positioning block 58.

Figure 19:
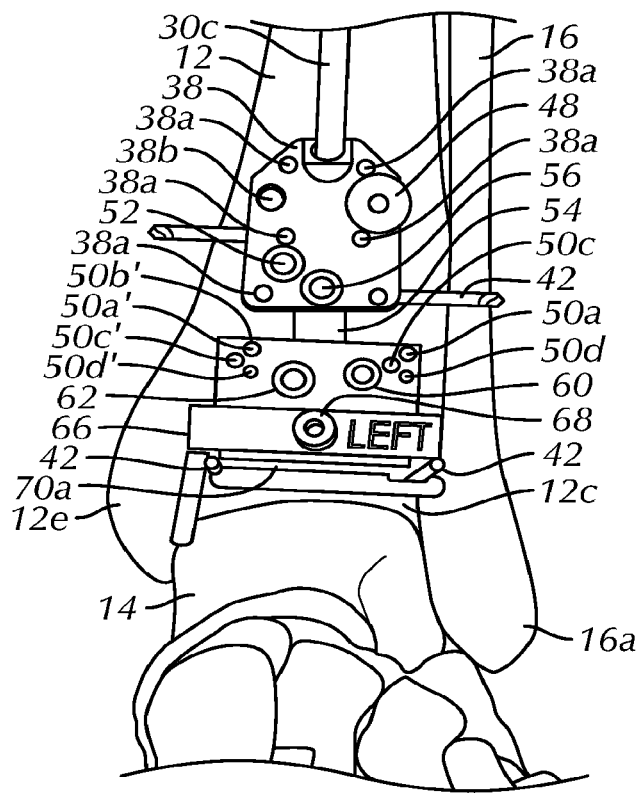
FIG. 19 is a top plan view of the alignment guide shown in FIG. 18 with the first tissue resection guide of FIG. 5 attached.
Figure 20:
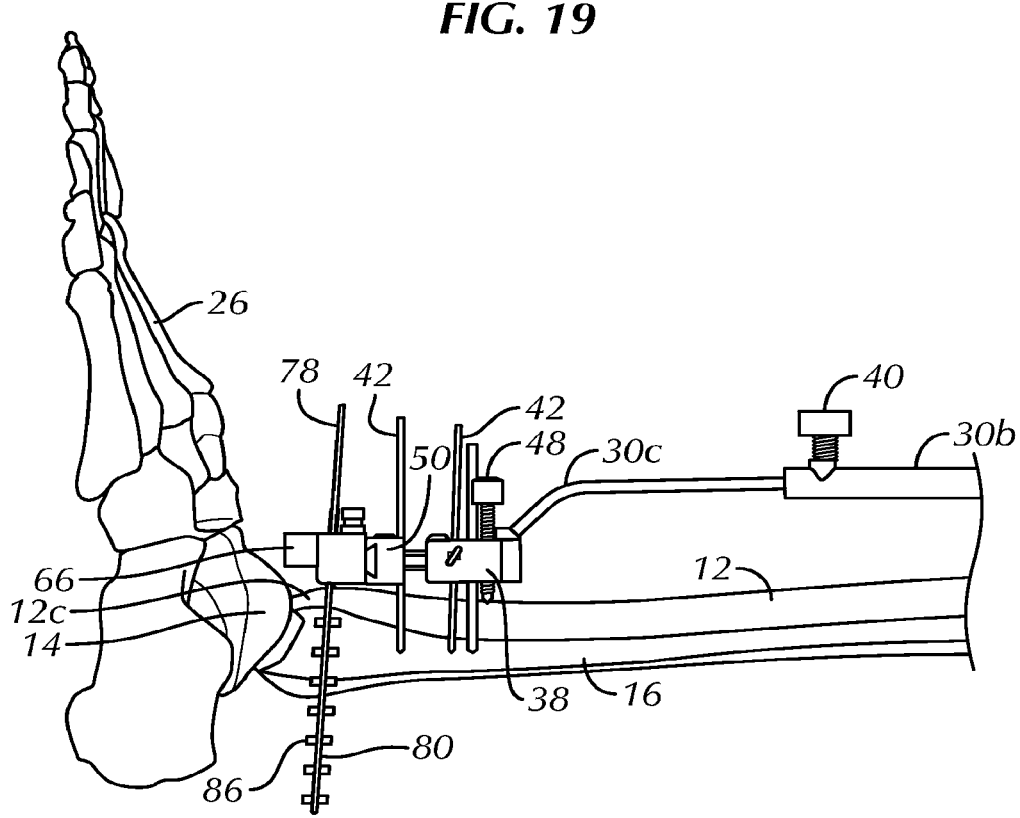
FIG. 20 is a side view of the alignment guide and first tissue resection guide shown in FIG. 19 with the spacer guide of FIG. 6 attached.

Referring to FIGS. 19 and 20, the spacer guide 78 may be attached to the first tissue resection guide 66 by inserting the mount 82 into the first guide path 70 of the first tissue resection guide 66. The C-arm or other imaging device may be used to view the ankle 24 from the lateral side proximate the extension arm 80 of the spacer guide 78. In one embodiment, the projections 86 are used to set the position first positioning block 50. In one embodiment, a single spacer guide 78 may be used for viewing the ankle 24 from either the medial or lateral side (FIG. 20). The spacer guide 78 may be removed and the C-arm or other imaging device may be used from the anterior side of the ankle 24. In one embodiment, the first tissue resection guide 66 is positioned by using the second positioning block 58 and by aligning the first guide path 70 between the between the medial and lateral malleolus 12e, 16a.

Once the position of the first tissue resection guide 66 is determined, pins 42 are inserted into the superior-most pin apertures 50b, 50b' of the respective plurality of pin apertures 50a, 50a' in the first positioning block 50. In one embodiment, pins 42 may be placed within the pin apertures 70a, 70b in the first tissue resection guide 66 to protect the medial and lateral malleolus 12e, 16a. In one embodiment, the first tissue resection tool such as a blade (not shown) is inserted within the first guide path 70 to resect or cut the distal end of the first bone 12 along a first cut line 228 (FIG. 18). The blade may be placed against the second guide path 72 to resect or cut a second cut line 230 (FIG. 18).

In one embodiment, when the alignment rod 44 is aligned with the feature 12f of the first bone 12, the top of the guide path 94 is angled back toward the alignment guide 30 such that the guide path 94 is at an approximately 87 degree angle with respect to the first bone 12. This allows for an angled first resected tissue surface 100 as best shown by the angle of the spacer guide 78 in FIG. 20 and the angle of the second endoprosthetic component 20 in FIG. 2. The angle of the guide path 94 relative to the first bone 12 may be altered by raising or dropping the first end 30a of the alignment guide 30 along the pin 34. The angle of the guide path 94 relative to the first bone 12 may be approximately 85 degrees to approximately 95 degrees and may have any orientation when the alignment rod 44 is generally parallel to longitudinal axis of the first bone 12. Once the guide path 94 is set to the desired positioned, the first resection tool is used to resect the first bone 12 along the first and second cut lines 228, 230. The resections along the first and second cut lines 228, 230 expose the first resected tissue surface 100 (FIG. 20).

Referring to FIG. 21, after the first resected tissue surface 100 is exposed, a second tissue resection guide 90' is inserted onto the first tissue resection guide 66. The foot 26 may be moved to a general plantigrade position (shown) such that the top of the second bone 14 engages the first resected tissue surface 100 or the tab extension 102'. The spacer guide 78 may be used to verify neutral positioning of the second bone 14. In one embodiment, the second tissue resection guide 90' is secured to the second bone 14 by pins 42 extending through the pin mounts 92. In such an embodiment, the second bone 14 is now fixed relative to the alignment guide 30. The first resection tool may be inserted within the guide path 94 of the second tissue resection guide 90' to resect or cut the second bone 14 exposing the second resected tissue surface 104. Alternatively, the above steps may be performed with second tissue resection guide 90.

Figure 22:
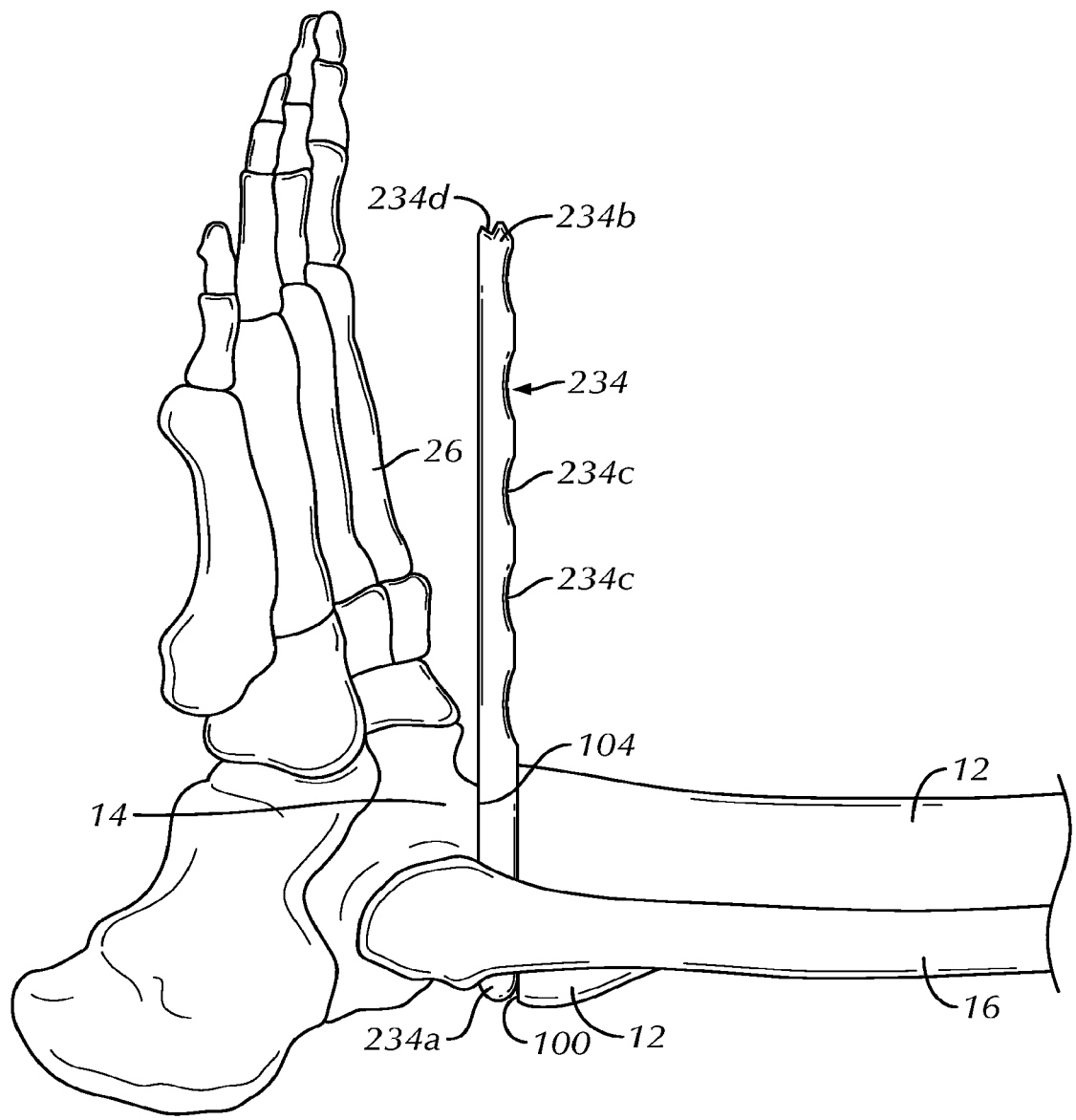
FIG. 22 is a side view of a space evaluator positioned between the first and second resected tissue surfaces.

Referring to FIG. 22, once the first and second resected tissue surfaces 100, 104 have been exposed, a space evaluator 234 may be inserted between the first and second resected tissue surfaces 100, 104 to ensure that the proper amount of tissue from the first and second bones 12, 14 has been resected. In one embodiment, the space evaluator 234 includes a plurality of finger grips 234c. The finger grips 234c may be inwardly extending grooves positioned on at least one side or lateral edge of the space evaluator 234.

The space evaluator 234 may have a predetermined thickness toward a first end 234a and a predetermined thickness toward a second end 234b. In one embodiment, the thickness of the first end 234a is approximately 6 mm to approximately 20 mm. In one embodiment, the thickness of the first end 234a is approximately 12 mm. For example, the first end 234a having a 12 mm thickness may include 3 mm of space for the second endoprosthetic component 20, 6 mm of space for the middle endoprosthetic component 22 and 3 mm of space for the first endoprosthetic component 18. If the space evaluator 234 does not fit between the first and second resected tissue surfaces 100, 104, the first bone 12 may be further resected. In one embodiment, the space evaluator 234 has a thinner thickness (e.g. approximately 9 mm) toward a second end 234b in the event that the distance measured using the spacer guide 78 is off, the measurement included cartilage or other non-bone tissue or if a joint is lax. In one an embodiment, if the final distance between the first and second resected tissue surfaces 100, 104 is thinner than the thickness of the first end 234a of the space evaluator 234, the second end 234b of the space evaluator 234 may be inserted between the first and second resected tissue surfaces 100, 104 to gauge the additional space needed. For example, if the second end 234b of the space evaluator 234 fits snugly between the first and second resected tissue surfaces 100, 104 then an additional distance, such as 2 mm, can be resected from the first bone 12. The first bone 12 may be further resected by removing the pins 42 from first positioning block 50, moving the first positioning block 50 one or more predetermined length increments (e.g. 2 mm) such that the original pin holes 50b, 50b' in the first bone 12 align with the adjacent pin holes 50c, 50c' and then reinserting the pins 42 into the first positioning block 50 through the pin holes 50c, 50c'.

Figure 23:
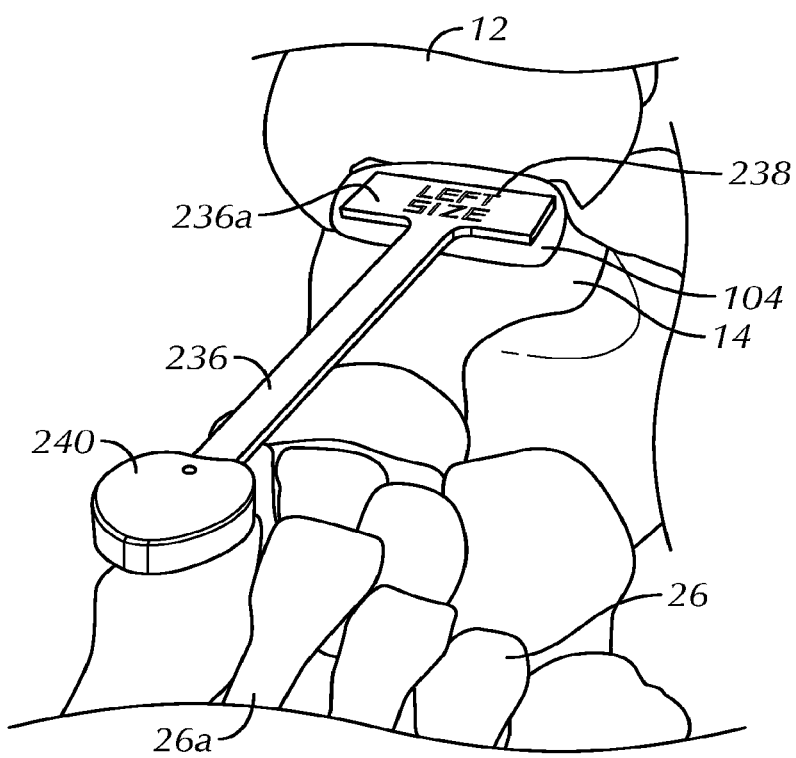
FIG. 23 is a perspective view of a sizer on top of the second resected tissue surface.

Referring to FIG. 23, once there is sufficient space for implanting the total joint replacement 10 between the first and second bones 12, 14 the foot 26 may be plantar flexed (shown) to achieve better access to the second resected tissue surface 104. In one embodiment, a sizer 236 is inserted over the second resected tissue surface 104. The sizer 236 may be used to measure the size of the second resected tissue surface 104 such as the anterior/posterior depth and the medial/lateral width. In one embodiment, the sizer 236 has a general shape and size of the datum 108. The appropriately sized datum 108 may be determined by adding, or leaving, a predetermined distance (e.g. 3 mm) to each medial/lateral side of the sizer 234. In one embodiment, a different sizer 234 is provided for each datum size. In one embodiment, the size of the sizer 234 and right or left foot 26 being measured is indicated by indicia 238 such as printed words (e.g. left ankle, size small). The sizer 234 may included a handle 240 that is color coded to the size of the sizer 234. In an alternative embodiment, the sizer 234 is at least partially transparent with nested outlines (not shown) of differently sized datum 108 that allow a user to select the appropriate size. In one embodiment, the size of the first endoprosthetic component 18 is verified by measuring the distance between the medial and lateral malleolus 12e, 16a. In one embodiment, the sizer 234 is outlined or traced on the second resected tissue surface 104 using a marking material such as a skin marker to help indicate the position the datum 108. The sizer 234 may be properly positioned by aligning the handle 240 with a second metatarsal 26a of the foot 26.

Referring to FIGS. 24 and 25, once the appropriately sized datum 108 is selected, the datum 108 is attached and secured to the distractor 120. In one embodiment, the datum 108 is positioned relative to the alignment block 38 using a guide (not shown). The datum 108 may be inserted onto the second resected tissue surface 104 using the distractor 120 and may be generally positioned within the outline previously marked on the second resected tissue surface 104. In one embodiment, the datum 108 is positioned on the second resected tissue surface 104 by aligning the distractor 122 with the second metatarsal 26a. In one embodiment, the C-arm or other imaging device is used to further verify the position of the datum 108 with respect to the second surface 104. In one embodiment, the paddle 140 engages the first resected tissue surface 100 in the insertion position (FIG. 24) and the upper handle 136 is squeezed toward the lower handle 130 to separate the first resected tissue surface 100 from the second resected tissue surface 104. The ratchet 142 may hold the upper and lower handles 136, 130 in position with respect to each other such that the distractor 120 can be held in a distracted position without having to continually squeeze the handles 130, 136. Alternatively, the ratchet 142 may be disengaged and is folded inwardly to lay on the lower handle 130 (see FIG. 10D).

Figure 26:
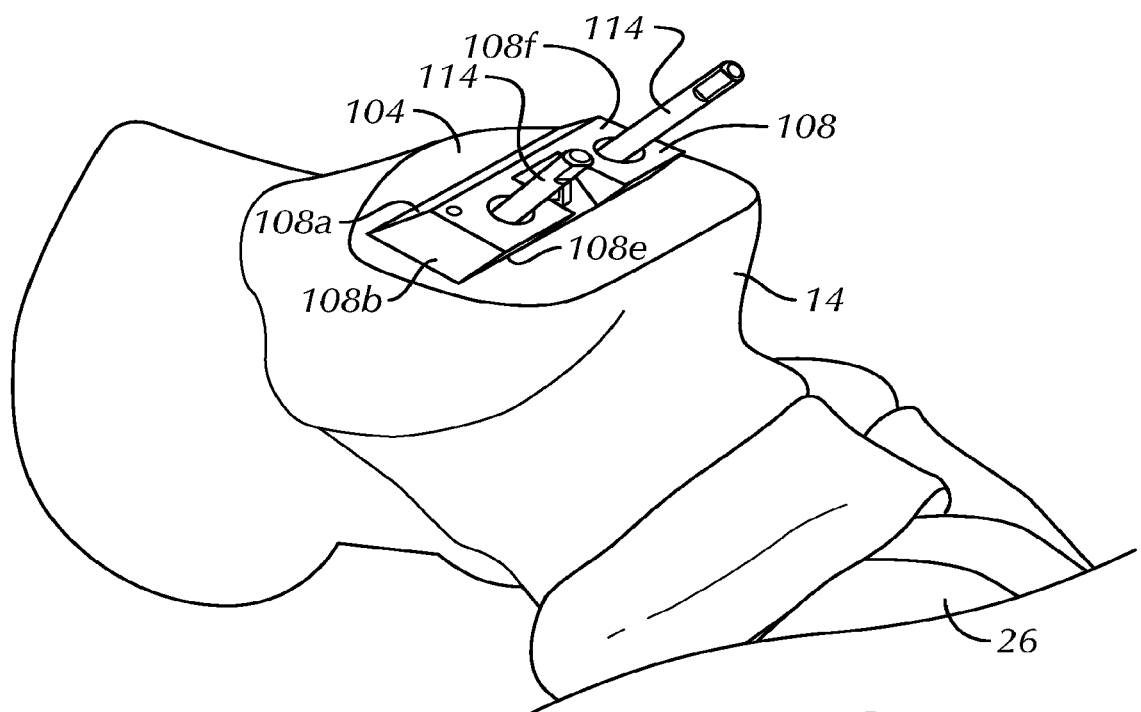
FIG. 26 is a perspective view of the datum attached to the second resected tissue surface.

With the first resected tissue surface 100 distracted from the second resected tissue surface in the distraction position (FIG. 25), the datum 108 may be secured to the second resected tissue surface 104 by inserting the shoulder pins 114 through the pin apertures 112 of the datum 108. Once the datum 108 is sufficiently secured to the second resected tissue surface 104, the distractor may be returned to the insertion position (FIG. 24), the datum lock 126 is released and the distractor 120 is removed from the ankle 24 leaving the datum 108 in place on the second resected tissue surface 104 (FIG. 26).

Figure 27:
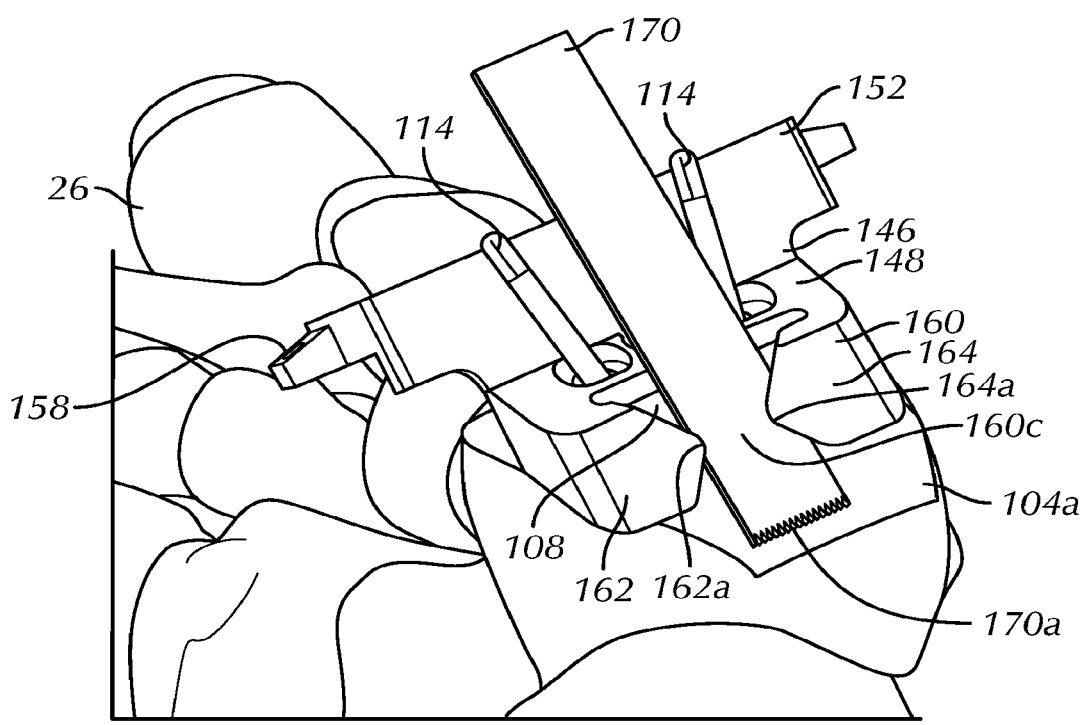
FIG. 27 is a rear perspective view of a second tissue resection tool being guided by the third tissue resection guide shown in FIG. 11A.

Referring to FIG. 27, once the datum 108 has been secured to the second resected tissue surface 104, the third tissue resection guide 146 is releasably secured to the datum 108. A second tissue resection tool 170 may be inserted within the second frame 160 and guided by the guide path 166 of the second frame 160 to resect the second bone 14 relative to the datum 108 and expose the third resected tissue surface 104a. In one embodiment, the second tissue resection tool 170 is slid back and forth within the second frame 160 and along the first side 108a of the datum 108 such that the cutting end 170a resects tissue proximate the datum 108. The second tissue resection tool 170 may be viewed through the open perimeter 160c. In one embodiment, the second tissue resection tool 170 is removed from the third tissue resection guide 146 to inspect the third resected tissue surface 104a.

Referring to FIG. 28, the third tissue resection tool 168 may be inserted within the enlarged end 154a of first guide path 154 of the third tissue resection guide 146. In one embodiment, the third tissue resection tool 168 is inserted until the stop 168c of the third tissue resection tool 168 abuts the first frame 152. The third tissue resection tool 168 may be guided proximate the fourth side 108e of the datum 108 to resect or cut the second bone 14 and expand the second resected tissue surface 104 away from the fourth side 108e of the datum 108. In one embodiment, the fourth side 108e of the datum 108 nearly contacts the head 170a of the third tissue resection tool 170. The third tissue resection tool 168 may be guided back along the first guide path 154 and the cutting head 168a may be removed from the first guide path 154 through the enlarged end 154a.

Referring to FIG. 29, in one embodiment, the third tissue resection tool 168 is inserted within the enlarged end 156a of second guide path 156. The third tissue resection tool 168 may be inserted until the stop 168b of the third tissue resection tool 168 abuts the first frame 152 of the third tissue resection guide 146. The third tissue resection tool 168 is guided proximate the fourth side 108e of the datum 108 to resect or cut the second bone 14 and expand the second resected tissue surface 104 away from the fourth side 108e of the datum 108. The third tissue resection tool 168 is guided back along the second guide path 156 and the cutting head 168a is removed from the second guide path 156 through the enlarged end 156a.

Figure 30:
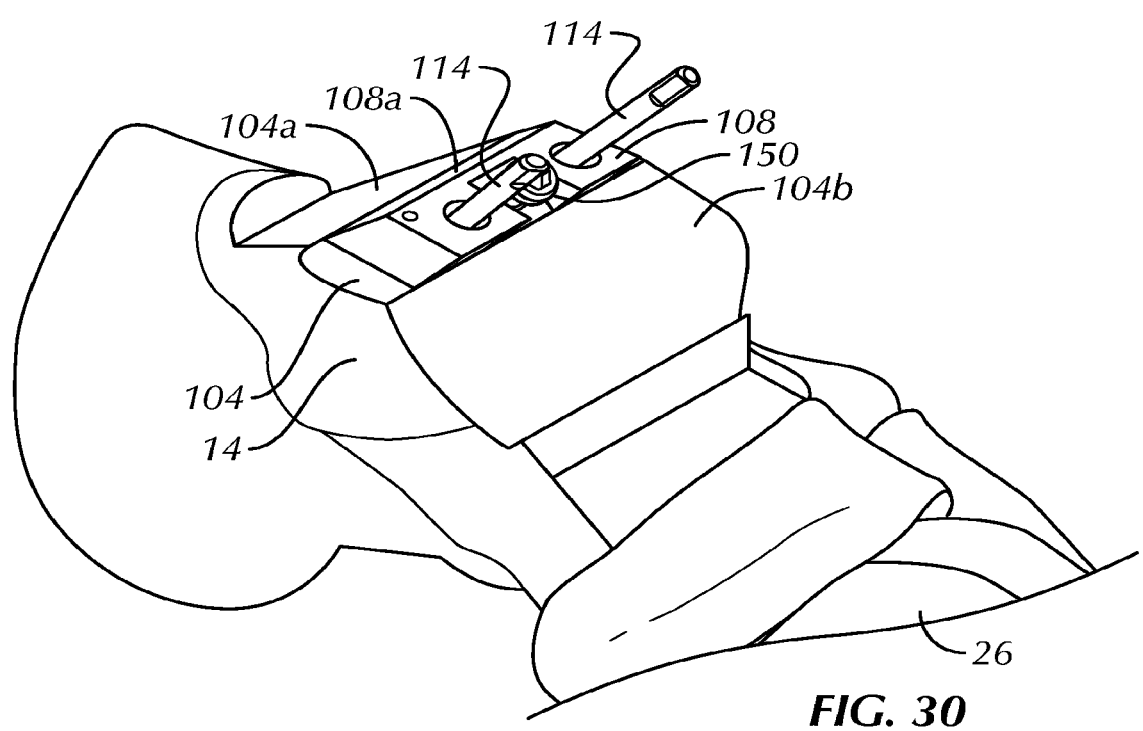
FIG. 30 is a perspective view of the second resected tissue surface after use of the second and third tissue resection guides shown in FIGS. 8 and 11A respectively.

Referring to FIG. 30, the third tissue resection guide 146 may be removed from the datum 114 revealing the third and fourth resected tissue surfaces 104a, 104b left after use of the third tissue resection guide 146.

Referring to FIGS. 31 and 32, the fourth tissue resection guide 176 may be releasably secured to the datum 108. In one embodiment, the datum 108 remains in the same position on the second resected tissue surface 104 for use with both the third and fourth tissue resection guides 146, 176. Once the fourth tissue resection guide 176 is secured to the datum 114, the fourth tissue resection tool 182 may be inserted into the first guide path 180c of the first frame 180. In one embodiment, the fourth tissue resection tool 182 is inserted into the first guide path 180c of the first frame 180 in the posterior anatomical direction until a feature such as the depth marking 182a of the fourth tissue resection tool 182 aligns with a feature of the first frame 180 such as an edge 180f. The fourth tissue resection tool 182 may be slid and/or pivoted downwardly though the first guide path 180c until the upper edge 182b of the fourth tissue resection tool 182 aligns with the alignment line 188. The proximal end of the fourth tissue resection tool 182 may be pulled upwardly to contact the edge 180b of the first frame 180 to thereby pivot the distal end of the fourth tissue resection tool 182 downwardly toward and into the second bone 14.

In one embodiment, the fourth tissue resection tool 182 is inserted into the second guide path 190c of the second frame 190. In one embodiment, the fourth tissue resection tool 182 is inserted into the second guide path 190c in the posterior anatomical direction until a feature such as the depth marking 182a of the fourth tissue resection tool 182 aligns with a feature of the second frame 190 such as an edge 190f. The fourth tissue resection tool 182 may be slid and/or pivoted downwardly though the second guide path 190c until the upper edge 182b of the fourth tissue resection guide 182 aligns with the alignment line 194. The proximal end of the fourth tissue resection guide 182 may be pulled upwardly to contact the edge 190b to thereby pivot the distal end of the fourth tissue resection guide 182 downwardly toward and into the second bone 14.

Figure 33:
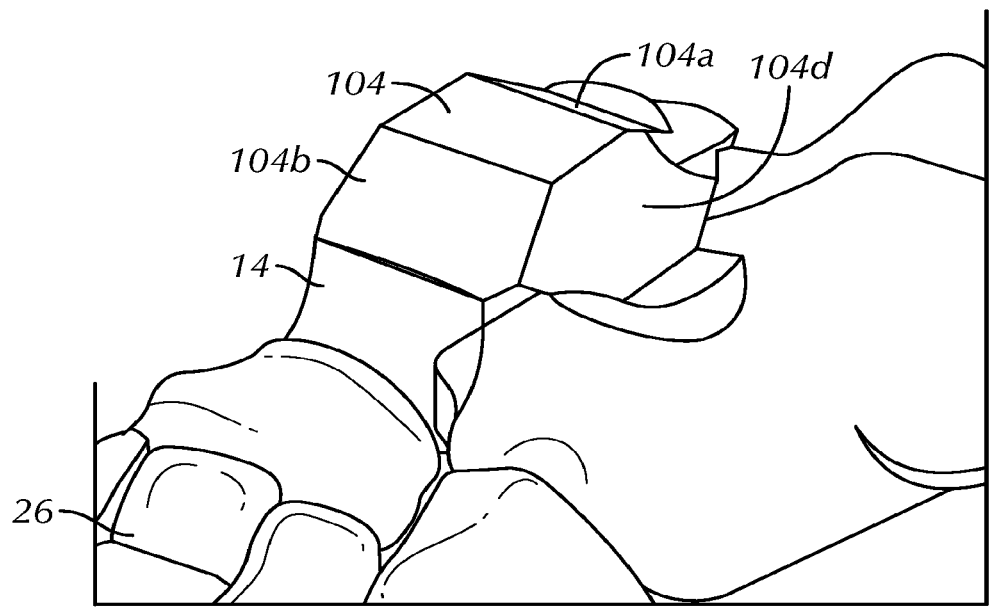
FIG. 33 is a perspective view of the resected tissue surfaces after use of the second, third and fourth tissue resection guides shown in FIGS. 8, 11A and 12A respectively.

Referring to FIG. 33, the fourth tissue resection guide 176 and the datum 108 may be removed from the second bone 14 to expose the second third, fourth, fifth and sixth resected tissue surfaces 104, 104a, 104b, 104c, 104d. In one embodiment, the resected tissue surfaces 104, 104a, 104b, 104c, 104d are inspected for any burrs and/or missed or miss cut portions. The resected tissue surfaces 104, 104a, 104b, 104c, 104d may be resected further if necessary using the instrumentation above and/or through free hand resection.

Figure 34:
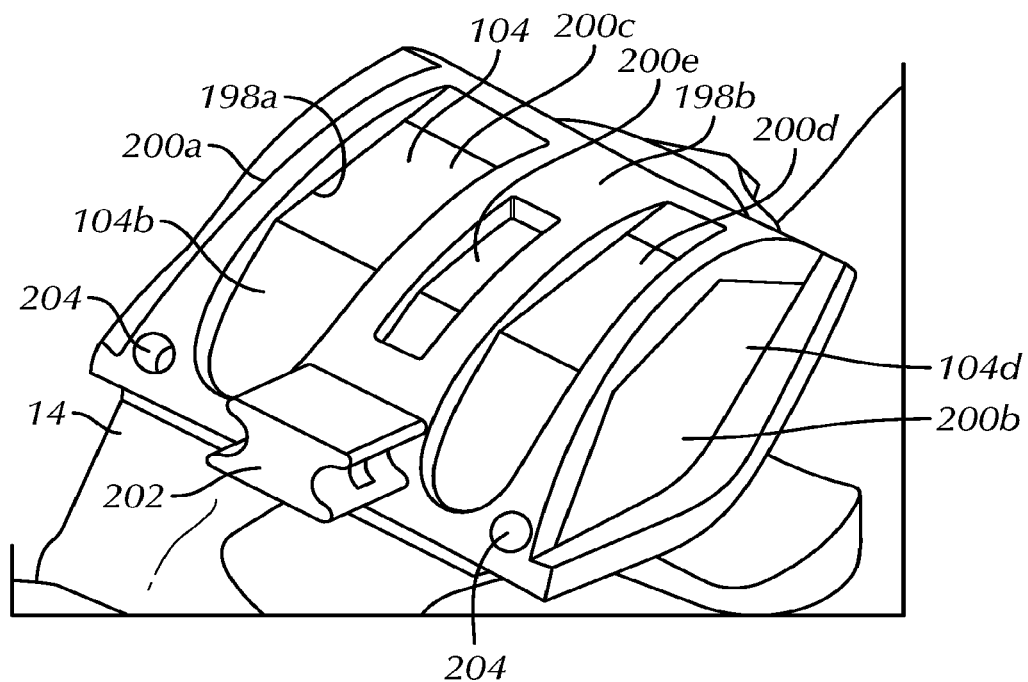
FIG. 34 is a perspective view of the window trial shown in FIG. 13 on the resected tissue surfaces shown in FIG. 33.

Referring to FIG. 34, the window trial 198 may be used to further evaluate the second resected tissue surface 104 and the various cuts made to the second bone 14. The window trial 198 may be installed or inserted over the second resected tissue surface 104 using a tool, such as forceps, attached to the handle 202. If the resections made to the second bone 14 are off, the inner surface 198a of the window trial 198 will be at least partially raised off of the second resected tissue surface 104 and/or tissue will be visible through one or more of the openings 200. In one embodiment, if the window trial 198 does not fit and/or if excess tissue is visible through the openings 200, a bone rasp (not shown) or other resection device is used to clean up the resections and provide a better fit with the window trial 198 and ultimately the first endoprosthetic component 18. The window trial 198 may be pinned to the second bone 14 using one or more pins 42. A keel mill or wire driver (not shown) may be used to cut a keel slot (not shown) into the second bone 14 using the fin aperture 200e as a guide. In one embodiment, a keel broach (not shown) is used to clean any remaining tissue in the keel slot.

Figure 35:
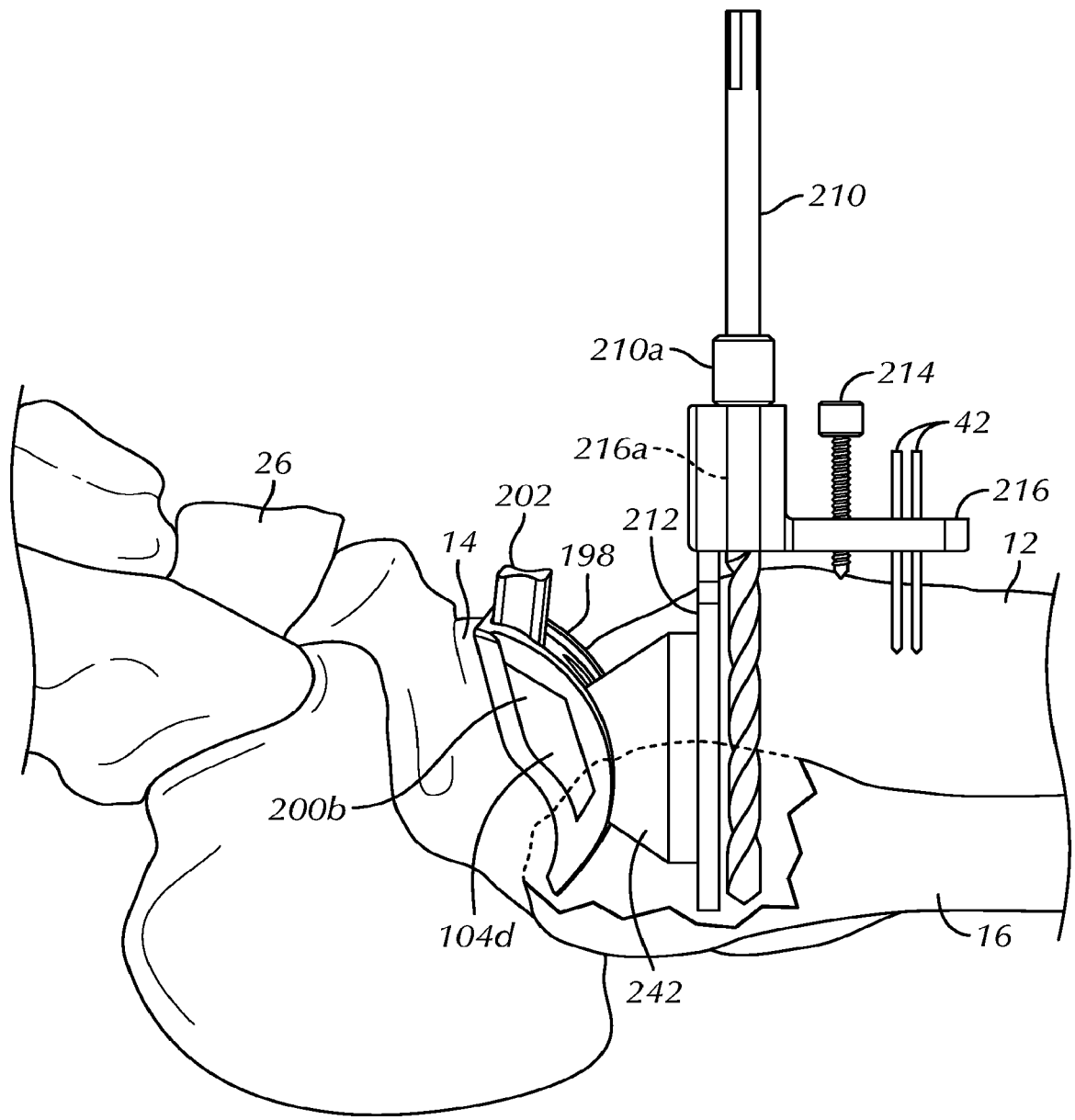
FIG. 35 is a side elevational partially transparent view of the barrel cut guide shown in FIG. 14 and the window trial on the resected tissue surfaces shown in FIG. 34.

Referring to FIG. 35, the barrel cut guide 208 may be attached to the first bone 12. In one embodiment, the barrel cut guide 208 is configured to utilize the same pins 42 and/or pin holes in the first bone 12 that were used to secure the first positioning block 50 to the first bone 12. In one embodiment, the support plate 212 is generally flush against the first resected tissue surface 100. The position of the barrel cut guide 208 toward and away from the first bone 12 may be adjusted with the height adjuster 214. The window trial 198 may be left on the second resected tissue surface 104 to protect the second resected tissue surface 104 during installation and use of the barrel cut guide 208. In one embodiment, a joint spacer 242 having the general shape and size of the middle endoprosthetic component 22 of the total joint replacement 10 is inserted between the window trial 198 and the support plate 212 to keep the support plate 212 in contact with the first resected tissue surface 100. The joint spacer 242 may also be used to determine the appropriate size and shape of the middle endoprosthetic component 22.

A fifth tissue resection tool 210 may be inserted into the apertures 216a of the barrel cut guide 208 to create the resected cavities 12a. (See FIG. 1). A barrel broach (not shown) may be used to clean the cavities 12a of remaining bone. The resected cavities 12a may be opened or exposed through the first resected tissue surface 100 by using the fin cutter 218. The fin cutter 218 is inserted into the apertures of the barrel cut guide 208 to remove the section of bone between the resected cavities 12a and the first resected tissue surface 100 such that the projections 20a may extend from the second endoprosthetic component 20 into the resected cavities 12a. The resected bone may be removed from the ankle 24 by any suitable technique.

In one embodiment, the size of the resected cavities 12a is assessed using a trial bearing 244. (See FIG. 14). The window trial 198, the joint spacer 242 and the barrel cut guide 208 may be removed from the ankle 24. The first endoprosthetic component 18 may be inserted over the second resected tissue surface 104. In one embodiment, an impactor (not shown) is used to seat the first endoprosthetic component 18 on the second resected tissue surface 104. A notched end 234d of the space evaluator 234 (see FIG. 10) may be used to lift an anterior edge of the first endoprosthetic component 18 and drive the posterior of the first endoprosthetic component 18 inferiorly in an effort to seat the first endoprosthetic component 18 on the second resected tissue surface 104. In one embodiment, the second endoprosthetic component 20 is implanted or mounted using an insertion device (not shown). The projections 20a may be aligned with the resected cavities 12a. In one embodiment, a mallet (not shown) is used to gently drive the second endoprosthetic component 20 downwardly and into position on the first bone 12. An anterior edge of the second endoprosthetic component 20 may be flush with the anterior tibial cortex. In one embodiment, a sponge (not shown) is placed over the first endoprosthetic component 18 to protect the first endoprosthetic component 18 while the second endoprosthetic component 20 is being inserted. Variously sized and shaped joint trials or spacers 242 may be inserted between the first and second endoprosthetic components 18, 20 to evaluate desired joint tension and position. After a satisfactory reduction is accomplished, the joint spacer 242 may be replaced with the appropriate middle endoprosthetic component 22. The incision 24 may then be closed.

The bone removed from the first and second bones 12, 14 using the above instrumentation and methods may be kept to a minimum. In one embodiment, the reduced amount of bone resection achieved as a result of the above procedures means that if the total joint replacement 10 needs to be removed and a salvage ankle joint fusion performed, the patient will not have a noticeable leg-length discrepancy.

Tissue Resection Kit

In one embodiment, a tissue resection kit (not explicitly shown) for implanting the total joint replacement 10 is provided and includes any combination of the above instrumentation. In one embodiment, the tissue resection kit includes the datum 108 and one or more tissue resection guides (e.g., the third and fourth resection guides 146, 176) that are size and configured to releasably engage the datum 108 and guide a tissue resection tool. In one embodiment, the tissue resection guide of the tissue resection kit includes the third tissue resection guide 146. In one embodiment, tissue resection guide of the tissue resection kit includes the fourth tissue resection guide 176. The tissue resection kit may include the first tissue resection guide 66. The tissue resection kit may include the spacer guide 78. The tissue resection kit may include the second tissue resection guide 90. The tissue resection kit may include the sizer 236. The tissue resection kit may include the distractor 120. The tissue resection kit may include the window trial 198. The tissue resection kit may include the barrel cut guide 208. The tissue resection kit may include the fin cutter 218. In one embodiment, the tissue resection kit includes more than one of the same instrument or component but of various sizes. The tissue resection kit may include instrumentation for one of the left and right ankle 24. The tissue resection kit optionally includes instrumentation for both left and right ankle 24.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the appended claims. For example, specific features of the exemplary embodiments may or may not be part of the claimed invention and combinations of disclosed embodiments may be combined. The words "right", "left", "lower" and "upper" designate directions in the drawings to which reference is made. The words "inwardly" and "outwardly" refer to directions toward and away from, respectively, the geometric center of the device. Unless specifically set forth herein, the terms "a", "an" and "the" are not limited to one element but instead should be read as meaning "at least one".

Further, to the extent that the methods do not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

The invention claimed is:

1. A spacer guide comprising:
a central body extending between a first end and a second end, the central body having a first width at the second end;
an extension arm extending from the second end of the central body; and
a plurality of projections disposed on a first surface of the extension arm,
wherein the extension arm has a second width parallel to the first width and measured across the extension arm at one of the plurality of projections, the second width narrower than the first width,
wherein the central body includes a first edge extending between the first end and the second end, the first edge further extending from the second end along a length of the extension arm such that the first edge extends continuously from the first end to an end of the extension arm remote from the second end, and
wherein the first edge is flat along the central body and convex along the extension arm.

2. The spacer guide of claim 1, further comprising a plurality of projections disposed on a second surface of the extension arm, the second surface opposite the first surface.

3. The spacer guide of claim 2, wherein each of the plurality of projections disposed on the second surface of the extension arm is directly opposite one of the plurality of projections disposed on the first surface of the extension arm.

4. The spacer guide of claim 3, wherein the plurality of projections on the first surface and the plurality of projections on the second surface are cylindrically shaped pins that extend orthogonally from the first surface and the second surface, respectively.

5. The spacer guide of claim 4, wherein the plurality of projections on the first surface include at least five projections and the plurality of projections on the second surface include at least five projections.

6. The spacer guide of claim 1, wherein the extension arm has a length extending between the second end of the central body and a free end of the extension arm, the length being greater than a distance between the first end and the second end of the central body.

7. The spacer guide of claim 6, wherein the free end of the extension arm is further from the second end of the central body than any other location on the extension arm.

8. The spacer guide of claim 1, wherein the first surface is planar and extends over the extension arm and the central body.

9. The spacer guide of claim 1, further comprising a mount extending from the second end of the central body, the mount separated from the extension arm by the central body and sized for disposal in a slot of a bone resection guide.

10. A method of positioning instrumentation used in ankle surgery, the method comprising:
attaching a spacer guide to a bone resection guide, the spacer guide comprising:
a central body extending between a first end and a second end, the central body having a first width at the second end;
an extension arm extending from the second end of the central body; and
a plurality of projections disposed on a first surface of the extension arm,
wherein the extension arm has a second width parallel to the first width and measured across the extension arm at one of the plurality of projections, the second width narrower than the first width,
wherein the central body includes a first edge extending between the first end and the second end, the first edge further extending from the second end along a length of the extension arm such that the first edge extends continuously from the first end to an end of the extension arm remote from the second end, and
wherein the first edge is flat along the central body and convex along the extension arm; and
viewing a bone to be resected from a lateral side of the spacer guide.

11. A spacer guide comprising:
a central body extending between a first end and a second end, the central body having a first width at the second end;
an extension arm extending from the central body,
wherein the central body includes a first edge extending between the first end and the second end, the first edge further extending from the second end along a length of the extension arm such that the first edge extends continuously from the first end to an end of the extension arm remote from the second end, and
wherein the first edge is flat along the central body and convex along the extension arm; and
a plurality of projections disposed on a first surface of the extension arm and on a second surface of the extension arm, the second surface opposite the first surface and parallel to the first surface.

12. The spacer guide of claim 11, wherein the first surface of the extension arm is planar.

13. The spacer guide of claim 11, further comprising a mount extending from the central body, the mount separated from the extension arm by the central body and sized for disposal in a slot of a resection guide.

14. The spacer guide of claim 11, wherein each of the plurality of projections disposed on the second surface of the extension arm is directly opposite one of the plurality of projections disposed on the first surface of the extension arm.

15. The spacer guide of claim 14, wherein the plurality of projections on the first surface and on the second surface are cylindrically shaped pins that extend orthogonally from the first surface and the second surface, respectively.

16. The spacer guide of claim 15, wherein the plurality of projections on the first surface include at least five projections and the plurality of projections on the second surface include at least five projections.

17. The spacer guide of claim 16, wherein the plurality of projections on the first surface are positioned such that each projection is located at a unique location on a length of the extension arm, the length measured from the central body to a free end of the extension arm.

18. A method of positioning instrumentation used in ankle surgery, the method comprising:
inserting a spacer guide into a slot of a bone resection guide, the spacer guide comprising:
a central body extending between a first end and a second end, the central body having a first width at the second end;
an extension arm extending from the central body,
wherein the central body includes a first edge extending between the first end and the second end, the first edge further extending from the second end along a length of the extension arm such that the first edge extends continuously from the first end to an end of the extension arm remote from the second end, and wherein the first edge is flat along the central body and convex along the extension arm; and a plurality of projections disposed on a first surface of the extension arm and on a second surface of the extension arm, the second surface opposite the first surface and parallel to the first surface; and viewing a bone from a lateral side of the spacer guide to evaluate a path of bone resection, wherein the bone resection guide is positioned over the bone so that a plane through the slot is also a resection plane.

\* \* \* \* \*